(12) United States Patent
Xu

(10) Patent No.: US 12,383,505 B2
(45) Date of Patent: Aug. 12, 2025

(54) NANOPARTICLE FOR THE REMODELING OF CANCER-ASSOCIATED FIBROBLASTS

(71) Applicant: University of South Carolina, Columbia, SC (US)

(72) Inventor: Peisheng Xu, Chapin, SC (US)

(73) Assignee: UNIVERSITY OF SOUTH CAROLINA, Columbia, SC (US)

(*) Notice: Subject to any disclaimer, the term of this patent is extended or adjusted under 35 U.S.C. 154(b) by 94 days.

(21) Appl. No.: 17/965,880

(22) Filed: Oct. 14, 2022

(65) Prior Publication Data

US 2023/0310331 A1 Oct. 5, 2023

Related U.S. Application Data

(60) Provisional application No. 63/289,265, filed on Dec. 14, 2021.

(51) Int. Cl.
| | | |
|---|---|---|
| *A61K 9/50* | (2006.01) | |
| *A61K 9/51* | (2006.01) | |
| *A61K 31/704* | (2006.01) | |
| *A61K 33/244* | (2019.01) | |
| *A61P 35/00* | (2006.01) | |
| *B82Y 40/00* | (2011.01) | |
| *C12N 9/08* | (2006.01) | |
| *B82Y 5/00* | (2011.01) | |

(52) U.S. Cl.
CPC .......... *A61K 9/5068* (2013.01); *A61K 9/5123* (2013.01); *A61K 31/704* (2013.01); *A61K 33/244* (2019.01); *A61P 35/00* (2018.01); *C12N 9/0065* (2013.01); *C12Y 111/01006* (2013.01); *B82Y 5/00* (2013.01); *B82Y 40/00* (2013.01)

(58) Field of Classification Search
None
See application file for complete search history.

(56) References Cited

PUBLICATIONS

Liu et al (Adv. Funct. Mater., Jun. 16, 2021, 31, 1-13). (Year: 2021).*

* cited by examiner

*Primary Examiner* — Celeste A Roney
(74) *Attorney, Agent, or Firm* — DORITY & MANNING, P.A.

(57) ABSTRACT

Described herein are systems and methods for employing a tumor targeted cerium oxide nanoparticle system, T-CeNP, for cancer therapy to hinder cancer associated fibroblast (CAF) transdifferentiation and reprogram CAFs back to normal fibroblasts to reduce tumor size and prevent metastasis.

9 Claims, 57 Drawing Sheets
Specification includes a Sequence Listing.

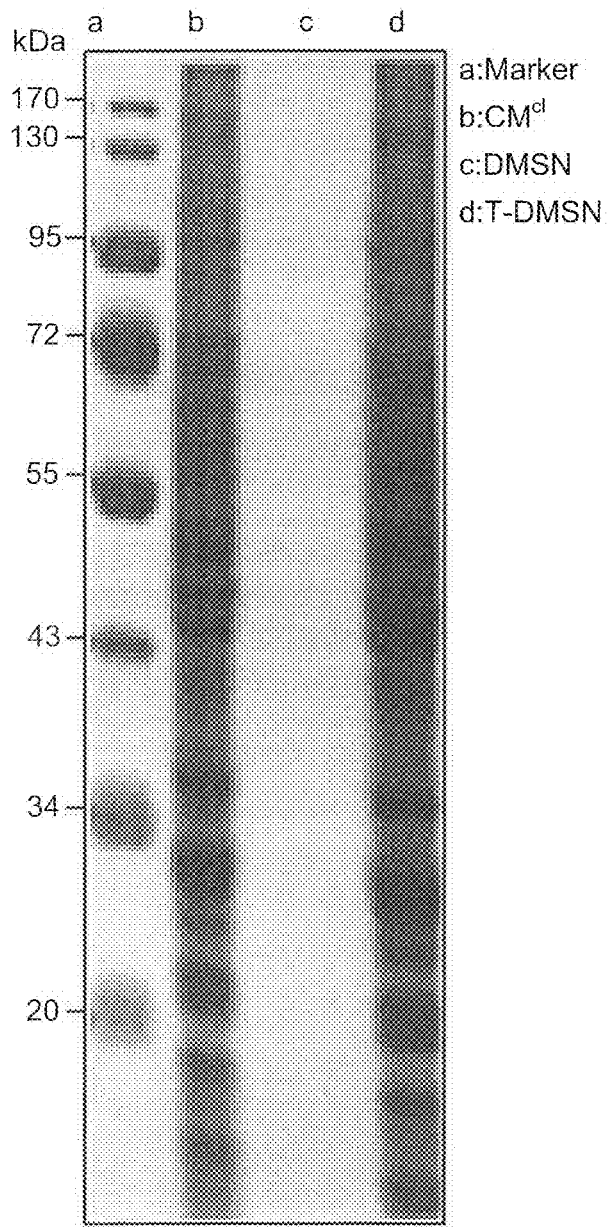
FIG. 2A (CON'T)

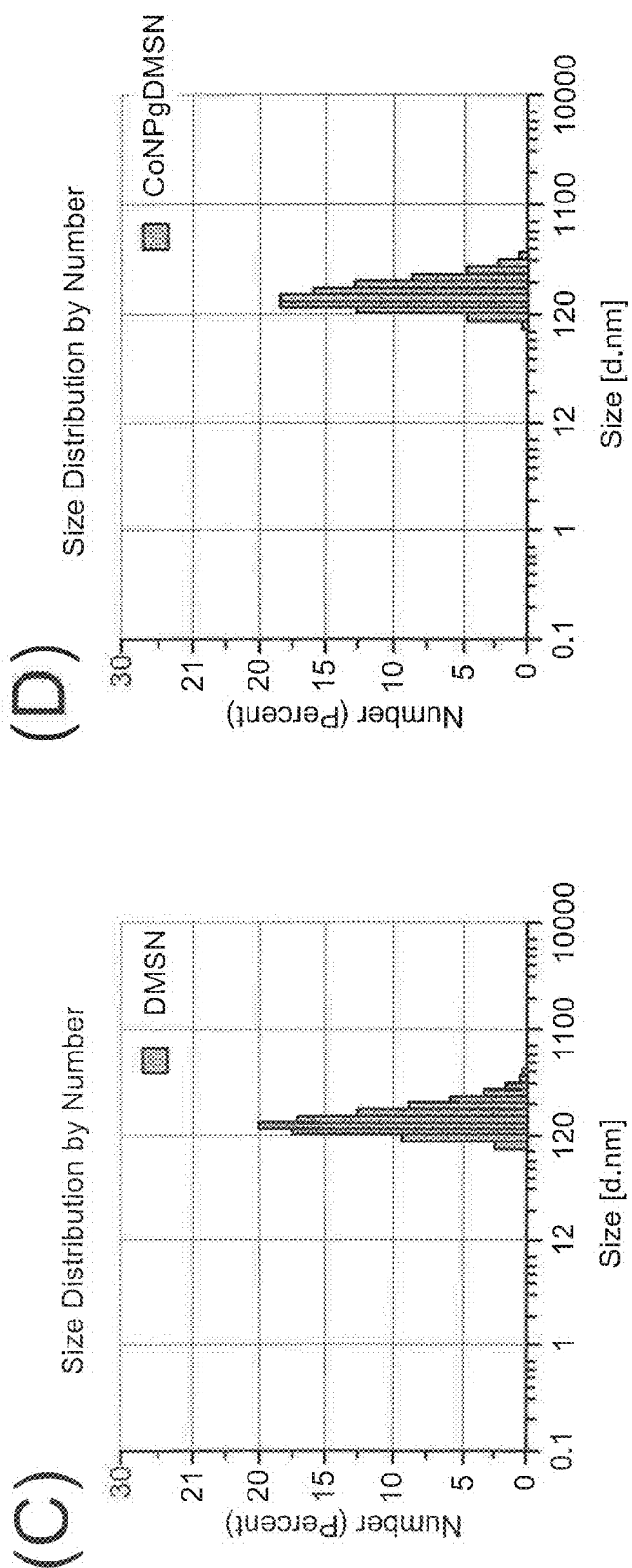
FIG. 2A (CON'T)

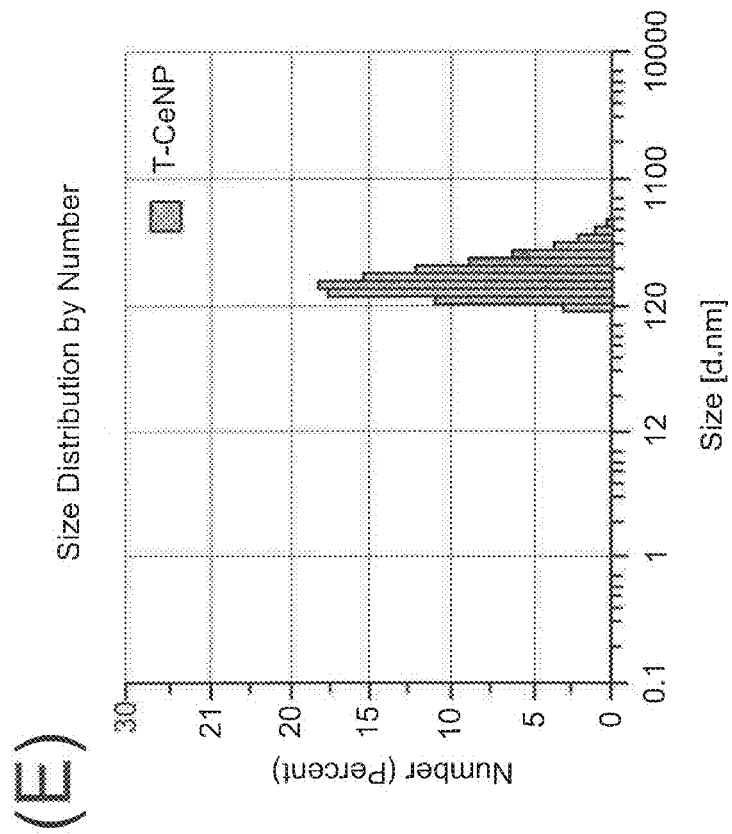
FIG. 2A (CON'T)

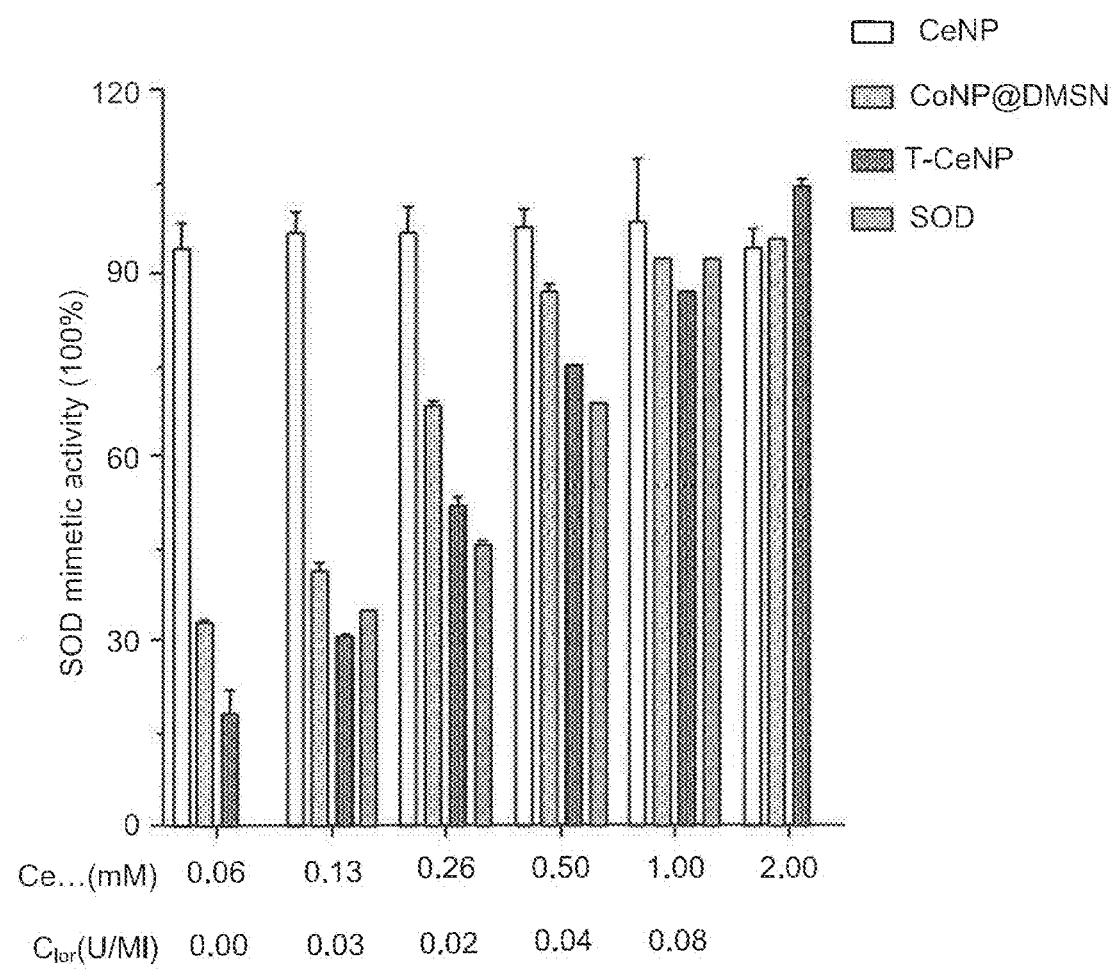
FIG. 2B (CON'T)

(J)
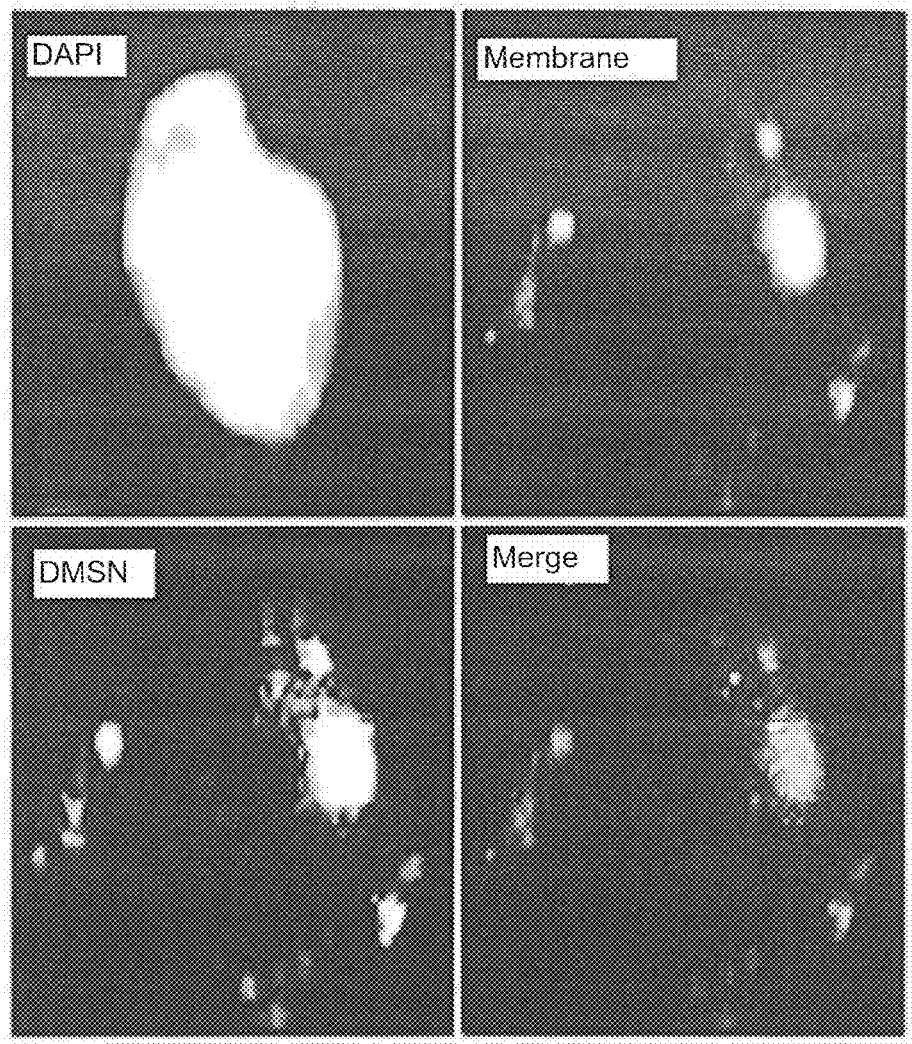
FIG. 2B (CON'T)

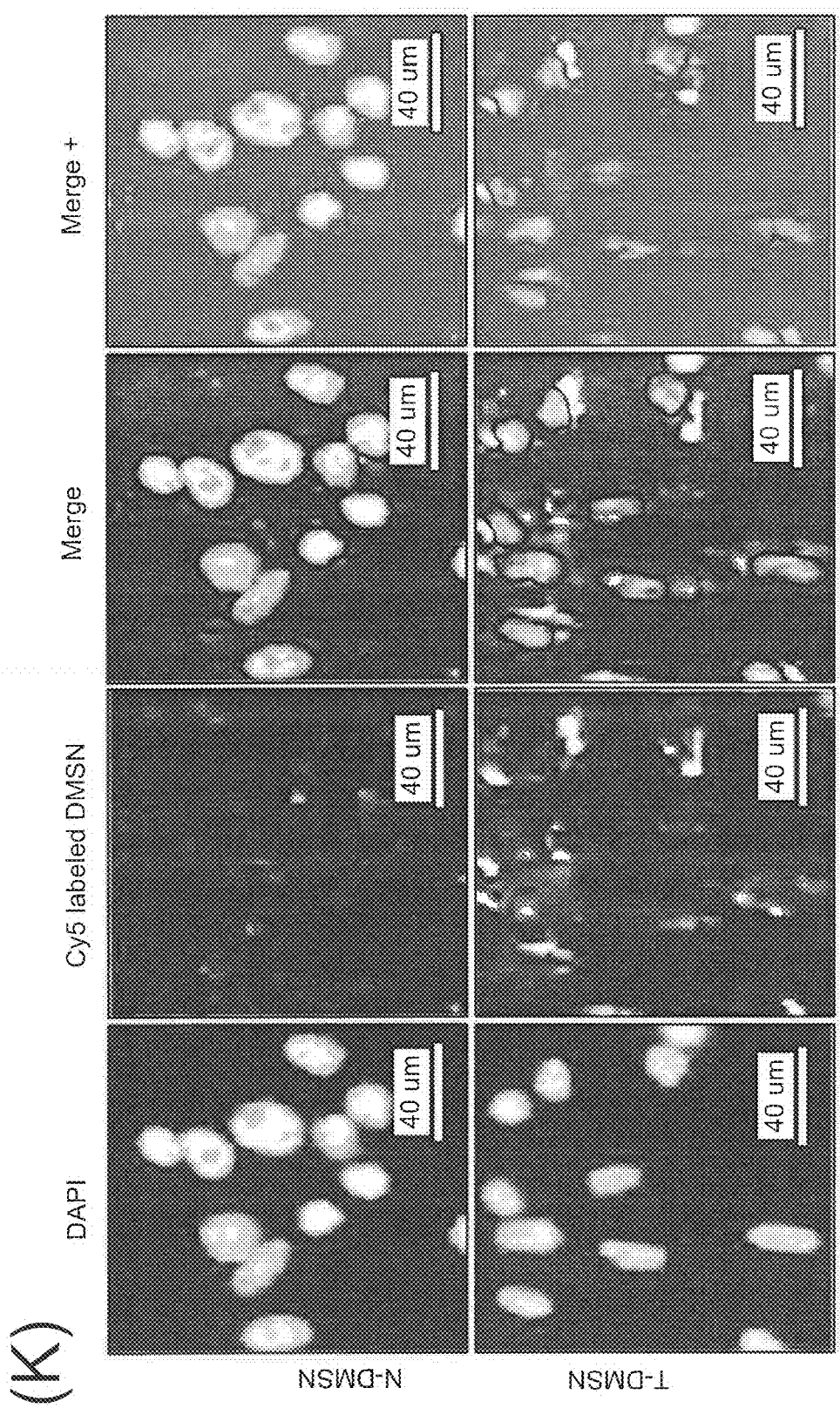
FIG. 2B (CON'T)

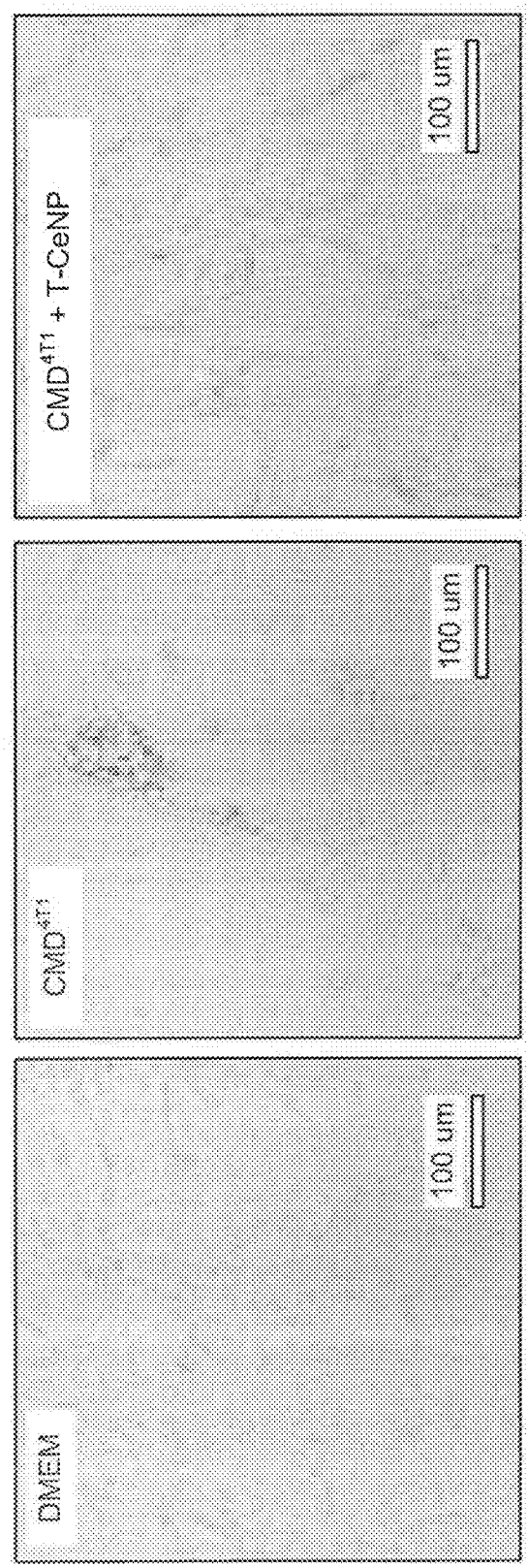
FIG. 4A (CON'T)

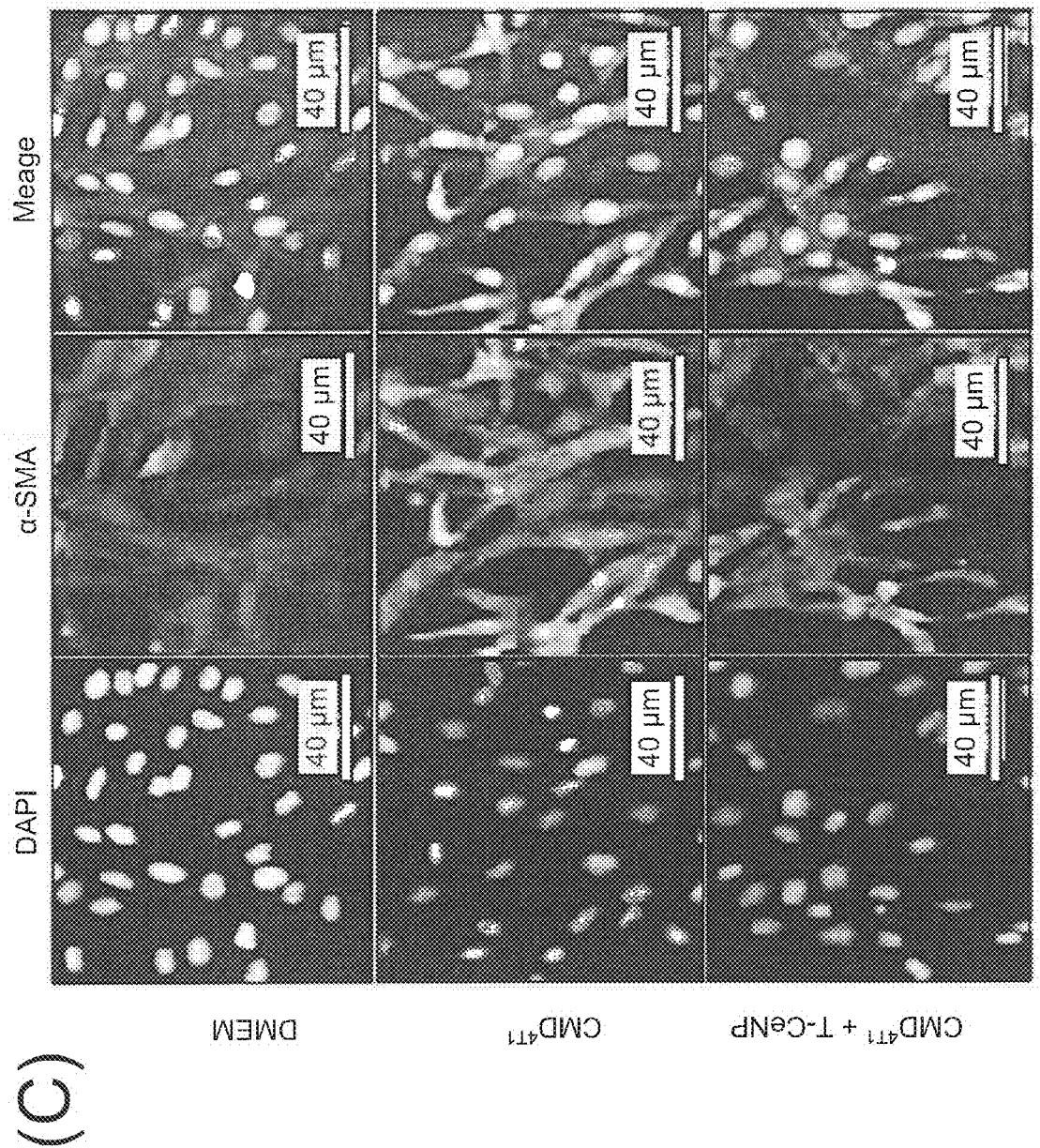
FIG. 4A (CON'T)

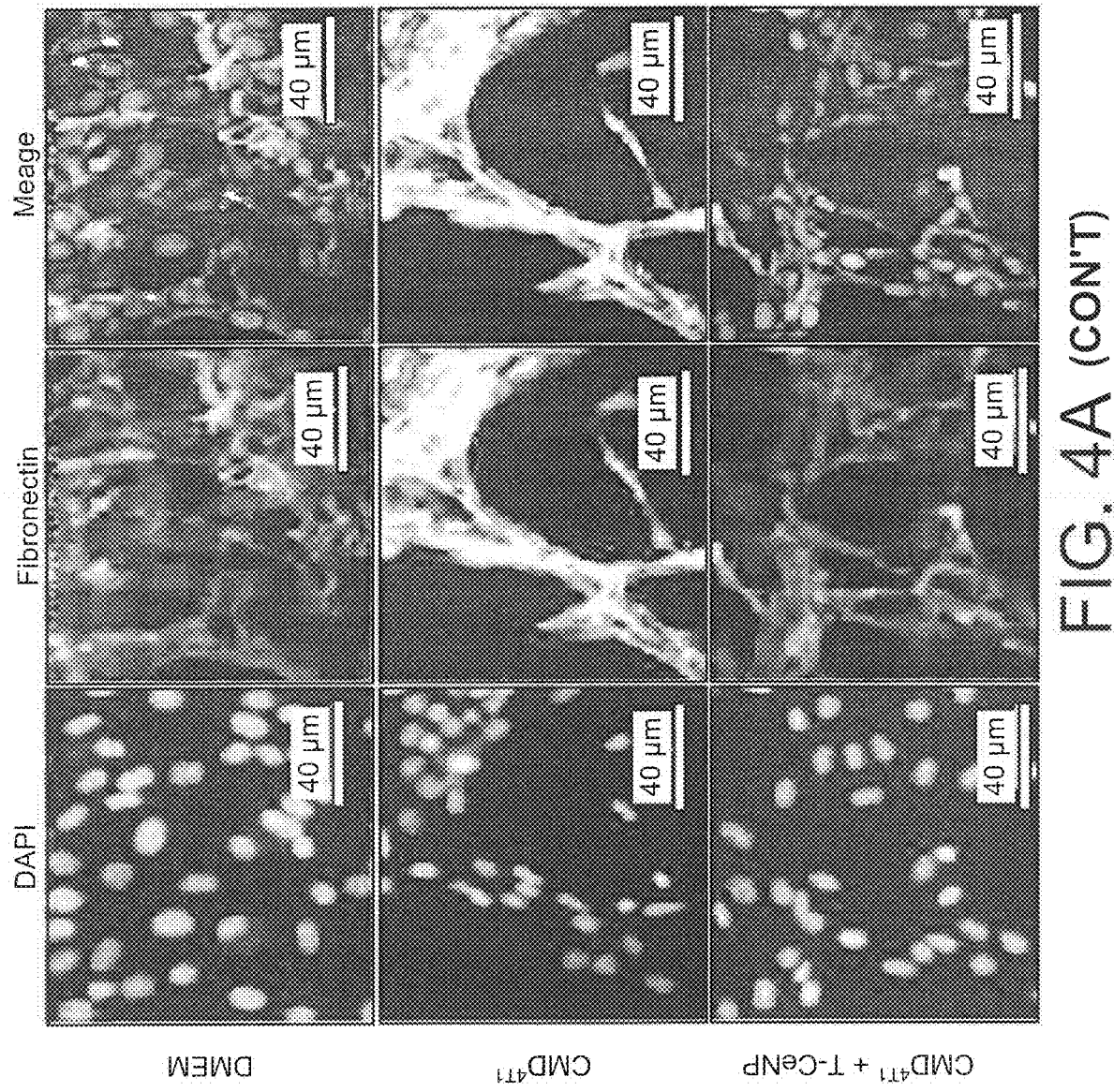
FIG. 4A (CON'T)

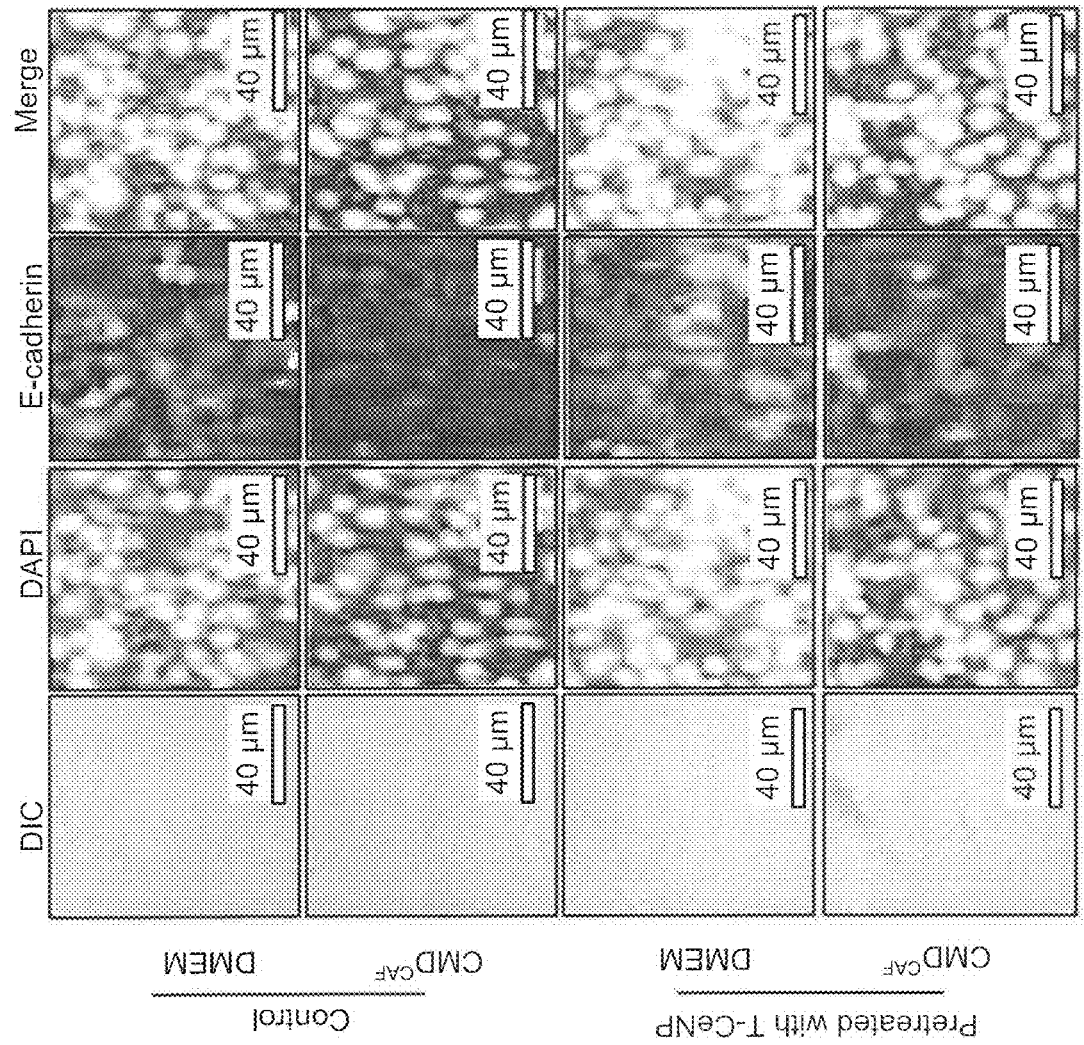
FIG. 5A (CON'T)

FIG. 5A (CON'T)

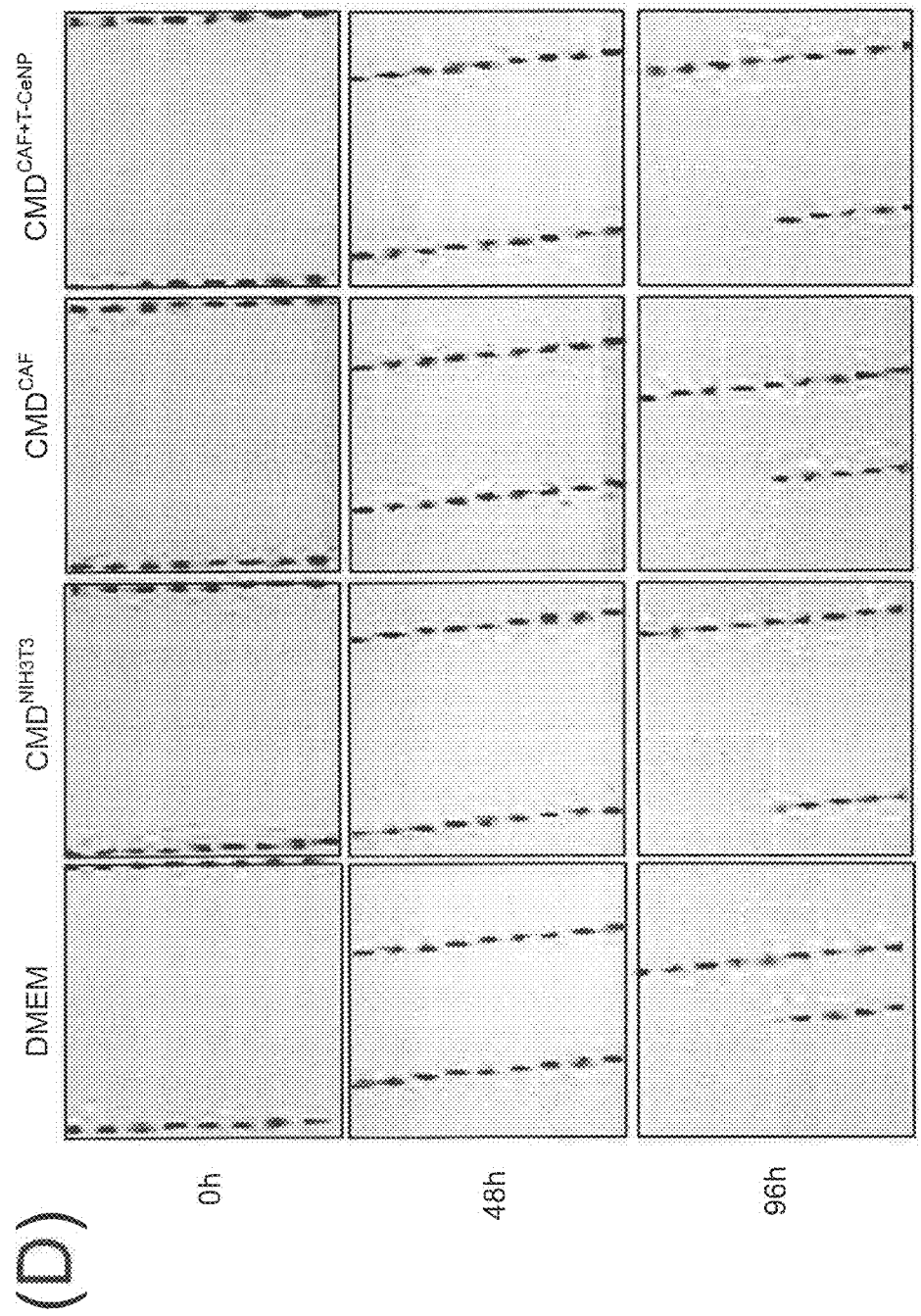
FIG. 5A (CON'T)

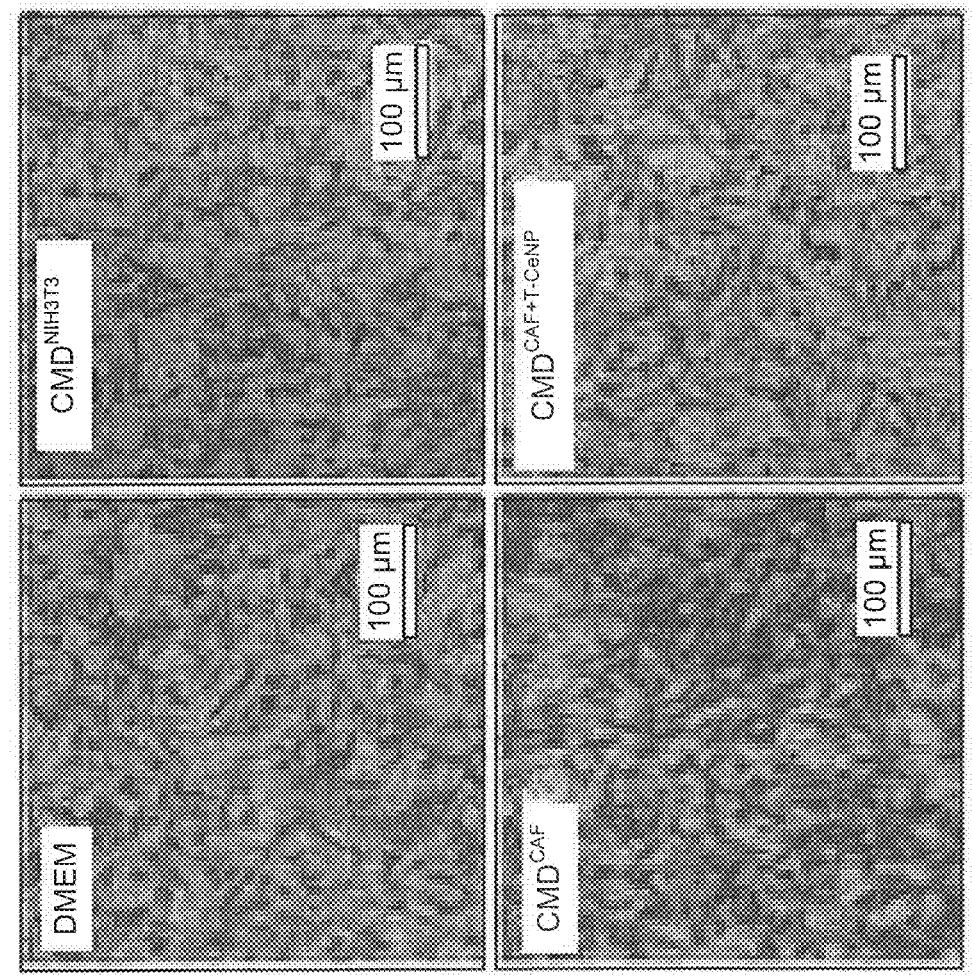
FIG. 5A (CON'T)

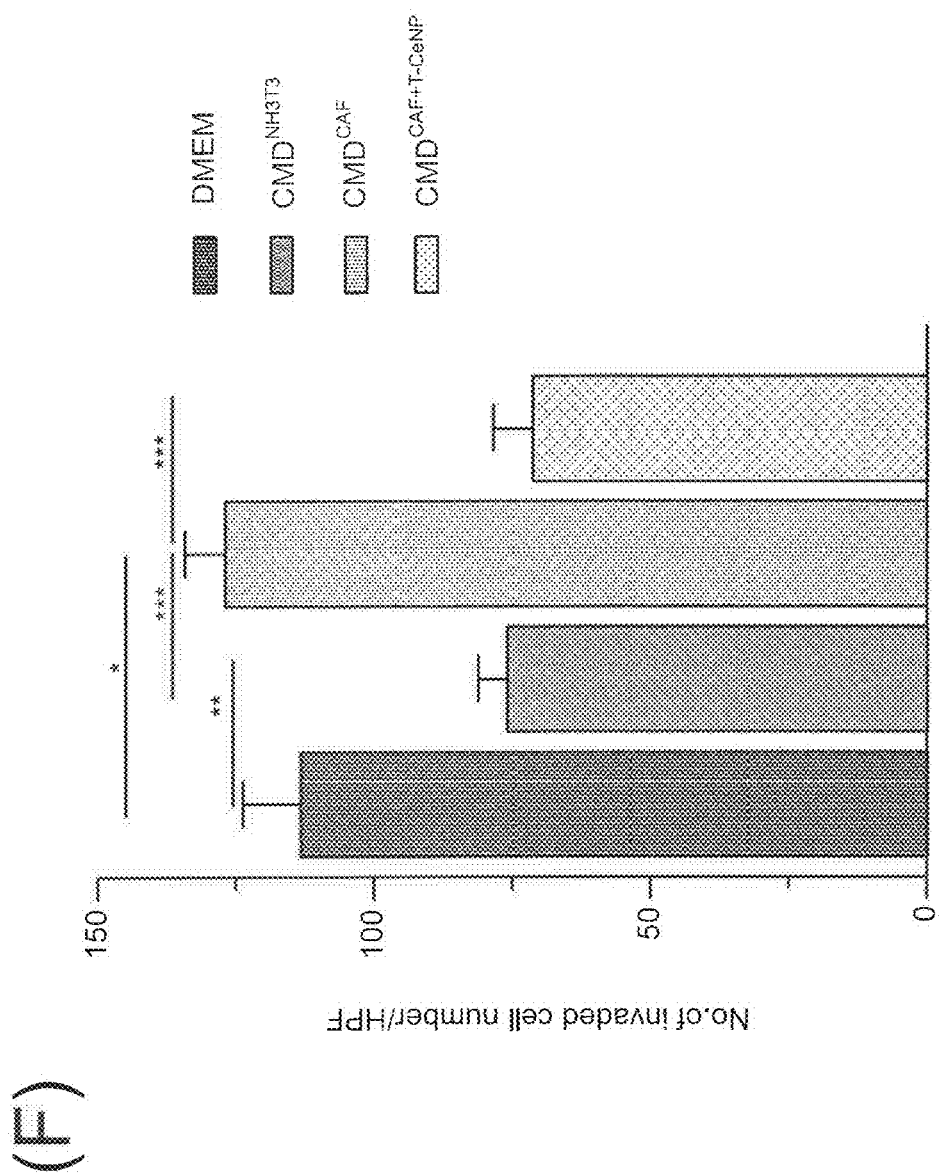
FIG. 5A (CON'T)

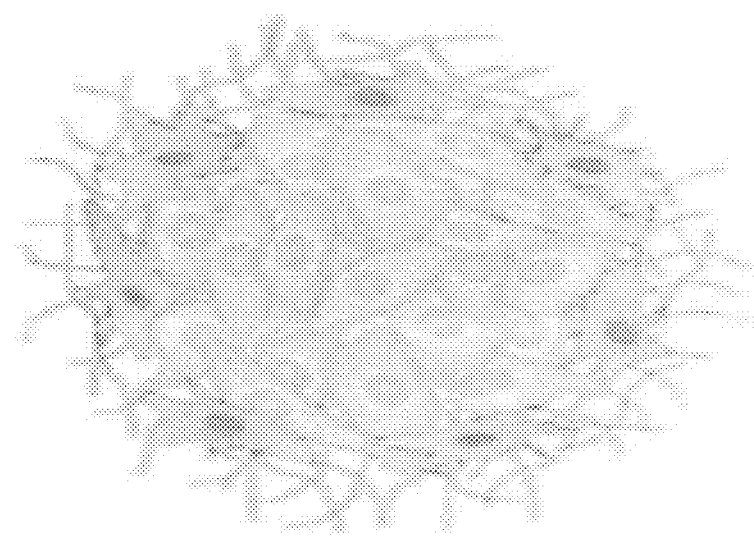
(A)
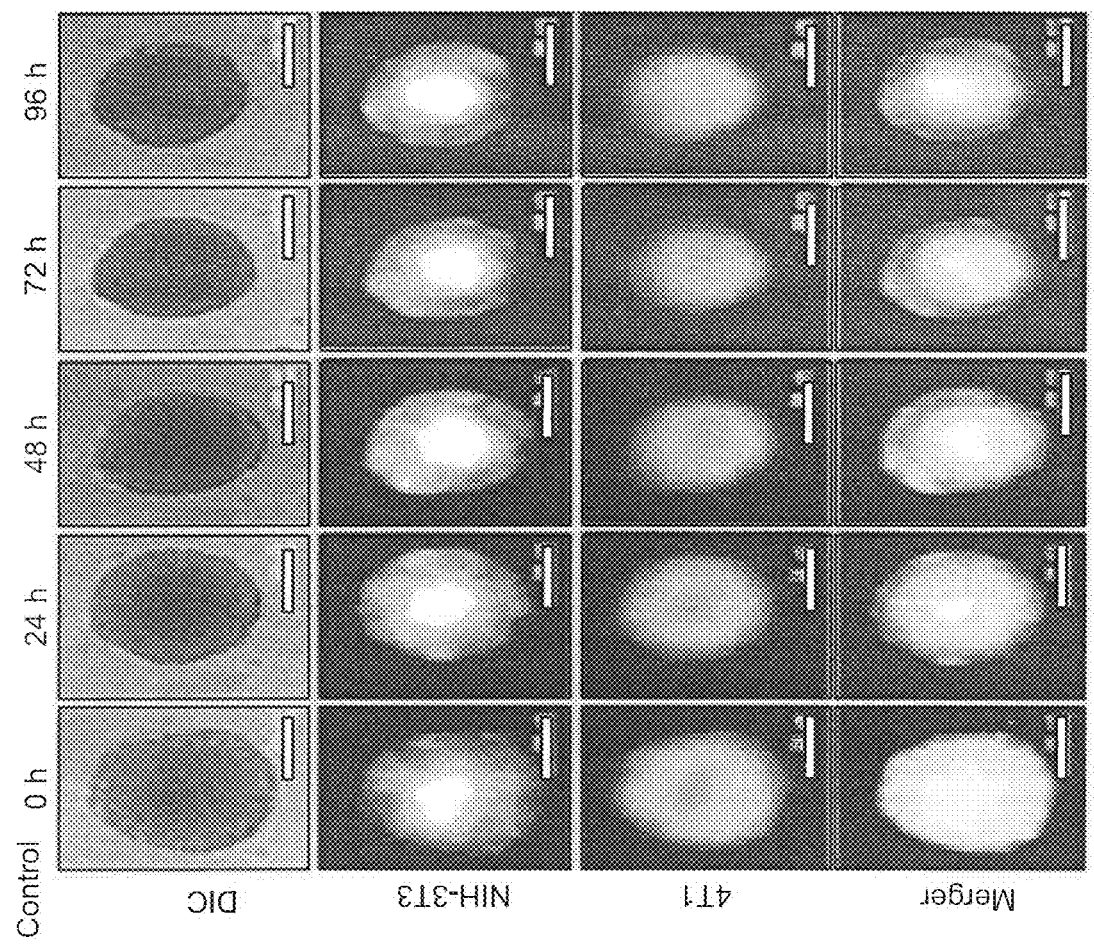
FIG. 7

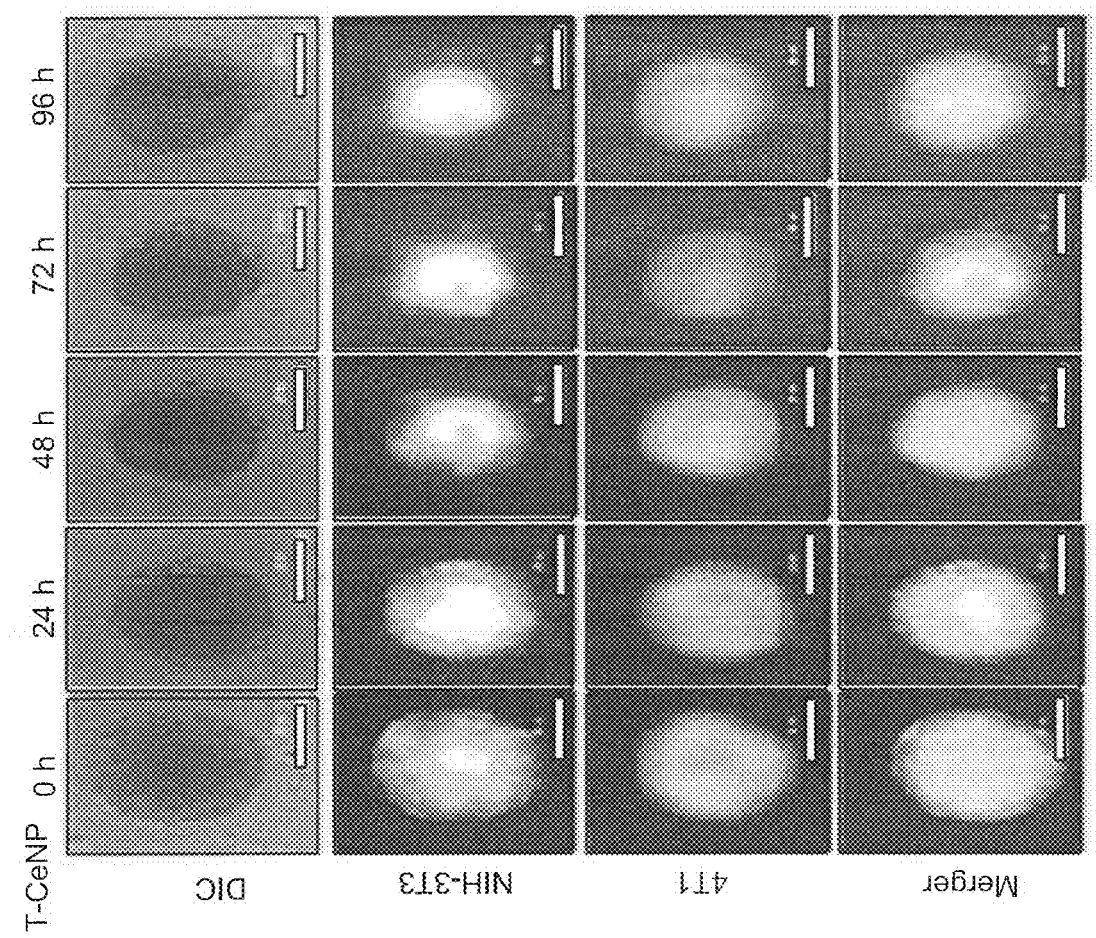
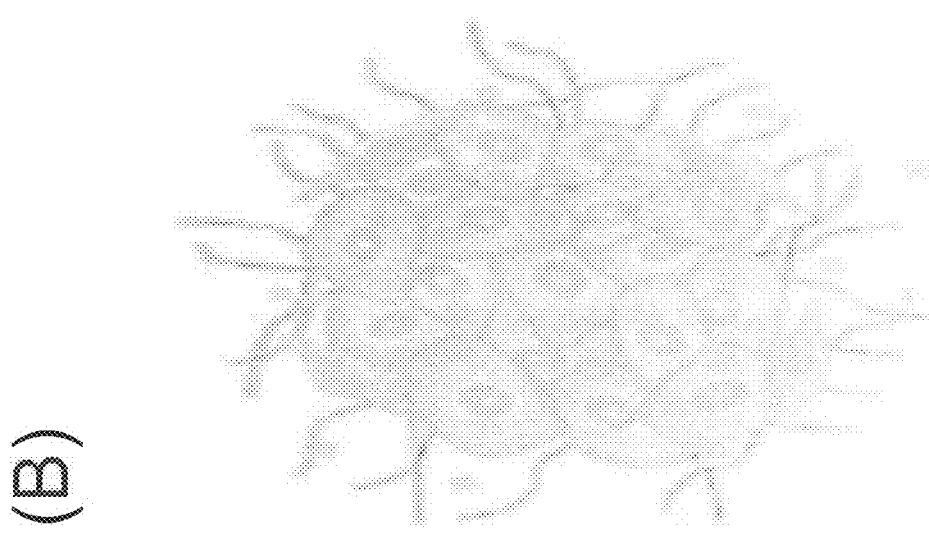
FIG. 7 (CON'T)

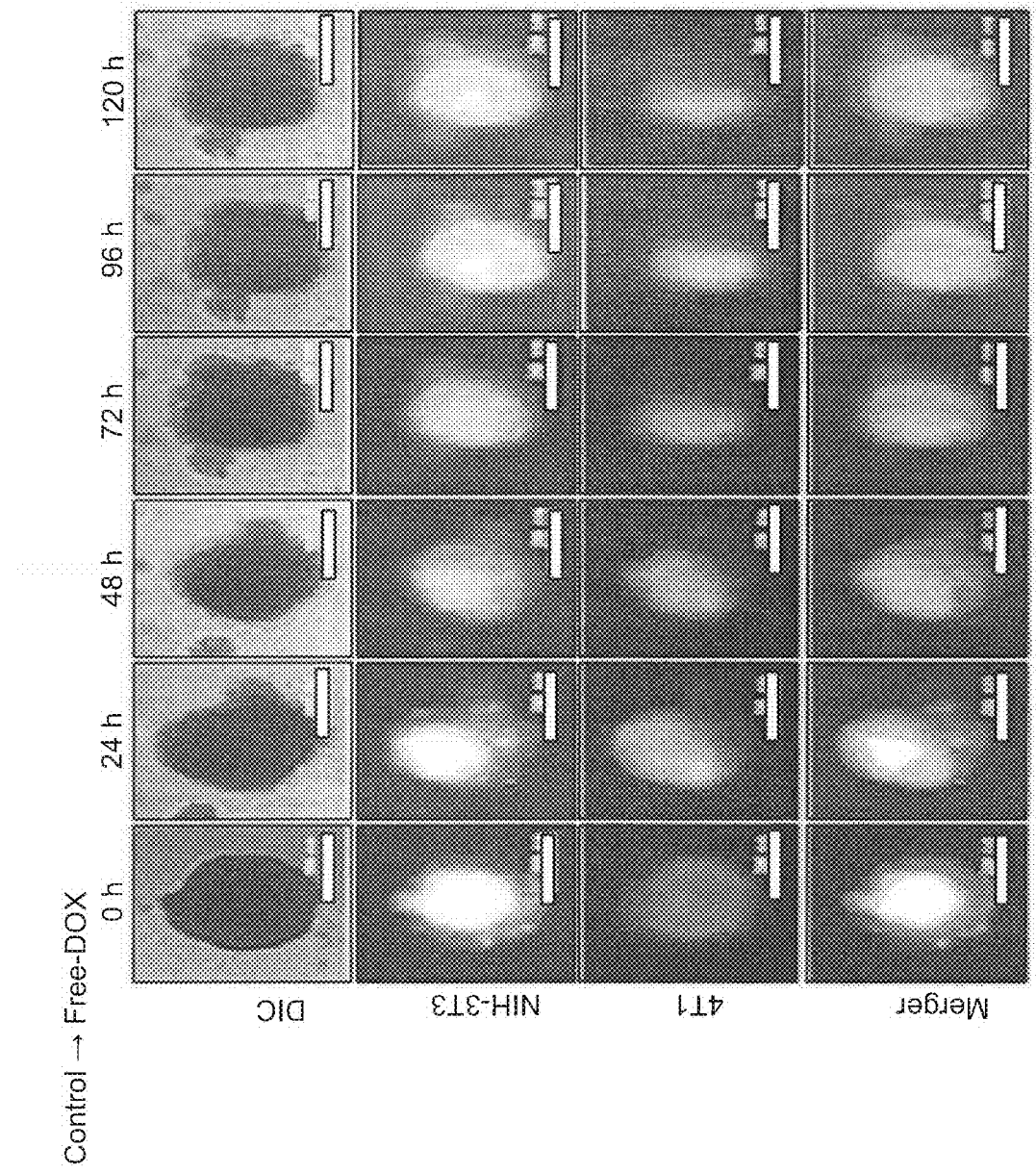
FIG. 7 (CON'T)

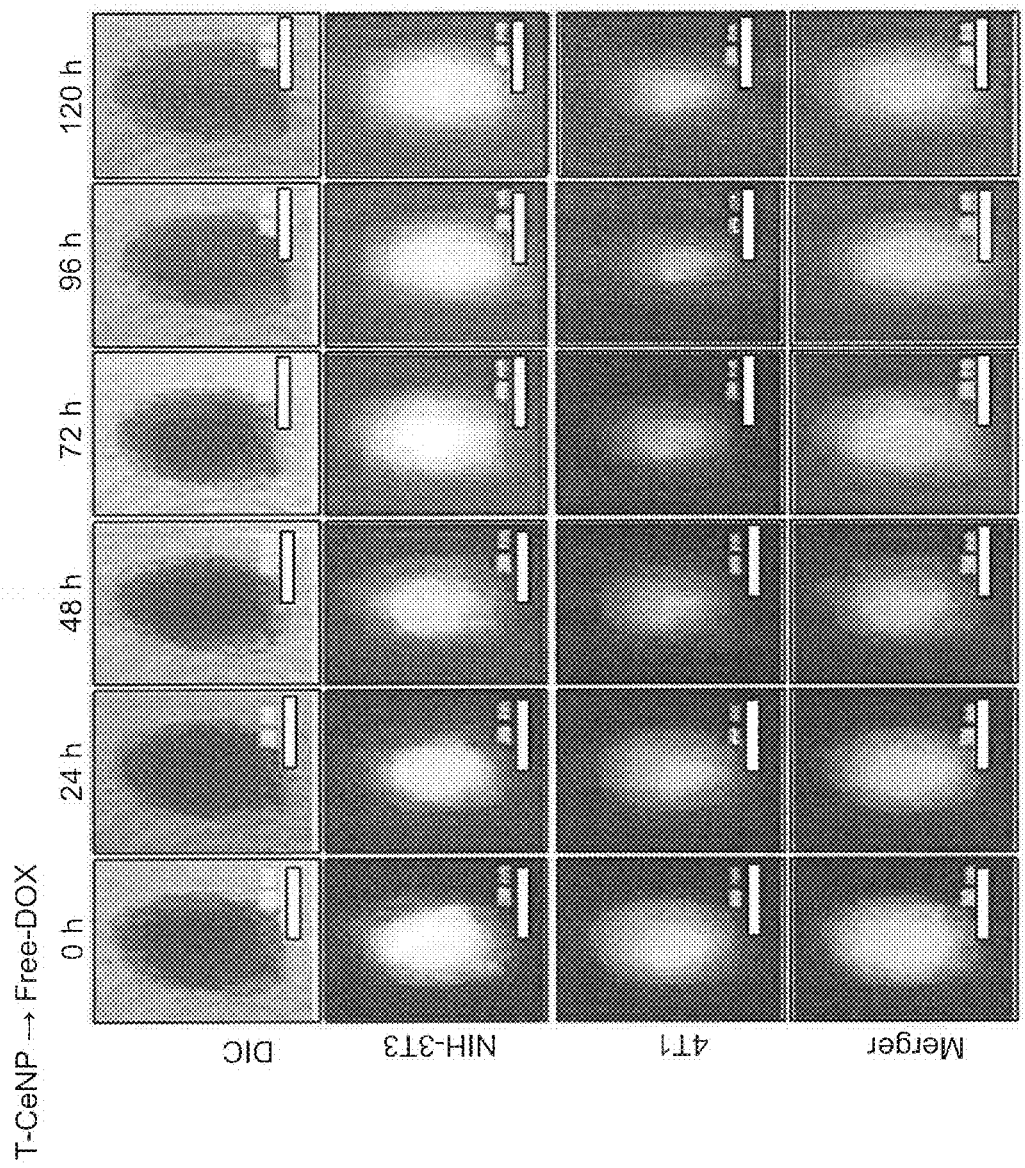
FIG. 7 (CON'T)

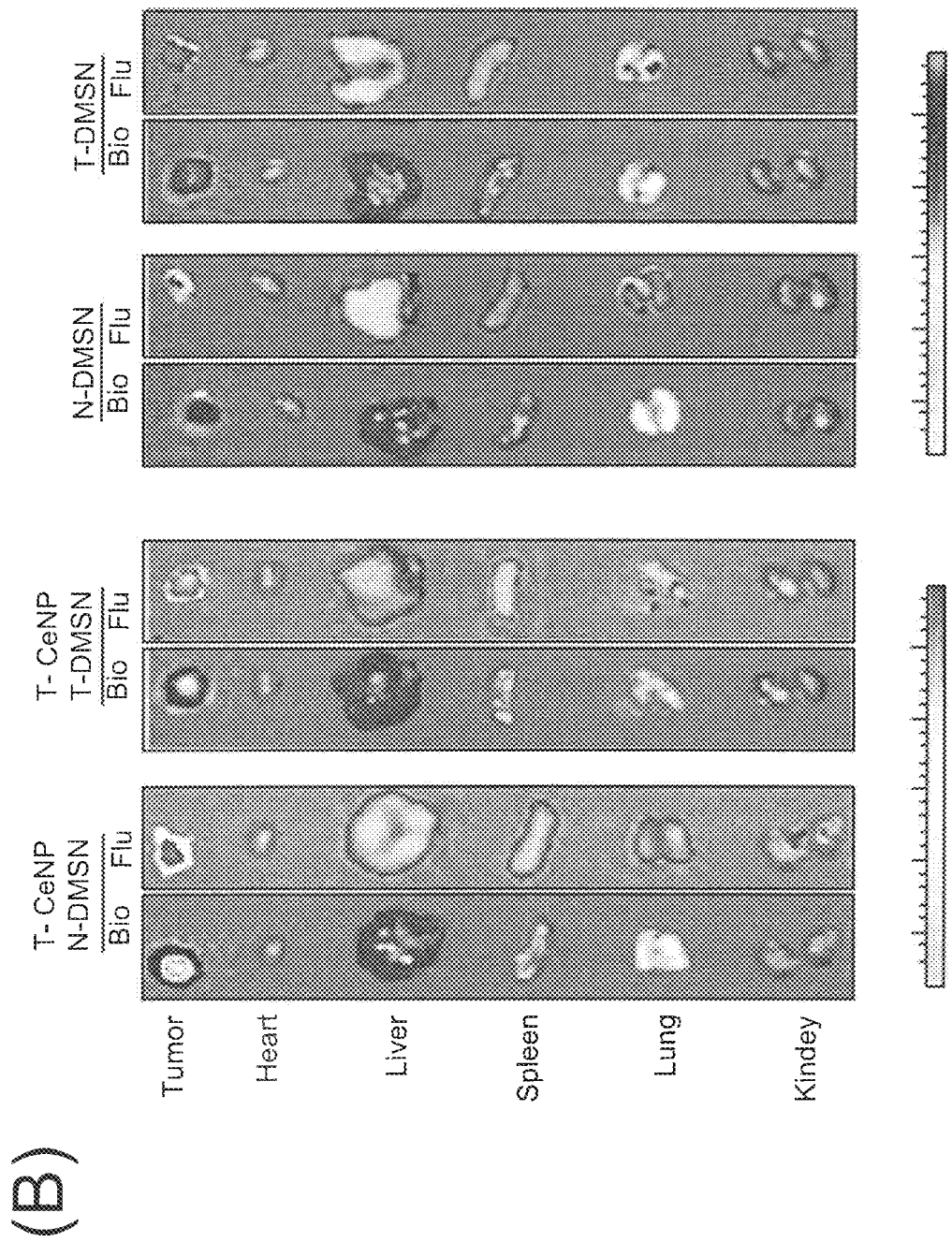
FIG. 8 (CON'T)

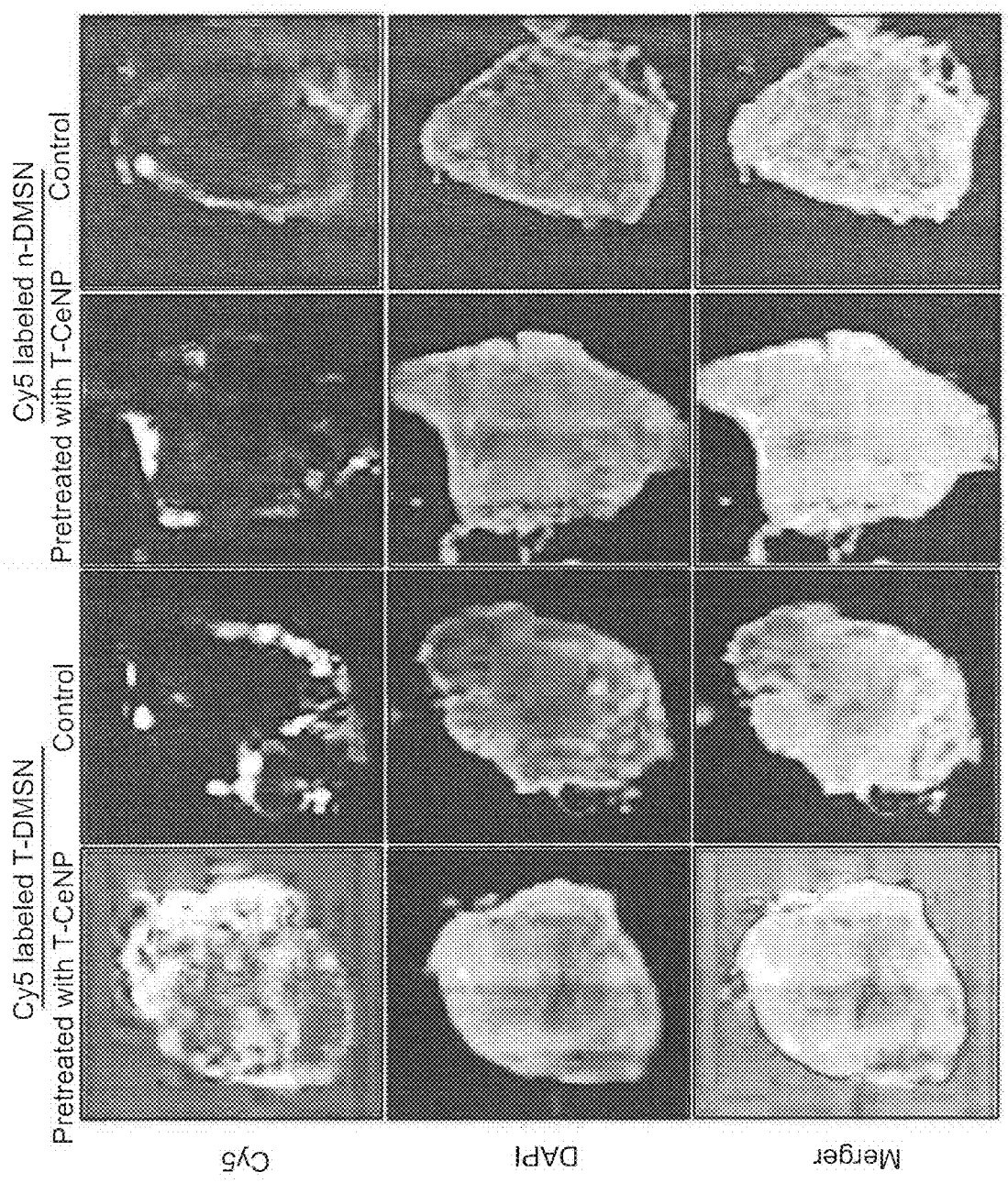
FIG. 8 (CON'T)

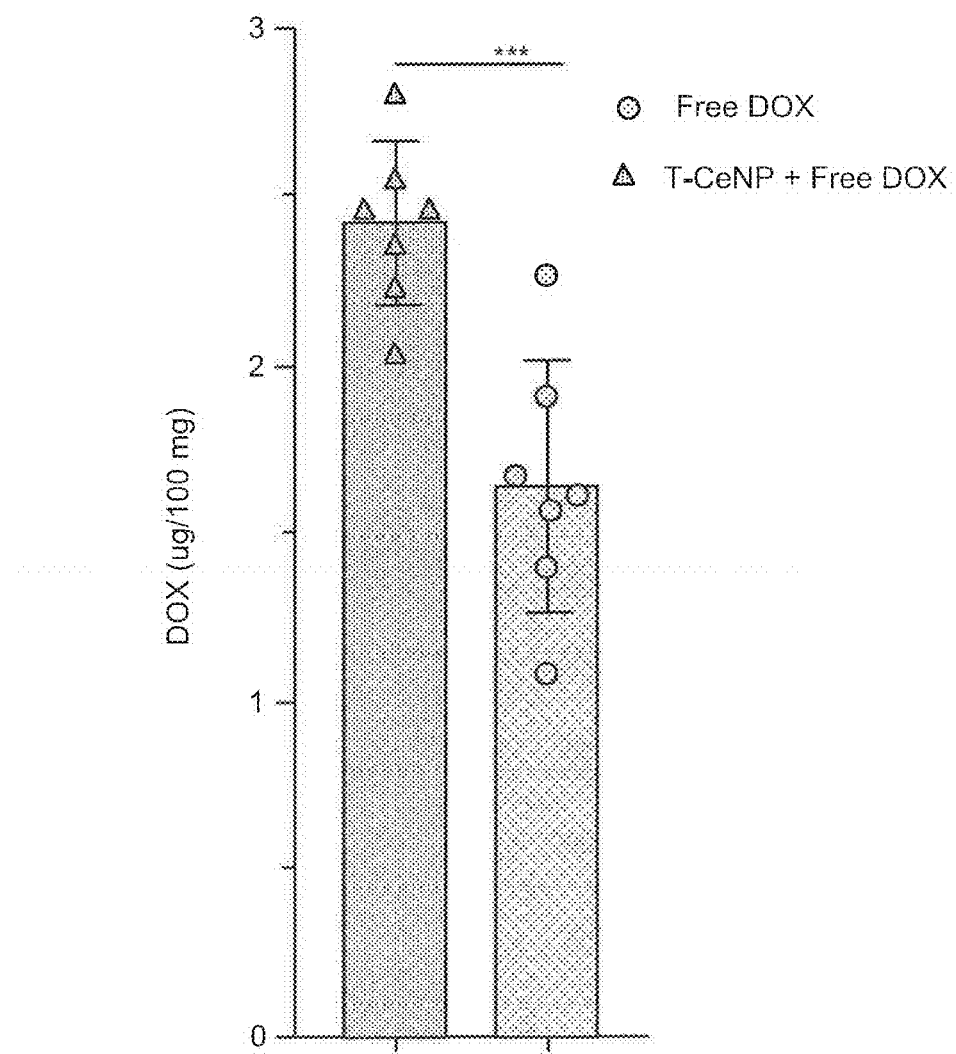
FIG. 8 (CON'T)

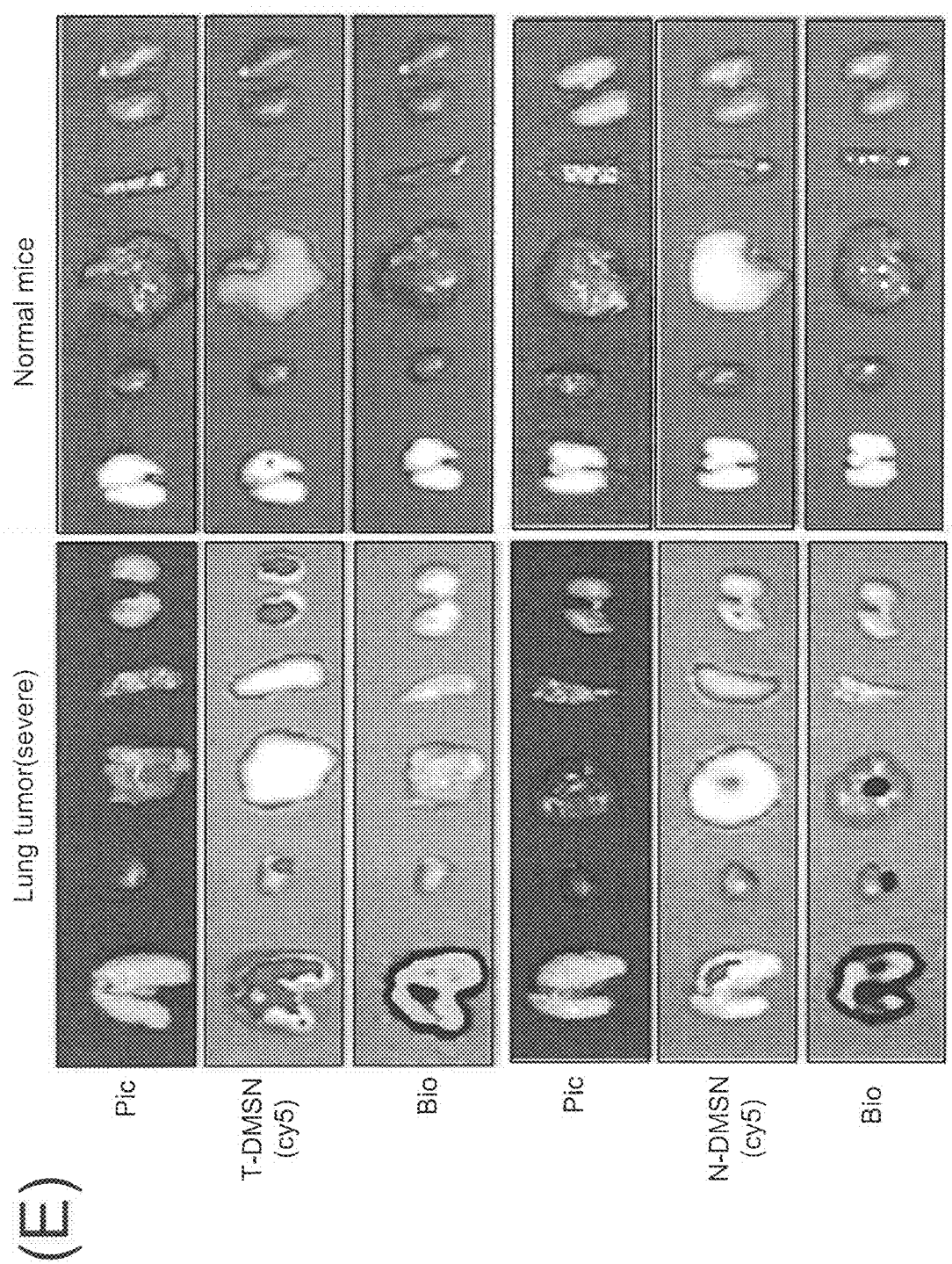
FIG. 8 (CON'T)

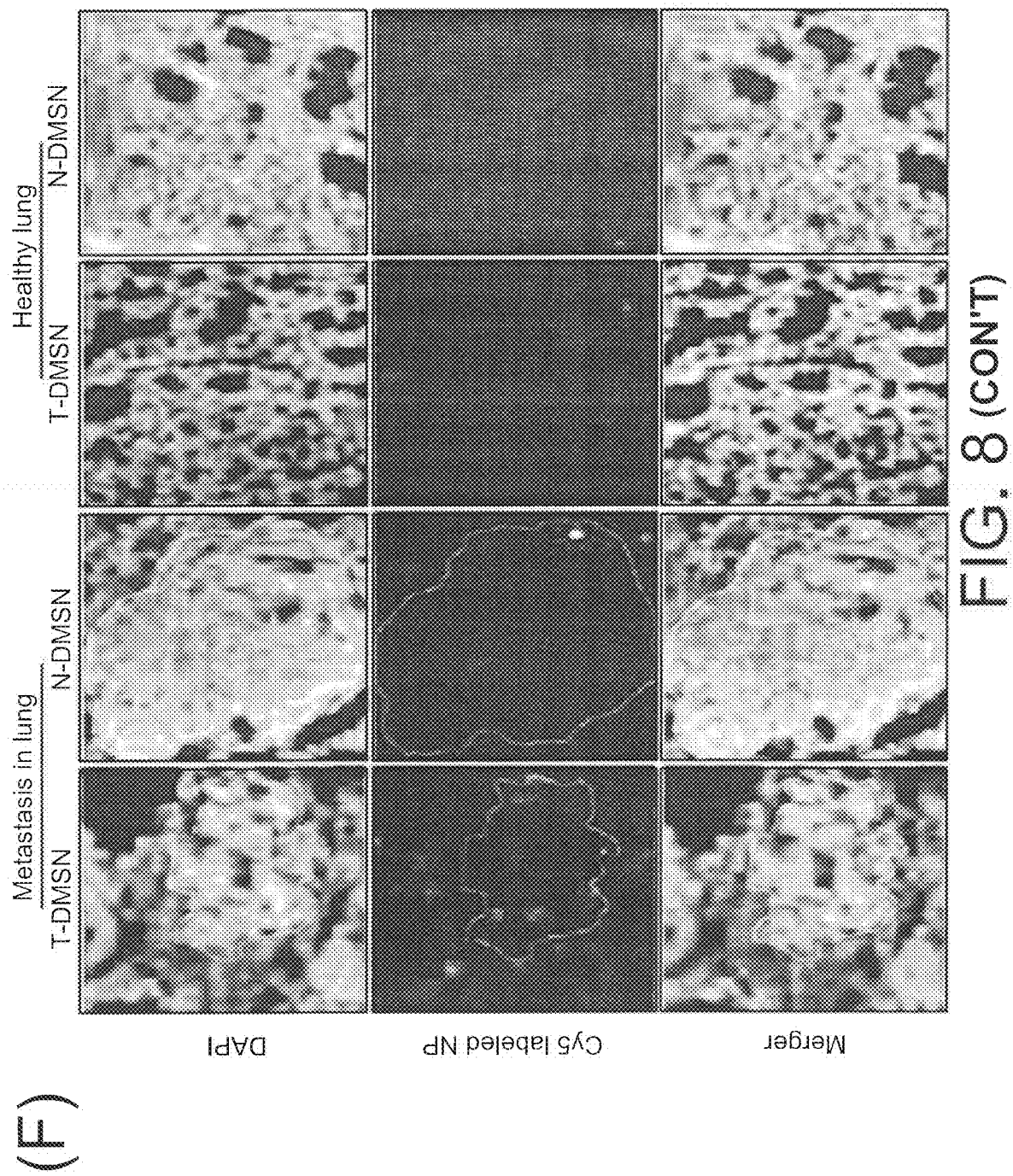
FIG. 8 (CON'T)

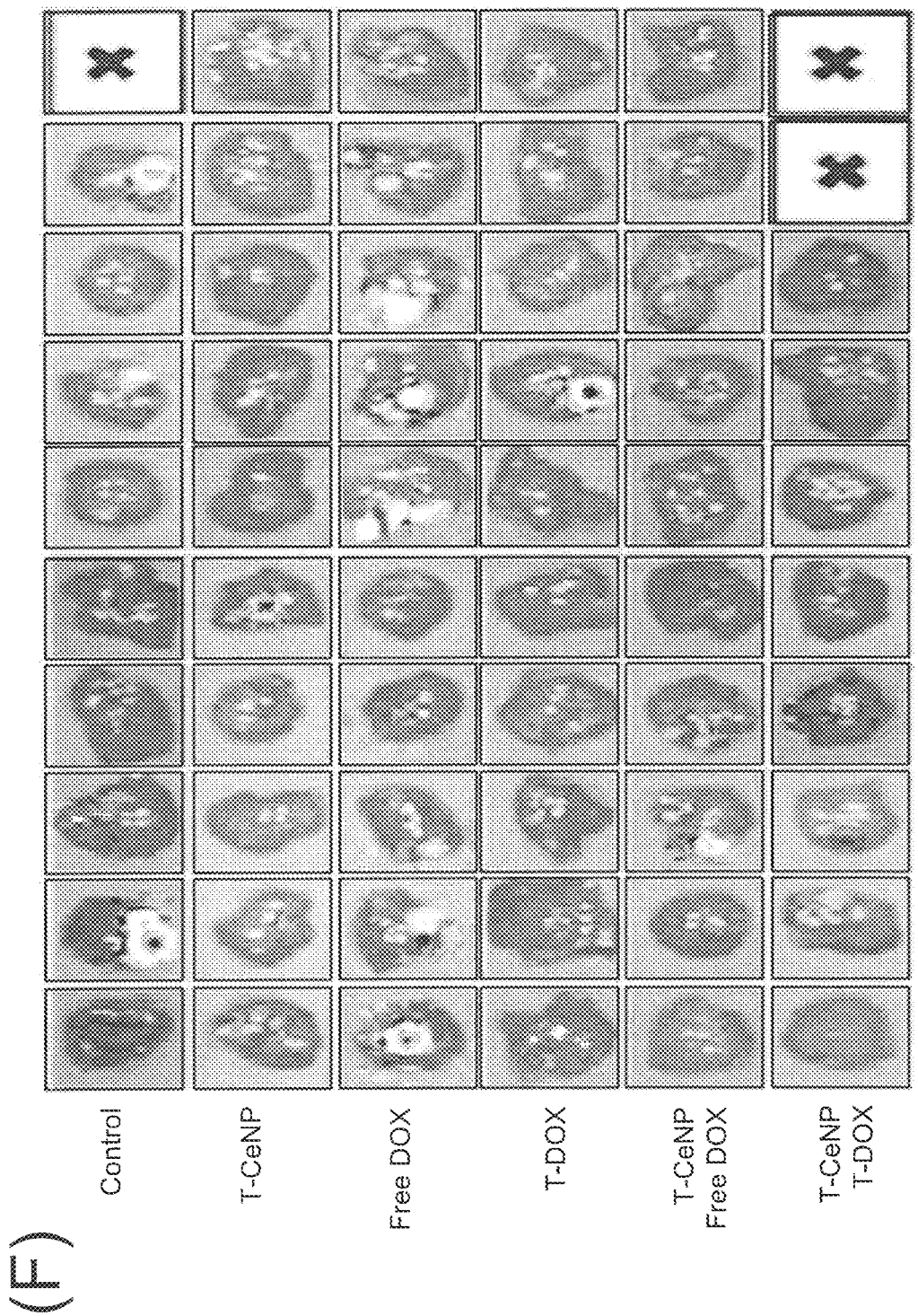
FIG. 9B (CON'T)

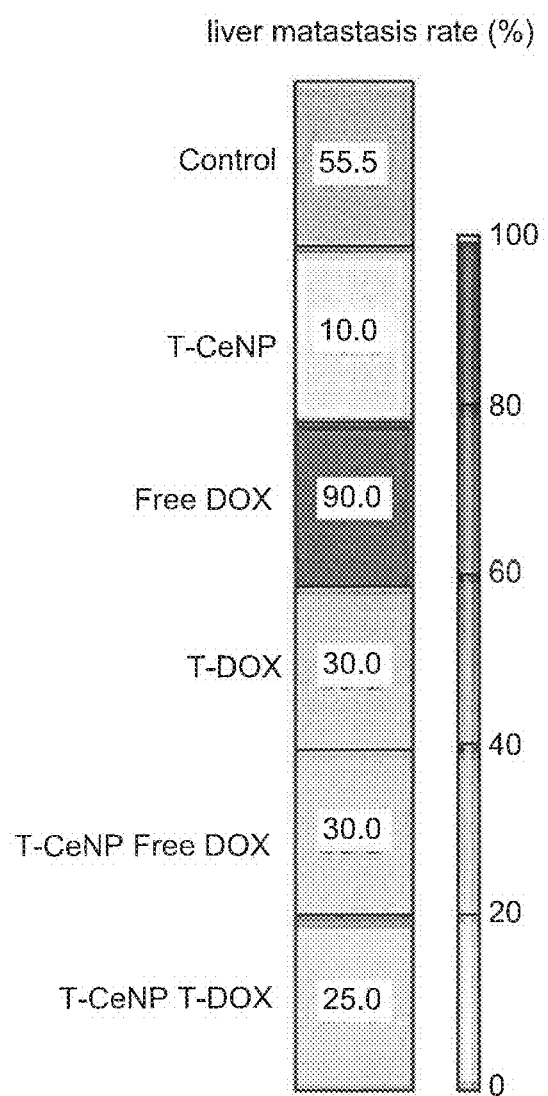
FIG. 9B (CON'T)

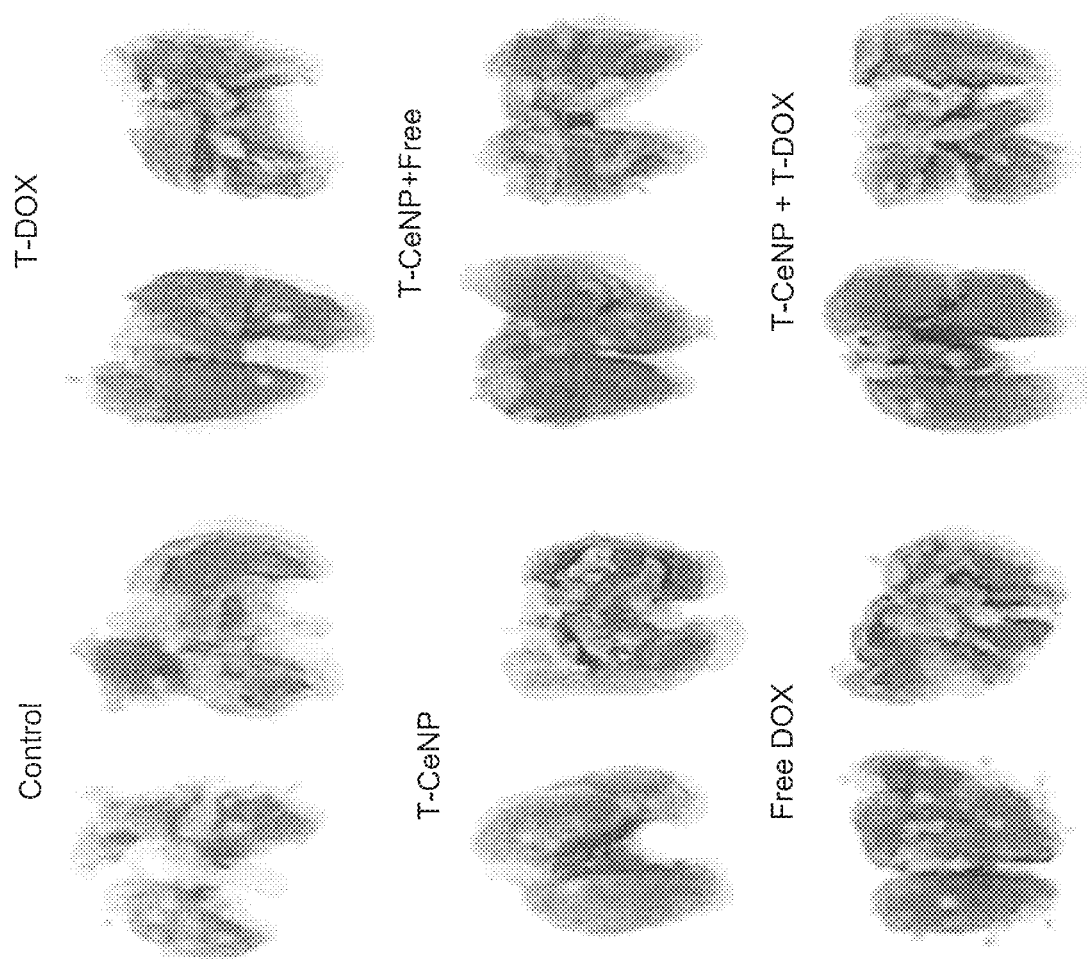
FIG. 9B (CON'T)

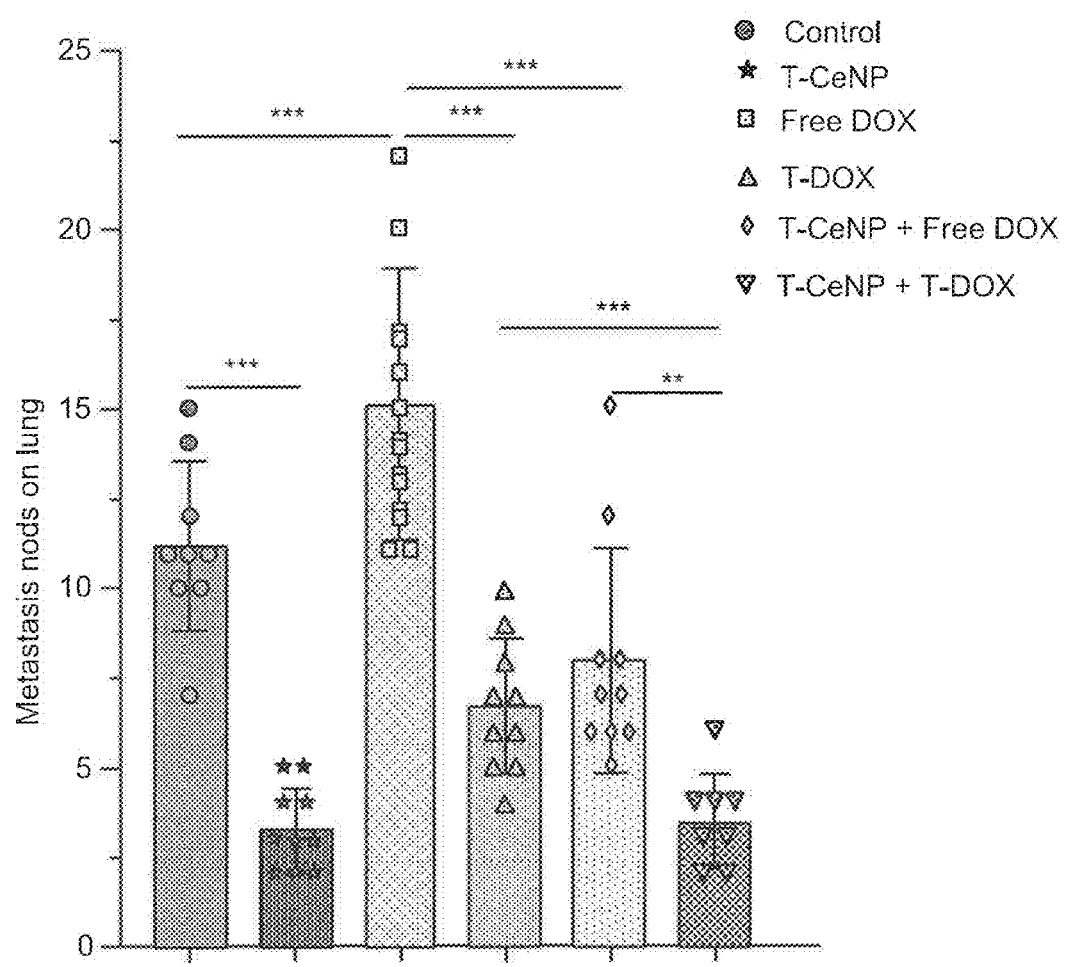
FIG. 9B (CON'T)

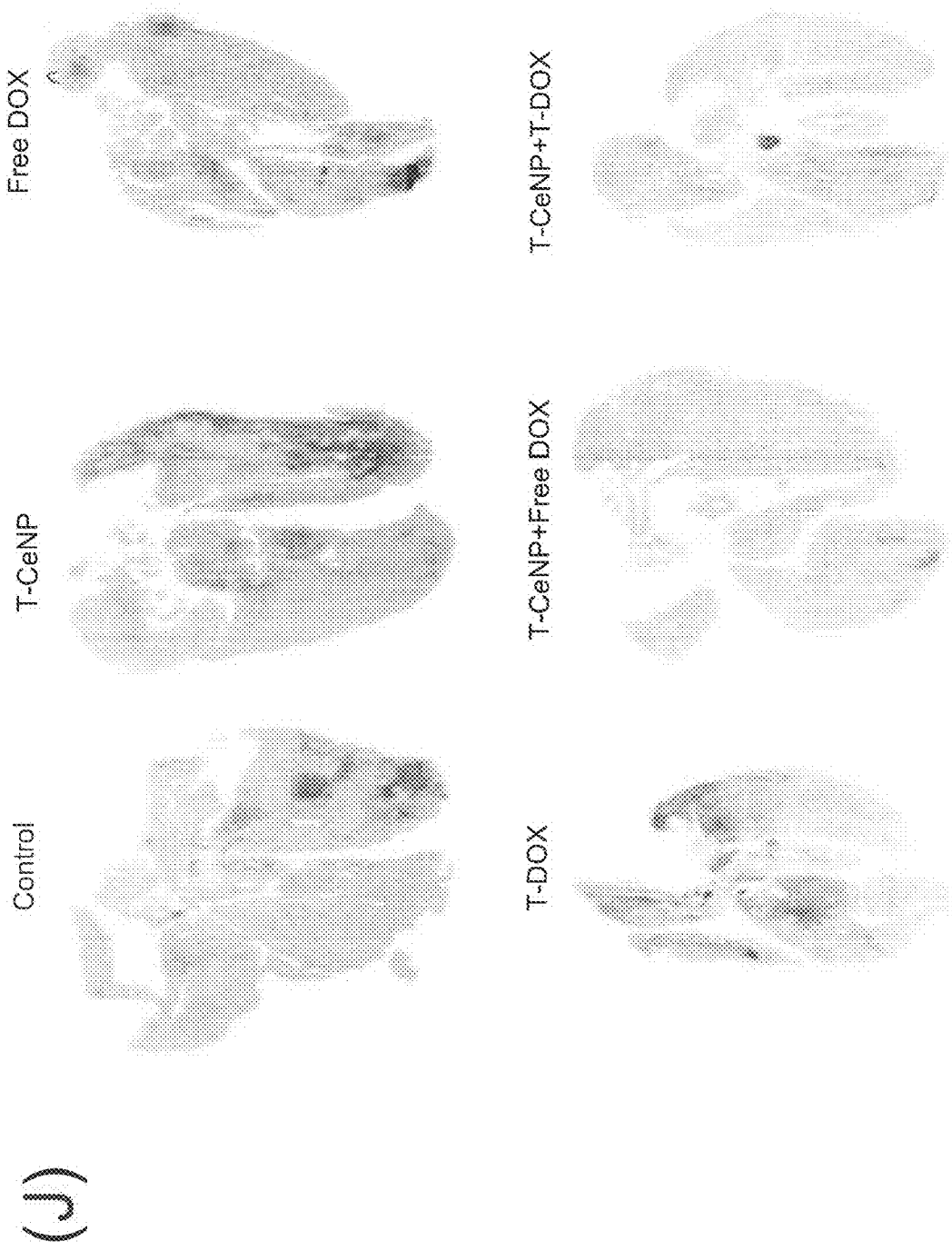
FIG. 9B (CON'T)

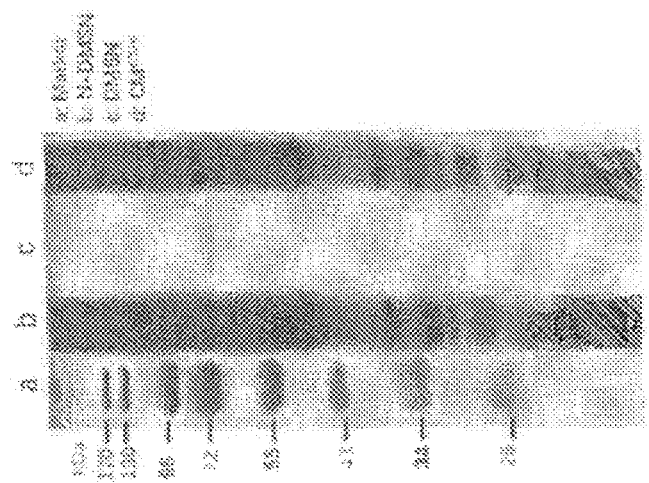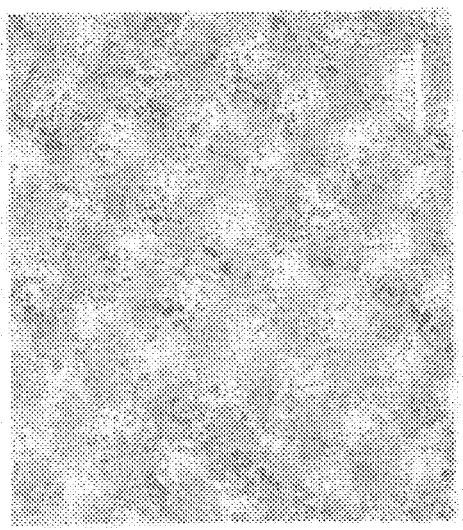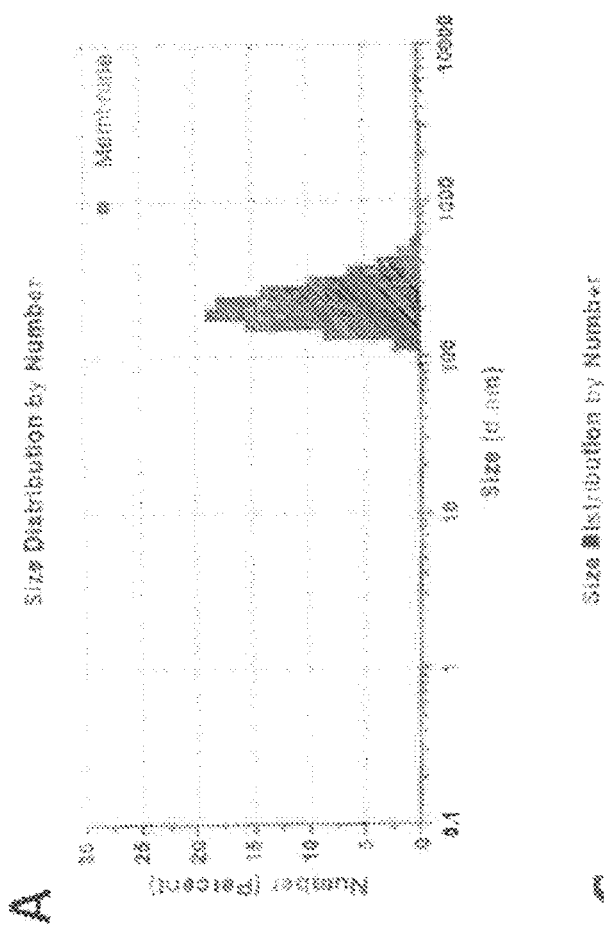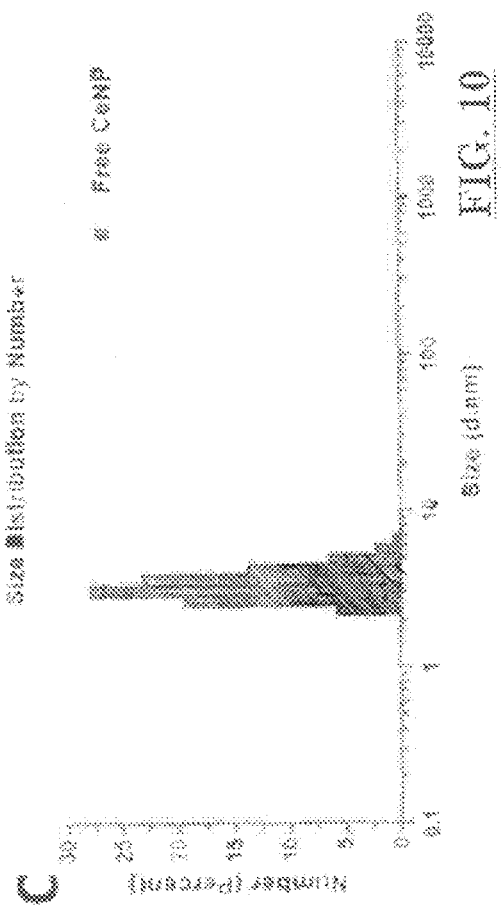
FIG. 10

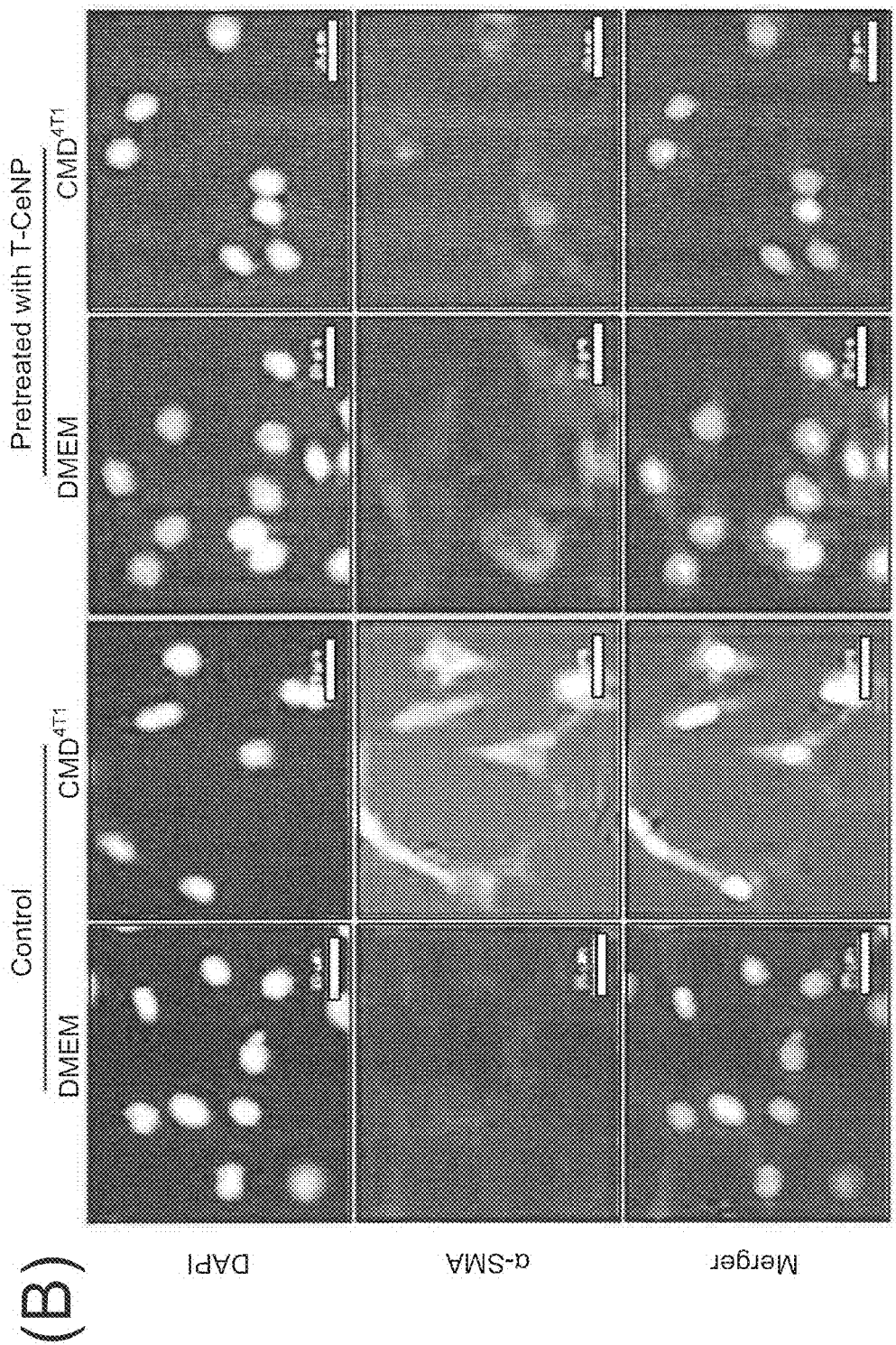
FIG. 13 (CON'T)

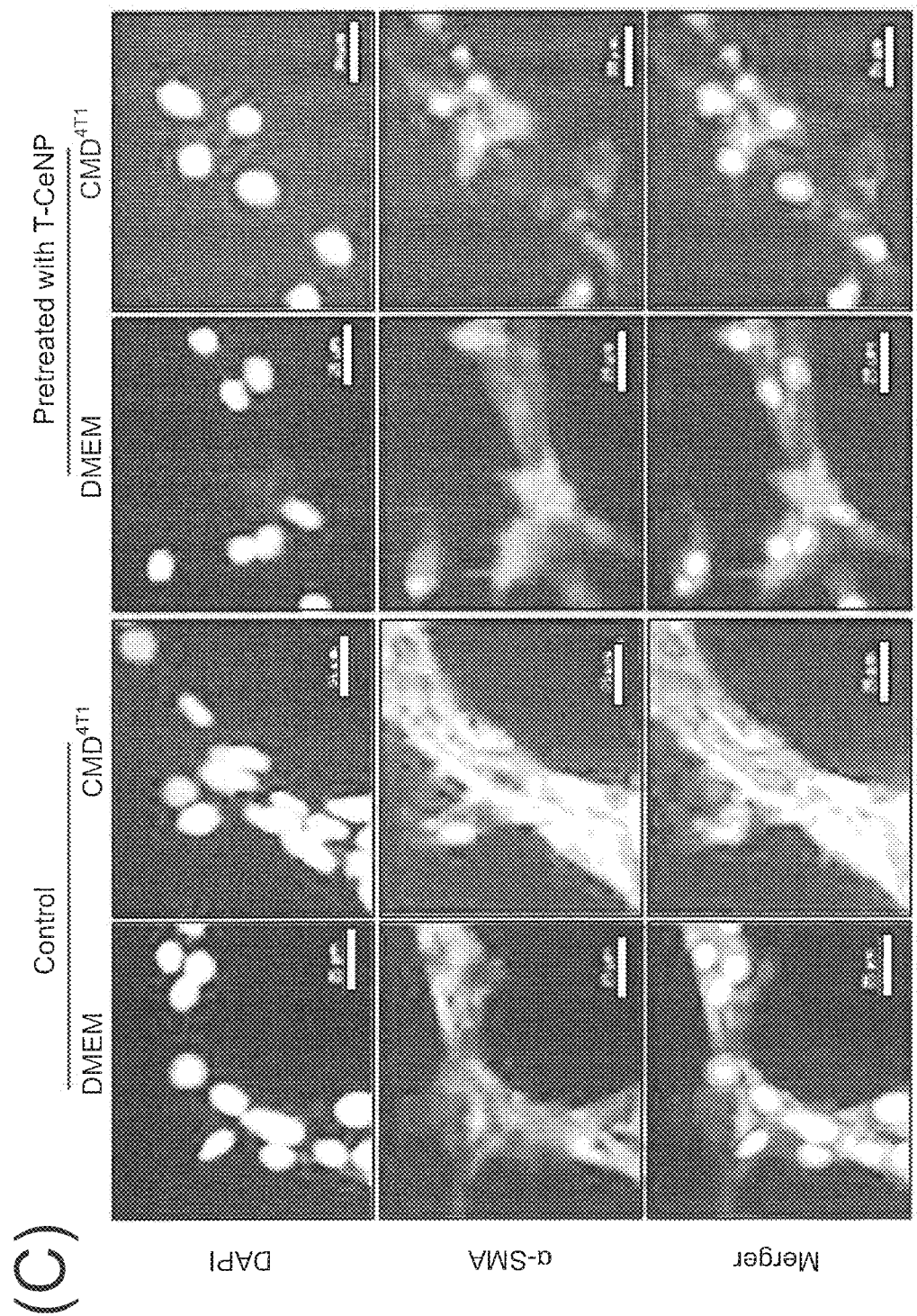
FIG. 13 (CON'T)

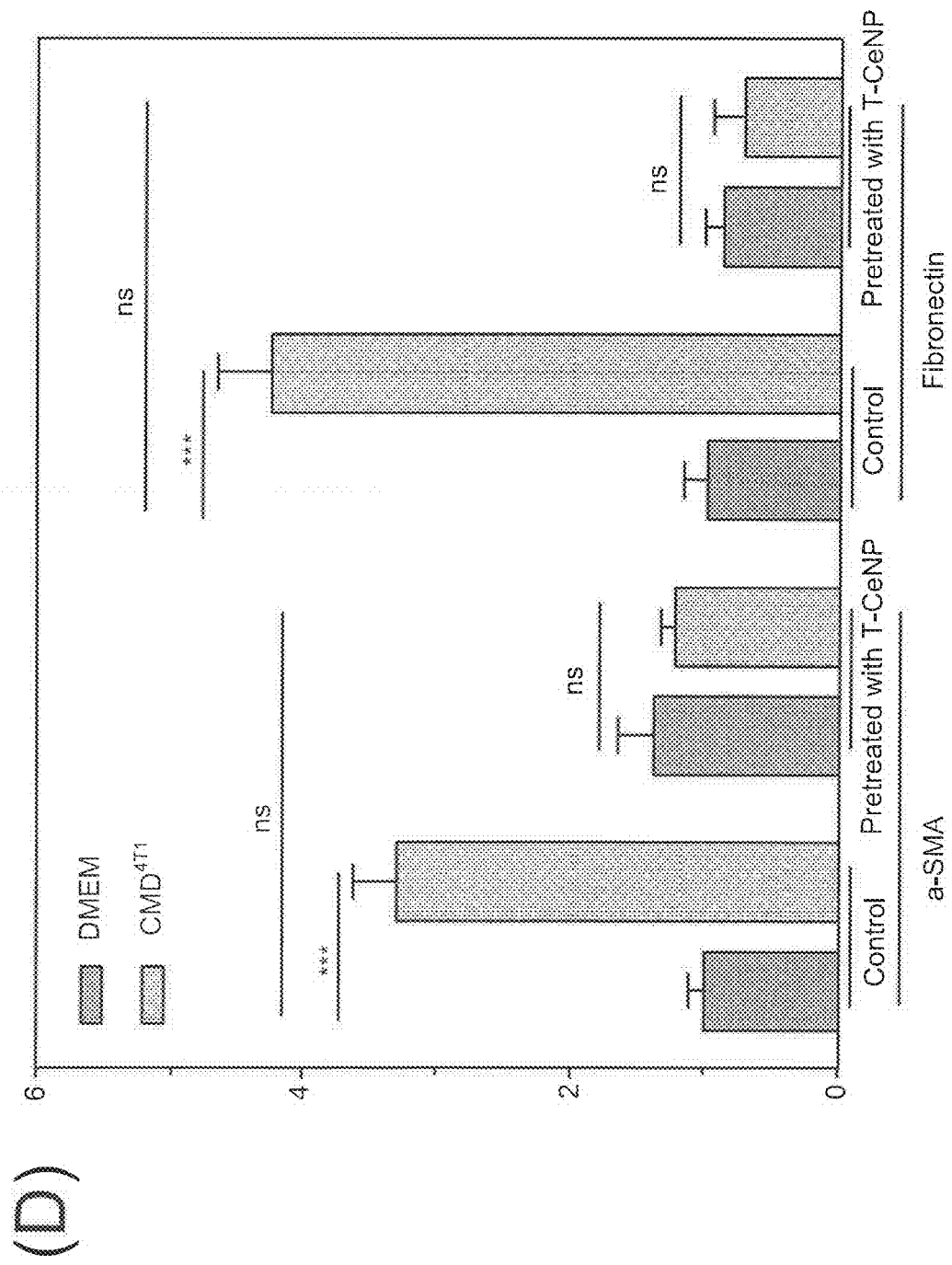
FIG. 13 (CON'T)

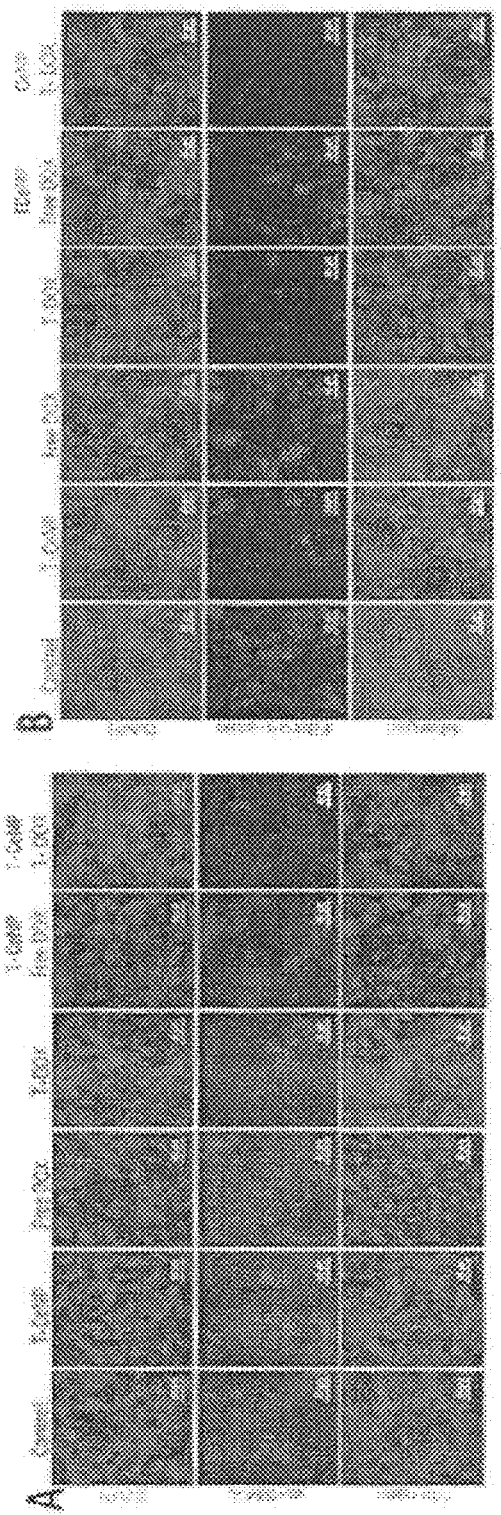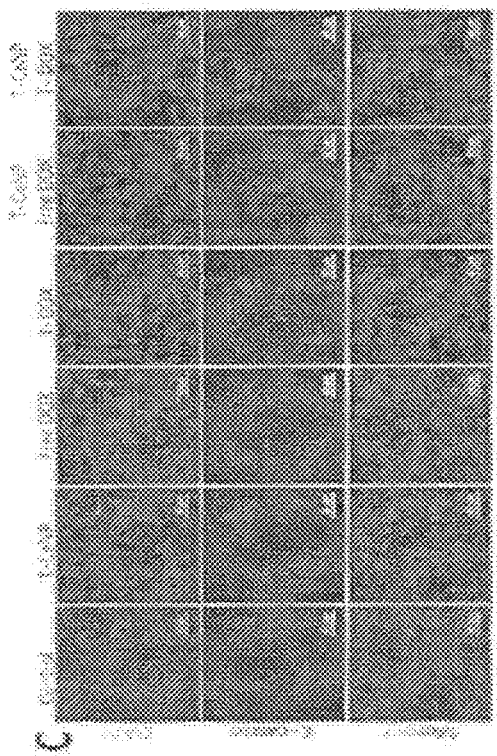
FIG. 18

NANOPARTICLE FOR THE REMODELING OF CANCER-ASSOCIATED FIBROBLASTS

STATEMENT REGARDING FEDERALLY SPONSORED RESEARCH

This disclosure was made with government support under NIH 5R01AG054839. The government has certain rights in the disclosure.

TECHNICAL FIELD

The subject matter disclosed herein is generally directed to systems and methods for employing a tumor targeted cerium oxide nanoparticle system, T-CeNP, for cancer therapy to hinder cancer associated fibroblast (CAF) transdifferentiation and reprogram CAFs back to normal fibroblasts to reduce tumor size and prevent metastasis.

BACKGROUND

Since the "seed and soil" theory was proposed by Stephen Paget in 1889, see I. J. Fidler, *Nature Reviews Cancer* 2003, that the tumor microenvironment (TME) consisted of stroma cells and extracellular matrix (ECM), this has received widespread attention. TME fosters cancer initiation, evolution, and metastasis. TME mechanically creates a niche-like protective shelter to shield tumor cells from various conventional interventions, resulting in drug resistance and subsequent therapeutic failure.

Cancer-associated fibroblast (CAF) is one of the most abundant stromal cell components in the TME and elicits critical influence on cancer progression through orchestrating the reactive stroma soil, see E. Sahai, I. Astsaturov, E. Cukierman, D. G. DeNardo, M. Egeblad, R. M. Evans, D. Fearon, F. R. Greten, S. R. Hingorani, T. Hunter, *Nature Reviews Cancer* 2020, 1. On the one hand, CAF produces and secretes large quantities of growth factors, proinflammatory cytokines, and chemokines, including transforming growth factor β (TGFβ), vascular endothelial growth factor (VEGF), platelet-derived growth factor (PDGF), interleukin-6 (IL-6), and so on, see R. Kalluri, M. Zeisberg, *Nature Reviews Cancer* 2006, thus affecting and favoring the tumor progression and malignancy via paracrine signaling. On the other hand, CAF is of high capability for ECM synthesis and its dynamic remodeling, termed as desmoplasia.

In the process of desmoplasia, CAF synthesizes diverse types of fibrillar collagens, fibronectins, hyaluronan, and laminins, and creates an integrated 3D macromolecular network surrounding tumor cells, as a dense reservoir for secreted molecules and physical barrier against drugs and immune infiltration. Simultaneously, various matrix-degrading proteases produced by CAF, such as matrix metalloproteinases (MMPs), collagenases, cathepsins, and urokinase-type plasminogen activator (uPA), directly affect the biological properties and function of ECM components, thereby maintaining a highly dynamic ECM homeostasis to promote tumor progression and metastasis. See X. Chen, E. Song, *Nature Reviews Drug Discovery* 2019.

Metastasis is responsible for 90% of cancer-related deaths. See, P. Mehlen, A. Puisieux, *Nature Reviews Cancer* 2006. Metastasis involves the dissemination of tumor cells from their primary sites and subsequent colonization in distant organs. See C. L. Chaffer, R. A. Weinberg, *Science* 2011. Acquisition of migratory/invasive phenotype and breach of the surrounding boundary in its primary location are two critical prerequisites for cancer cells' distant dissemination. All these processes are closely affected by the above-mentioned CAF dominated TME. It has been reported that, in breast cancer, cancer cells undergo a TGFβ-SMAD signaling mediated epithelial-to-mesenchymal transition (EMT) induced by CAF to acquire a highly invasive phenotype See J. C. Tse, R. Kalluri, *Journal Of Cellular Biochemistry* 2007. With the help of a group of digestive enzymes derived from CAF, paladin-expressing CAF rips and destroys the ECM to create tunnels, thus paving the way for cancer cells to escape and invade. See, T. A. Brentnall, *Cell Adhesion & Migration* 2012. Therefore, targeting the CAF is an emerging paradigm for combating primary tumors and their metastasis.

Neoadjuvant chemotherapy, also known as preoperative chemotherapy, was a recommended management for patients with large (≥3 cm) and locally advanced breast cancer to reduce primary tumor size, demarcate the outline of primary tumor for surgical resection and breast conservation, and minimize the recurrence of distant metastasis. See, J. Mieog, J. Van der Hage, C. Van De Velde, *British Journal of Surgery* 2007. However, a large-scale clinical randomized study carried out by the National Surgical Adjuvant Breast and Bowel Project (NSABP) revealed that there was no statistical difference in disease-free or overall survival between anthracycline-based neoadjuvant chemotherapy and adjuvant chemotherapy, except increasing the likelihood of breast conservation. See, B. Fisher, J. Bryant, N. Wolmark, E. Mamounas, A. Brown, E. R. Fisher, D. L. Wickerham, M. Begovic, A. DeCillis, A. Robidoux, *Journal Of Clinical Oncology* 1998. One reason for this paradox is that breast cancer cells may possess intrinsic or developed resistance to the neoadjuvant chemotherapeutic agent. See, I. F. Faneyte, P. M. Kristel, M. Maliepaard, G. L. Scheffer, R. J. Scheper, J. H. Schellens, M. J. van de Vijver, *Clinical Cancer Research* 2002, 8, 1068; A. M. Gonzalez-Angulo, F. Morales-Vasquez, G. N. Hortobagyi, in *Breast Cancer Chemosensitivity*, Springer, 2007, 1; X. Li, M. T. Lewis, J. Huang, C. Gutierrez, C. K. Osborne, M.-F. Wu, S. G. Hilsenbeck, A. Pavlick, X. Zhang, G. C. Chamness, *Journal of the National Cancer Institute* 2008. Another possibility is that adjuvant chemotherapy might exasperate quiescent cancer cells and perturb TME, such as incepting CAF-induced high expression of high mobility group box 1 (HMGB1) associated resistance in breast cancer, see K. Amornsupak, T. Insawang, P. Thuwajit, O. Pornchai, S. A. Eccles, C. Thuwajit, *BMC Cancer* 2014, 14, 1, increasing the density and activity of tumor microenvironment at the metastasis sites, see G. S. Karagiannis, J. M. Pastoriza, Y. Wang, A. S. Harney, D. Entenberg, J. Pignatelli, V. P. Sharma, E. A. Xue, E. Cheng, T. M. D'Alfonso, *Science Translational Medicine* 2017, which subsequently increases the risk of metastatic dissemination and compromise the benefit of neoadjuvant chemotherapy. See, G. S. Karagiannis, J. M. Pastoriza, Y. Wang, A. S. Harney, D. Entenberg, J. Pignatelli, V. P. Sharma, E. A. Xue, E. Cheng, T. M. D'Alfonso, *Science Translational Medicine* 2017 and A. DeMichele, D. Yee, L. Esserman, *New England Journal of Medicine* 2017, 377, 2287; I. Keklikoglou, C. Cianciaruso, E. Güç, M. L. Squadrito, L. M. Spring, S. Tazzyman, L. Lambein, A. Poissonnier, G. B. Ferraro, C. Baer, *Nature Cell Biology* 2019.

Accordingly, it is an object of the present disclosure to provide a neoadjuvant chemotherapeutic agent that can not only restore cancer cells chemosensitivity but simultaneously prime TME would maximize the benefit of neoadjuvant chemotherapy.

Citation or identification of any document in this application is not an admission that such a document is available as prior art to the present disclosure.

SUMMARY

The above objectives are accomplished according to the present disclosure by providing an anti-cancer drug. The anti-cancer drug may include at least one biomimetic nanoparticle integrated with at least one biodegradable dendritic mesoporous nanoparticle and at least one camouflage coating substantially covering the at least one biomimetic nanoparticle integrated with the at least one biodegradable dendritic mesoporous nanoparticle. Further, the at least one biomimetic nanoparticle may comprise at least one cerium oxide nanoparticle. Yet again, the at least one biodegradable dendritic mesoporous nanoparticle may include silica to form at least one biodegradable dendritic mesoporous organosilica nanoparticle. Again, the at least one biomimetic nanoparticle may prevent at least one fibroblast undergoing TGFβ-induced ROS-dependent transdifferentiation to form at least one myofibroblast. Still yet again, the at least one biomimetic nanoparticle may cause reverse transdifferentiation of at least one cancer-associated fibroblast to at least one fibroblast. Still moreover, the at least one camouflage coating may comprise at least one homologous cell membrane. Further yet, the at least one homologous cell membrane may be formed from at least one breast cancer cell. Moreover, the at least one homologous cell membrane may include at least one membrane protein from the at least one breast cancer cell, wherein the at least one membrane protein may retain its adhesion protein function. Still yet, the at least one camouflage coating may substantially cover the at least one biomimetic nanoparticle integrated with the at least one biodegradable dendritic mesoporous nanoparticle is introduced to a subject followed by exposing the subject to doxorubicin.

In a further embodiment, the disclosure may provide a method for preventing post-surgery metastasis of breast cancer. The method may include introducing at least one biomimetic nanoparticle integrated with at least one biodegradable dendritic mesoporous nanoparticle, with at least one camouflage coating substantially covering the at least one biomimetic nanoparticle integrated with the at least one biodegradable dendritic mesoporous nanoparticle, to a subject, subsequently introducing doxorubicin to the subject, and inhibiting, via the at least one biomimetic nanoparticle integrated with at least one biodegradable dendritic mesoporous nanoparticle having at least one camouflage coating, cancer-associated fibroblast transdifferentiation and/or promoting cancer-associated fibroblast reprogramming through reverse transdifferentiation from cancer-associated fibroblast to fibroblast in the subject. Further, the at least one biomimetic nanoparticle may comprise at least one cerium oxide nanoparticle. Still further, the at least one biodegradable dendritic mesoporous nanoparticle may comprise silica to form at least one biodegradable dendritic mesoporous organosilica nanoparticle. Yet further, the at least one biomimetic nanoparticle may prevent at least one fibroblast undergoing TGFβ-induced ROS-dependent transdifferentiation to form at least one myofibroblast. Again still, the at least one biomimetic nanoparticle may cause reverse transdifferentiation of at least one cancer-associated fibroblast to at least one fibroblast. Moreover, that method may include configuring the at least one camouflage coating to comprise at least one homologous cell membrane. Still yet further, the method may include forming the at least one homologous cell membrane from at least one breast cancer cell. Further again, the method may include configuring the at least one homologous cell membrane to comprise at least one membrane protein from the at least one breast cancer cell, wherein the at least one membrane protein retains its adhesion protein function. Still moreover, the method may include configuring the at least one camouflage coating to substantially cover the at least one biomimetic nanoparticle integrated with the at least one biodegradable dendritic mesoporous nanoparticle and introducing same to a subject followed by exposing the subject to doxorubicin.

These and other aspects, objects, features, and advantages of the example embodiments will become apparent to those having ordinary skill in the art upon consideration of the following detailed description of example embodiments.

BRIEF DESCRIPTION OF THE DRAWINGS

An understanding of the features and advantages of the present disclosure will be obtained by reference to the following detailed description that sets forth illustrative embodiments, in which the principles of the disclosure may be utilized, and the accompanying drawings of which:

FIG. 3A shows anti-migration and invasion ability of T-CeNP to 4T1 cells with presented wound healing pictures at (a) of 4T1 cells treated with different types of nanoparticles at various concentrations and their quantitative analysis (b) using the Image-Pro Plus 6.0 software.

FIG. 3B shows a diagram of a transwell assay and the invaded transwell cells pictures at (c) of 4T1 cells after treated with different types of nanoparticles at various concentration and their corresponding quantitative analysis at (d)—data expressed as mean±s.d. (n=3) *$p<0.05$, $p<0.01$, and *$p<0.001$.

and fibronectin (f) expression in (e) and (f) using the Image-Pro Plus 6.0—data expressed as mean±s.d. (n=3), and ***p<0.001.

Figure 5A:
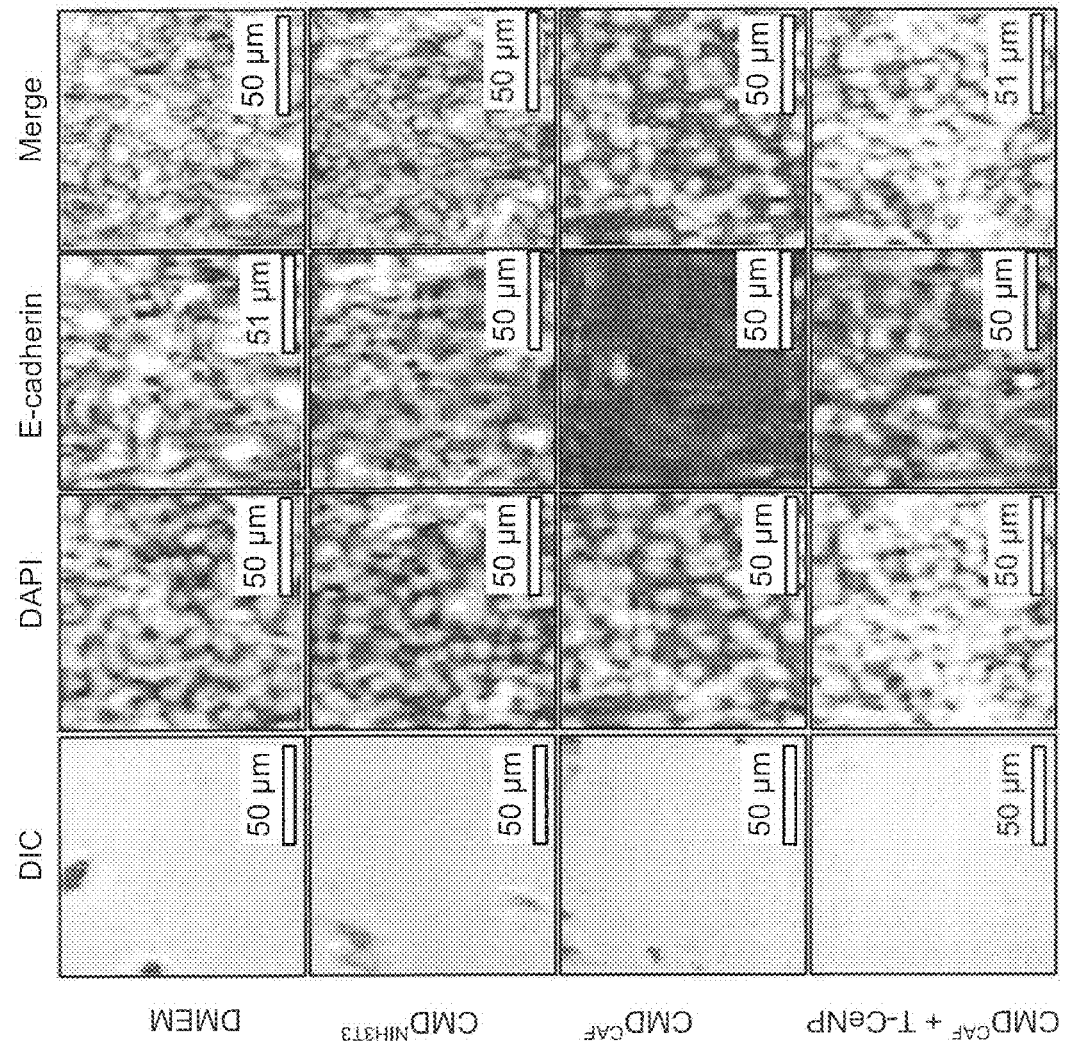

FIG. 5A shows inhabitation effect of T-CeNP on migration, invasion, and EMT of 4T1 cells at (a) the immunofluorescence of e-cadherin on 4T1 cells after incubation with different condition media; and (b) immunofluorescence of e-cadherin on 4T1 cells and T-CeNP pretreated 4T1 cells after incubation with different CMDs; (c) quantitative analysis of secretion of TGF-β by NIH3T3 cells and CAF after different treatments by using TGF-β ELIAS kit; (d) the presented wound healing images of 4T1 cells after treated with different CMDs for 48 and 96 hours. The represented Transwell cells images at (e) of 4T1 cells after treated with different kind of CMDs and their corresponding quantitative analysis at (f).

FIG. 5B shows immunofluorescence of e-cadherin on 4T1 cells at (g) and fibronectin secreted by fibroblast at (h) in the co-culture model of NIH3T3 and 4T1 cells after treated with T-CeNP—data expressed as mean±s.d. (n=3), *p<0.05, p<0.01, and *p<0.001.

Figure 6B:
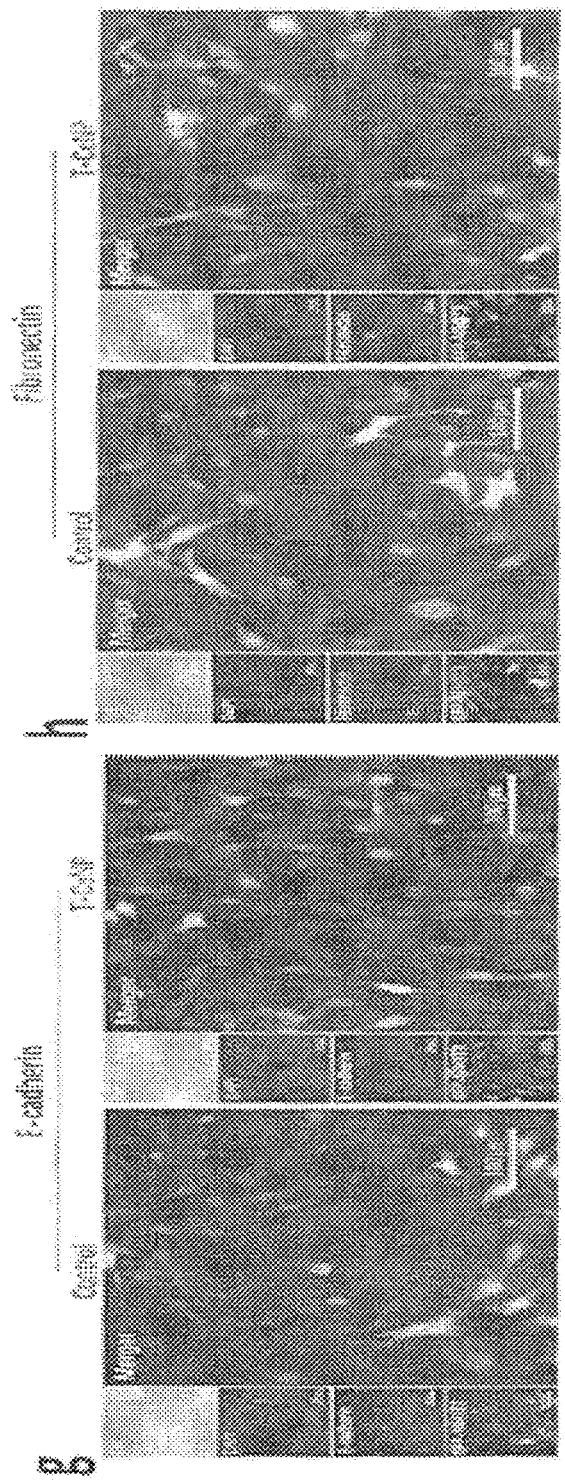
Figure 6A:
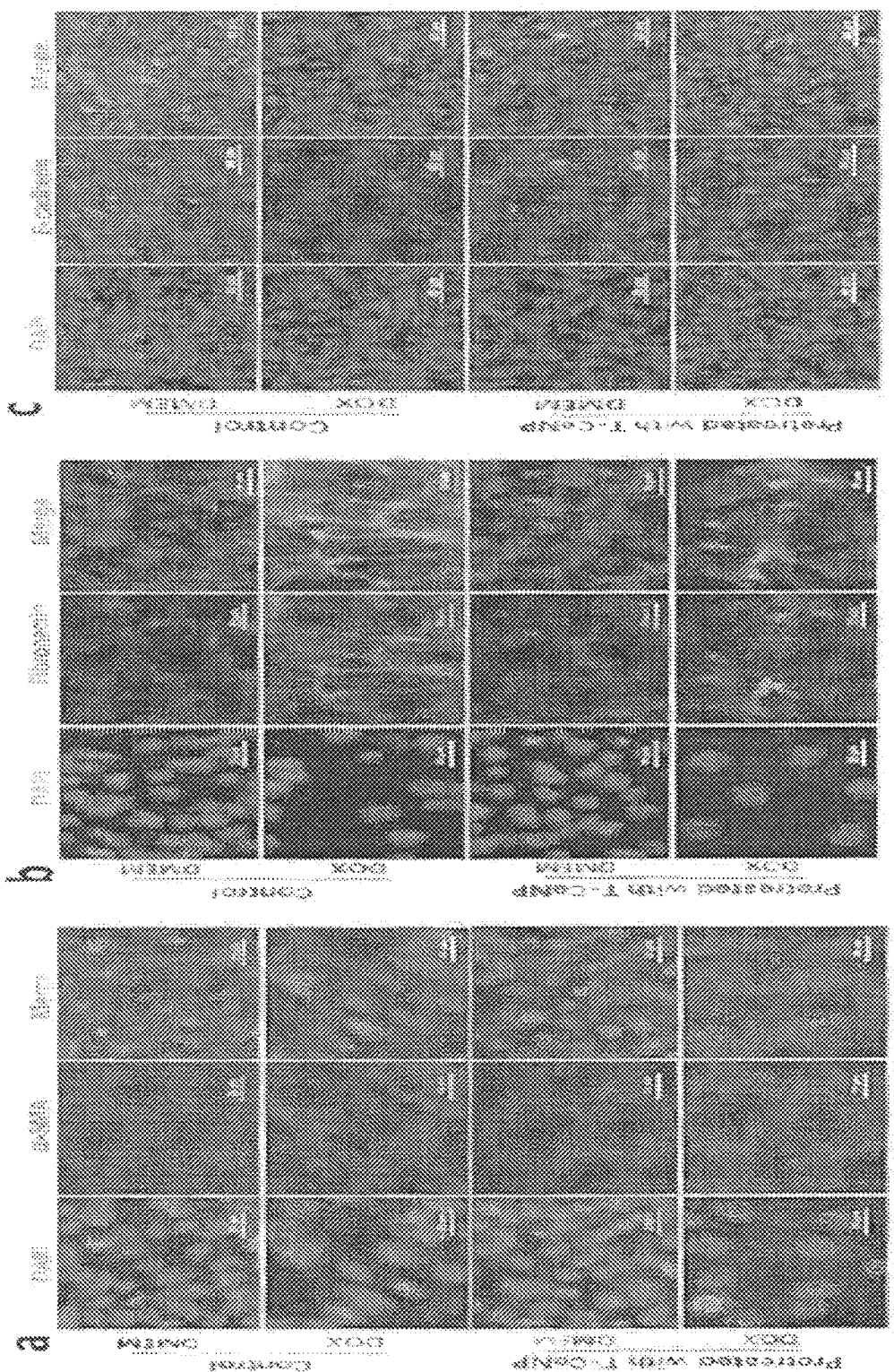
Figure 6B:
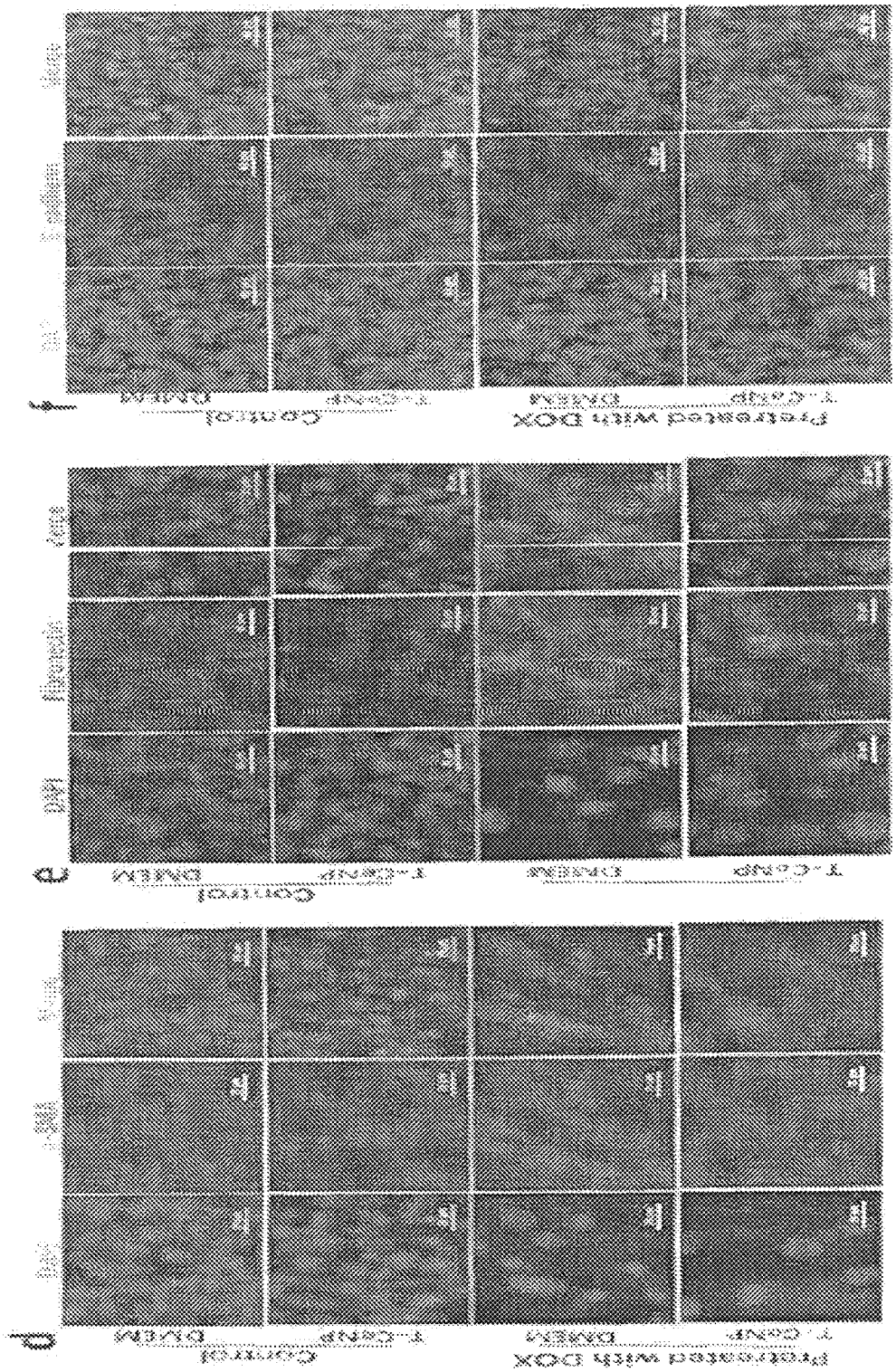

FIG. 6A shows inhabitation effect of T-CeNP on DOX induced cancer associated fibroblasts differentiation and EMT. Immunofluorescence images of: (a) α-SMA and (b) fibronectin expression in NIH3T3 cells pretreated with 100 μM of T-CeNP or not after incubation with 0.05 μM of free DOX for 48 hours; and (c) immunofluorescence images of e-cadherin expression in 4T1 cells pretreated with 100 μM of T-CeNP or not after incubation with 0.05 μM of free DOX for 48 hours.

FIG. 6B shows at (d) α-SMA; (e) fibronectin expression in NIH3T3 cells pretreated with 0.05 μM of free DOX or not after incubation with 100 μM of T-CeNP for 48 hours; and (f) immunofluorescence images of e-cadherin expression in 4T1 cells pretreated with 0.05 μM of free DOX or not after incubation with 100 μM of T-CeNP for 48 hours.

Figure 7:
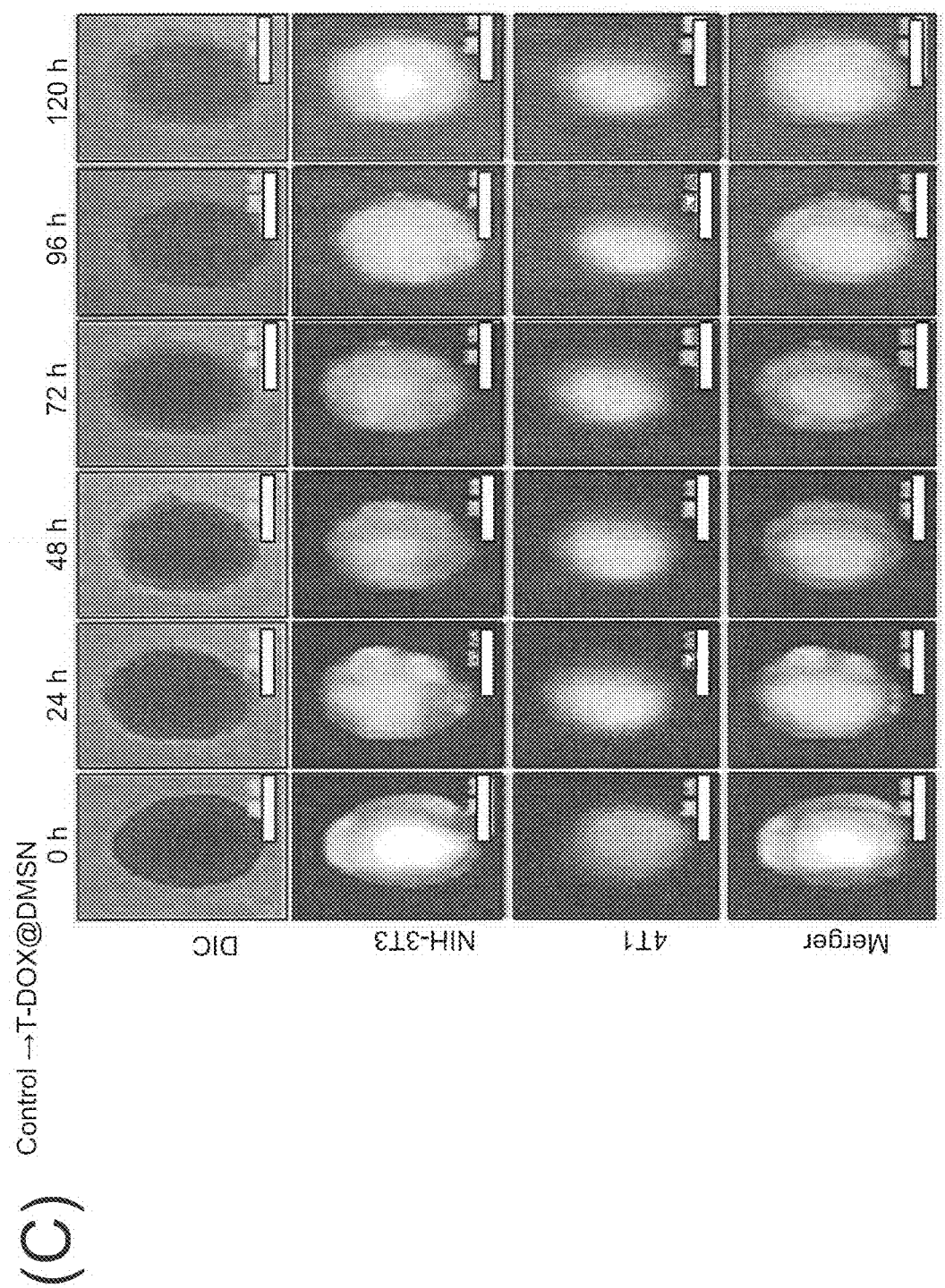
Figure 7:
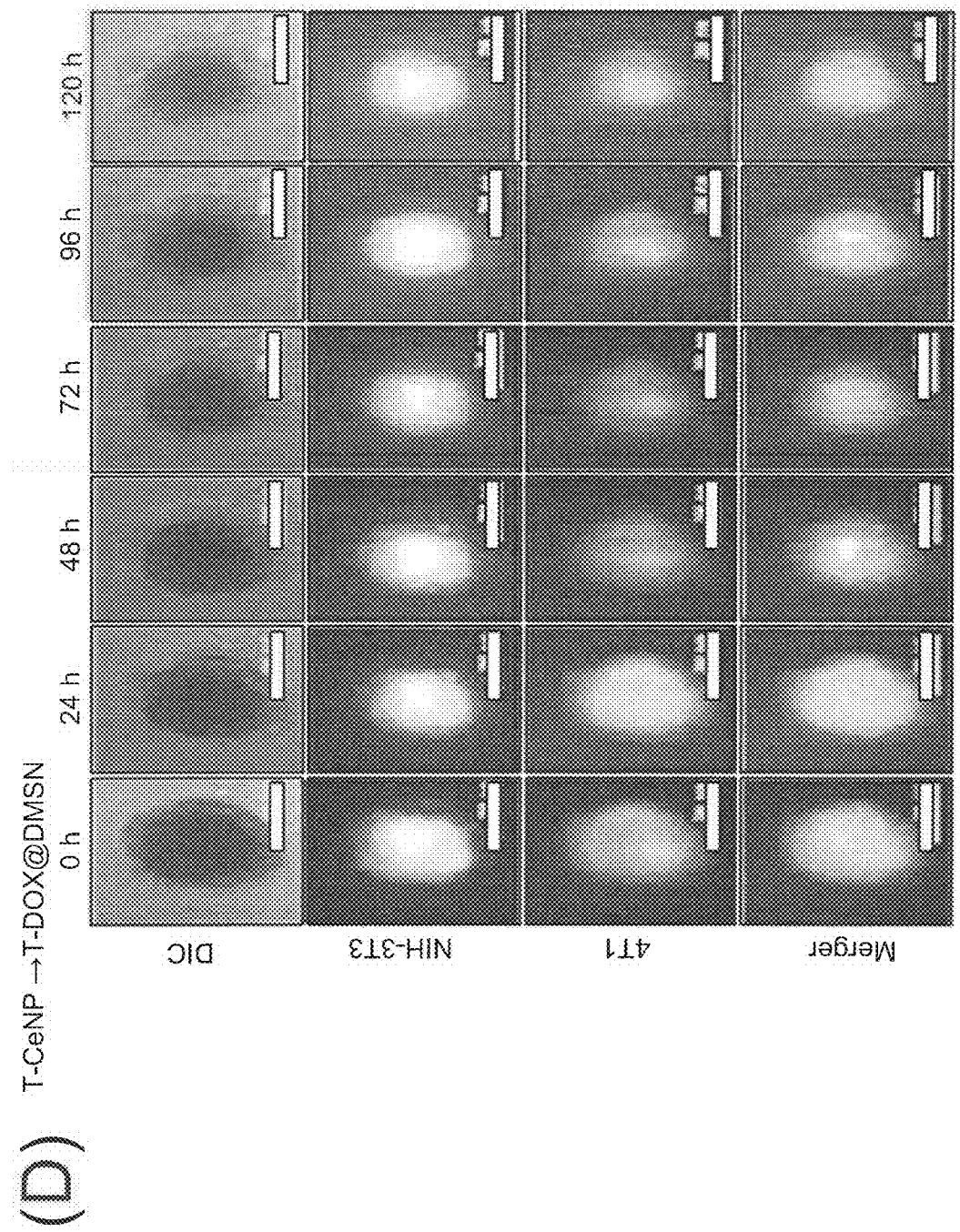

FIG. 7 shows the influence of T-CeNP on 3D co-culture tumor spheroid of NIH3T3 cells and 4T1 cells (Green: GFP expressed NIH3T3 cells; Red: cell tracker deep red labeled 4T1 cells).

Figure 8A:
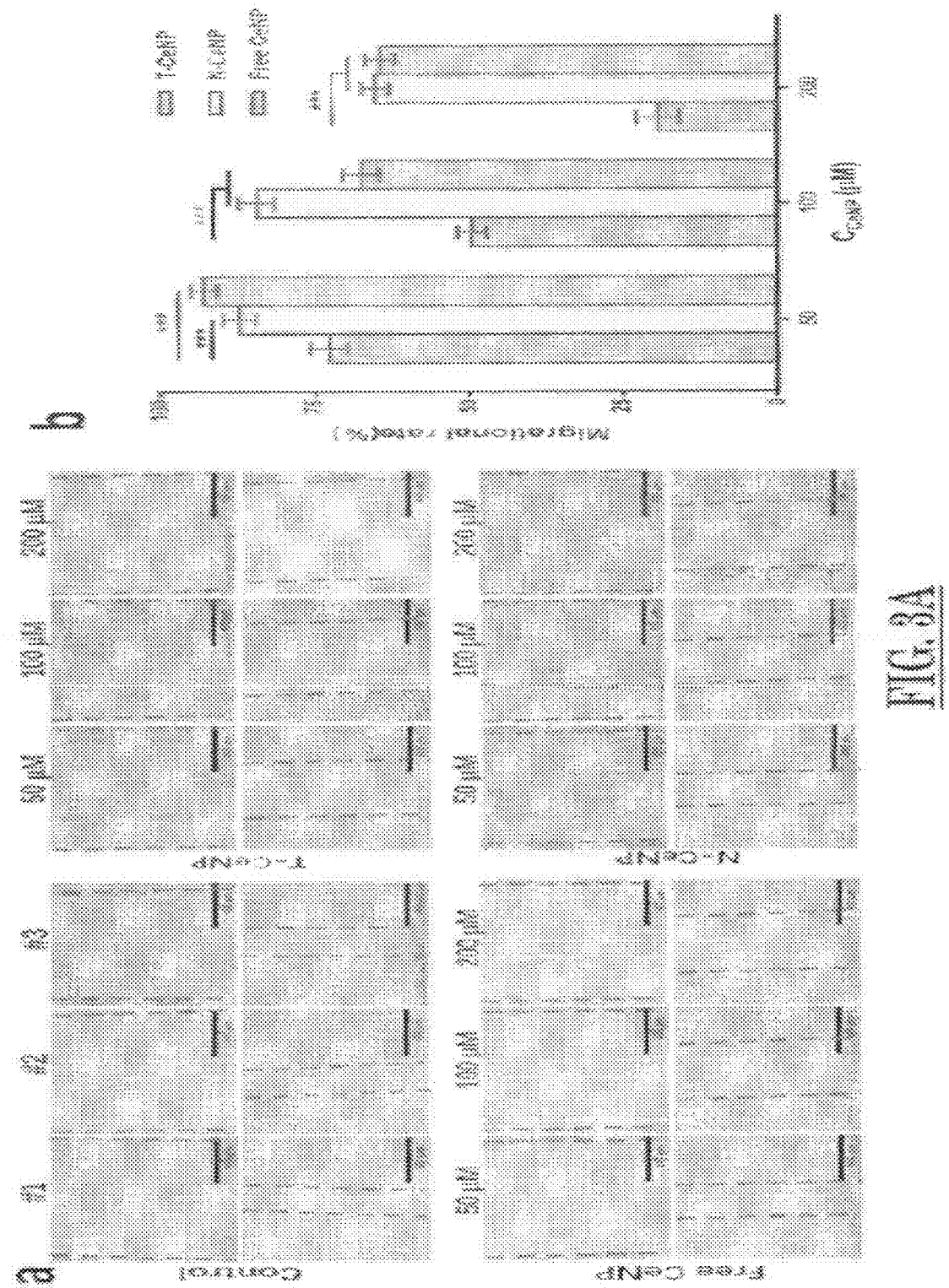
Figure 8:
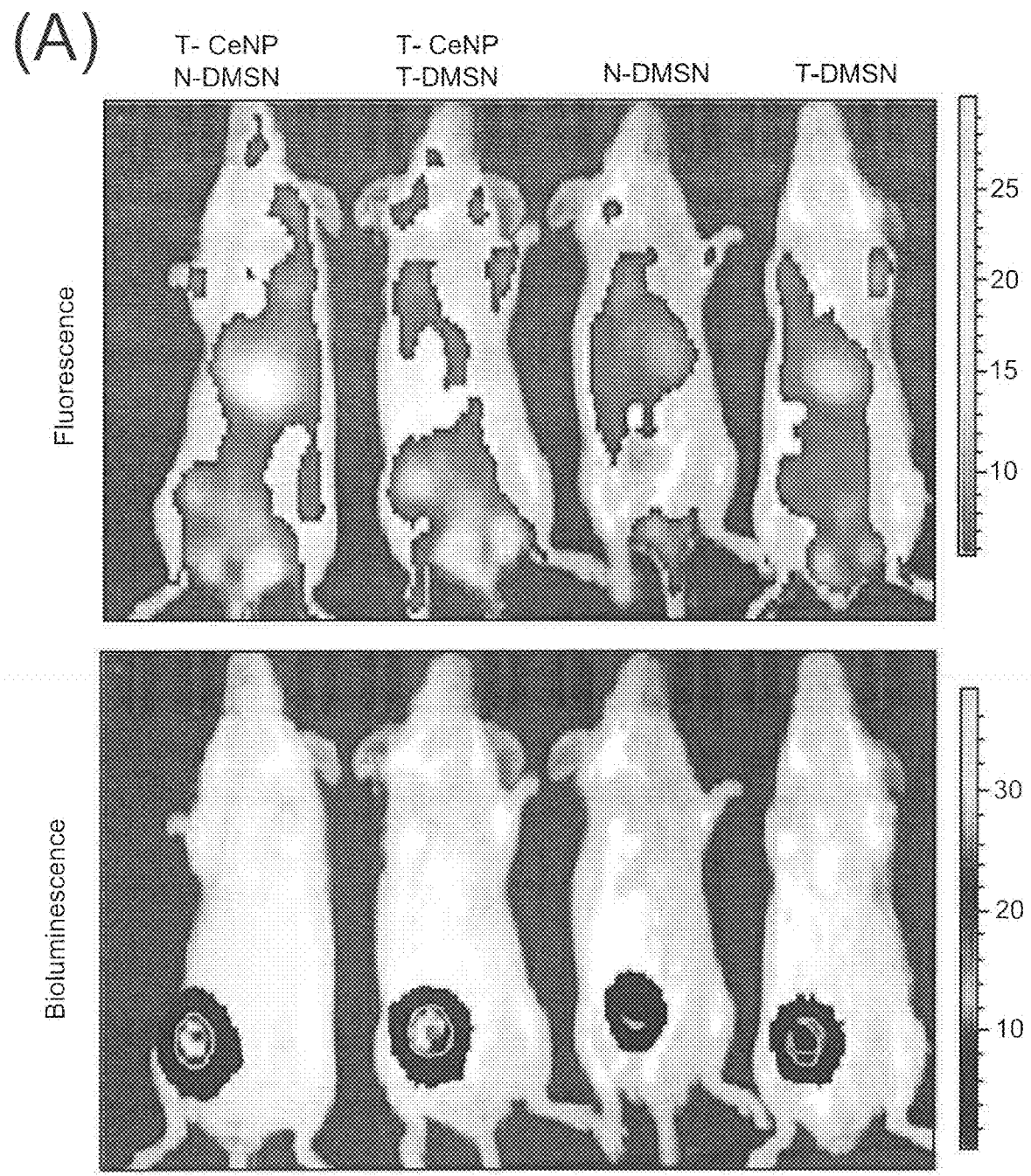

FIG. 8 shows improved distribution and penetration of nanoparticles and free DOX in orthotopic 4T1 tumors after pretreating with T-CeNP@DMSN; in vivo (a) and ex vivo (b) fluorescence imaging of Cy 5 labeled T-DMSN and N-DMSN distribution in tumor with or without T-CeNP pretreatment; (c) fluorescence images of Cy 5 labeled T-DMSN and N-DMSN in tumor frozen section responding to (b); (d) quantitative analysis of free DOX distribution in the tumor pretreated with T-CeNP or not after surgical; (e) ex vivo fluorescence imaging of Cy 5 labeled T-DMSN and N-DMSN distribution in experimental lung metastasis model of breast cancer; (f) Fluorescence imaging of Cy 5 labeled T-DMSN and N-DMSN distribution in lung frozen section—data were expressed as mean±s.d. (n=7), and ***p<0.001.

Figure 9B:
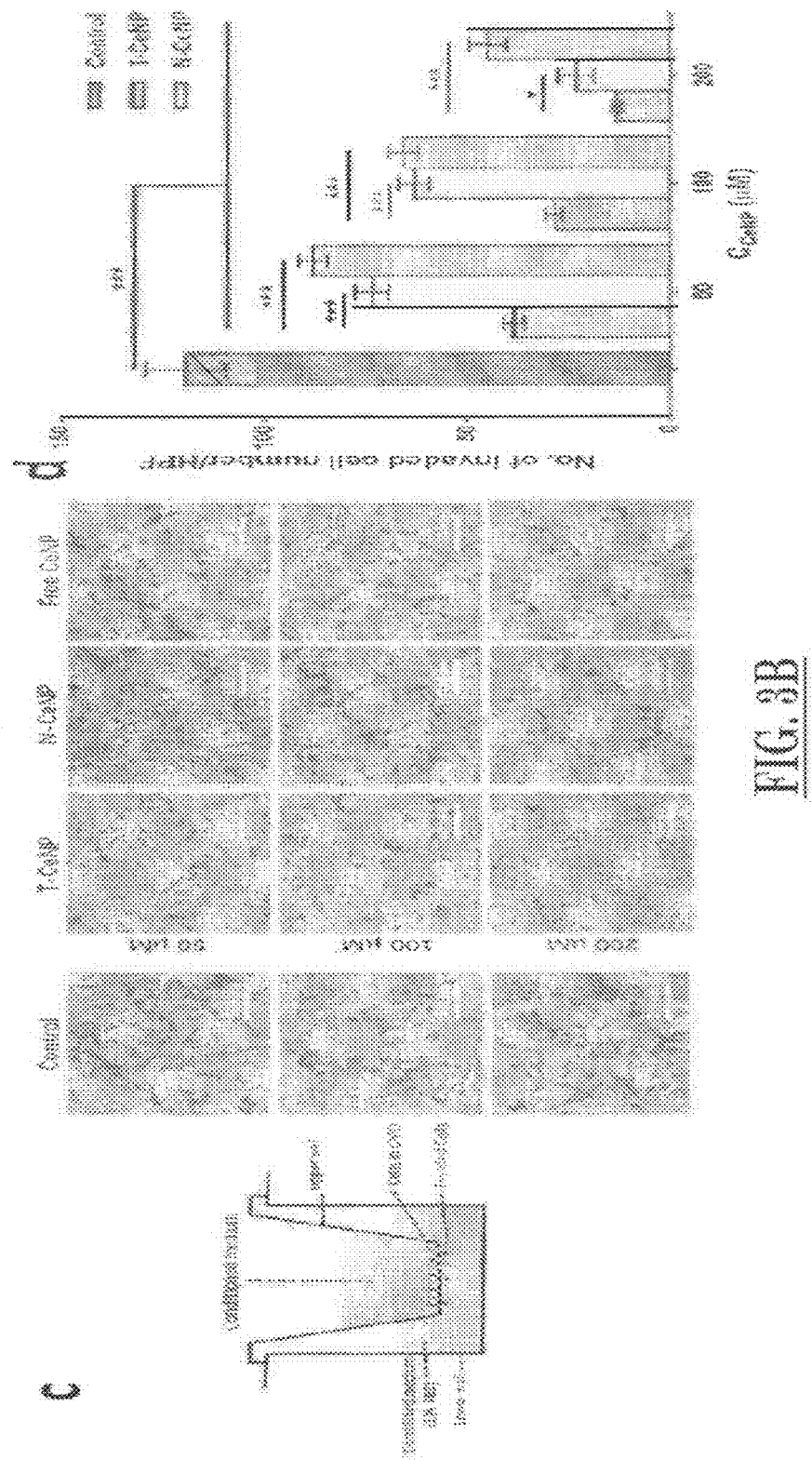
Figure 9A:
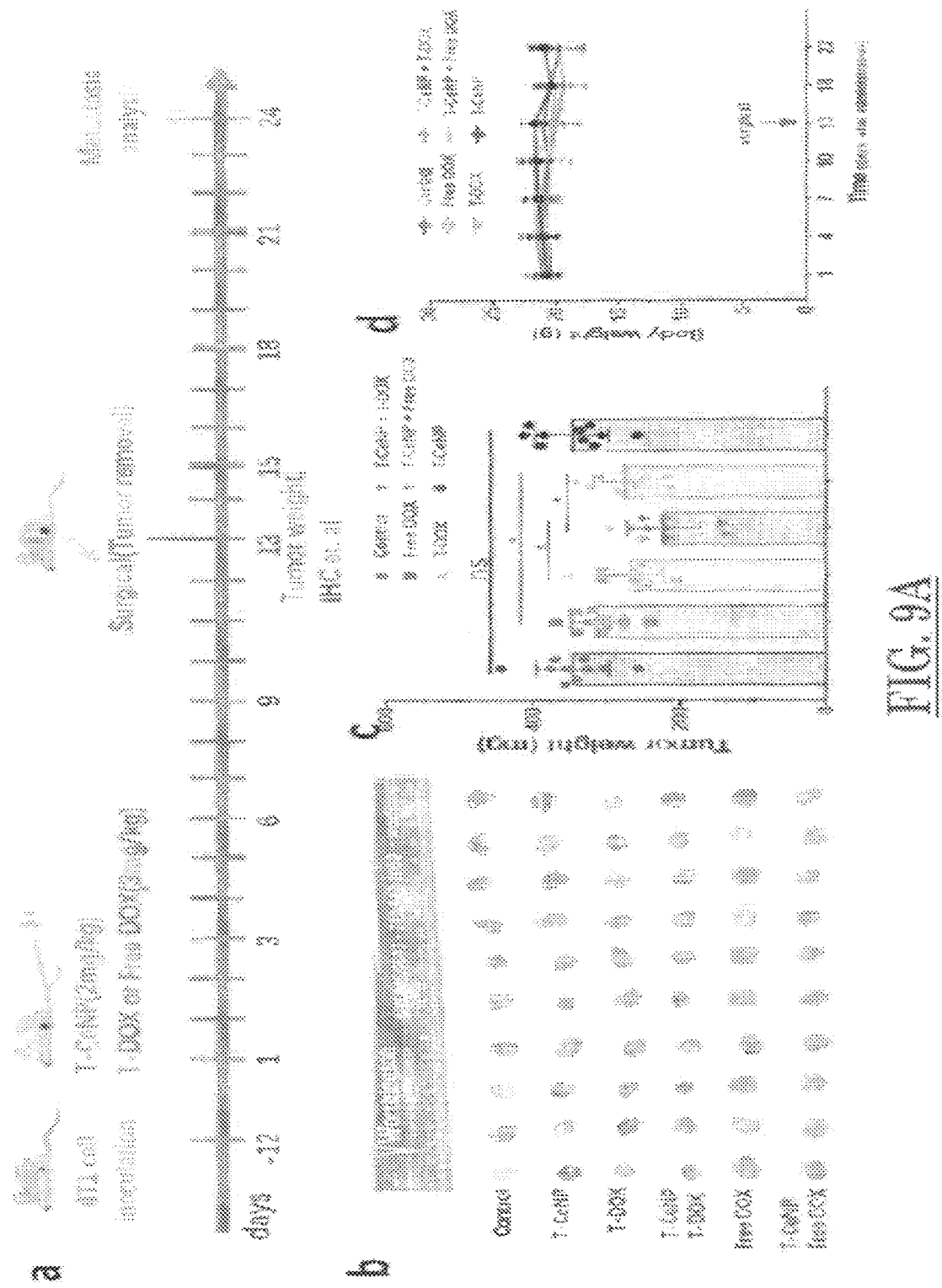
Figure 9B:
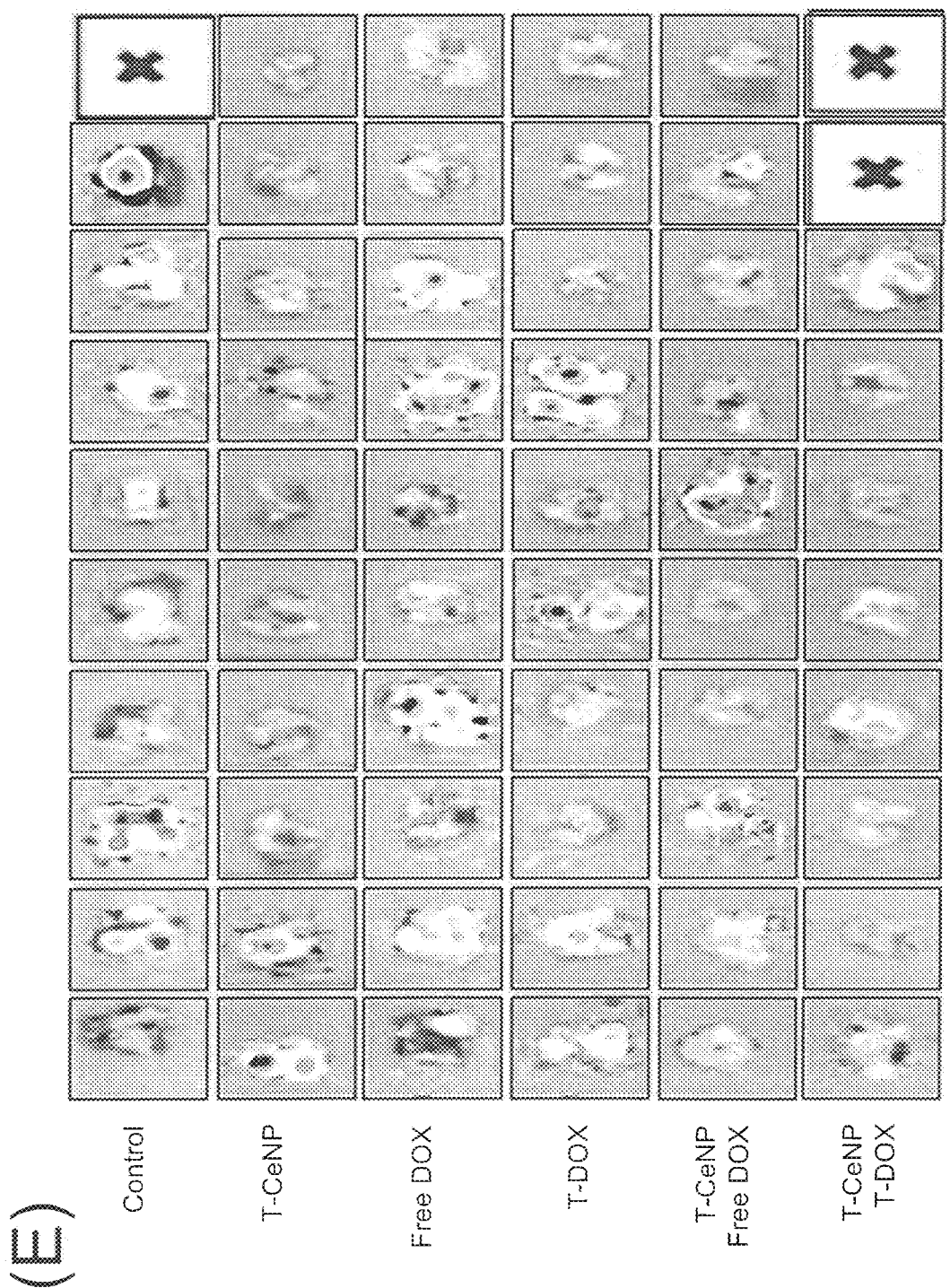

FIG. 9A shows T-CeNP as a neoadjuvant chemotherapy agent for orthotopic breast cancer at: (a) time schedule of drug administration, surgical and therapeutic evaluation; (b) Photographs of excised tumor in different treatment regimens after surgery on day 13; (c) Tumor weight obtained on day 13; and (d) Mice body weight during the treatment.

FIG. 9B shows ex vivo bioluminescence imaging for micro-metastasis in the lung (e) and the liver (f) on the last day (day 24)—the red X stands for the animal died in the tumor removal surgery; (g) heat map of micro-metastasis frequency in the liver. Representative photograph of lung surface metastasis (h) and quantitative analysis (i) metastasis nodules on the surface of lung; (j) Representative images of metastasis nodules inside the lung using H&E staining—data were expressed as mean±s.d. n=10 for panels c, and G. n=8-10 for panels c, d and i. *p<0.05, p<0.01, and *p<0.001.

FIG. 10 shows at: (A) the DLS size of cell membrane nanoparticle; (B) the protein analysis of cell membrane$^{CT26}$, DMSN and membrane$^{CT26}$ coated DMSN by SDS-PAGE; the DLS size (C) and (D) TEM image of free CeNP.

Figure 11:
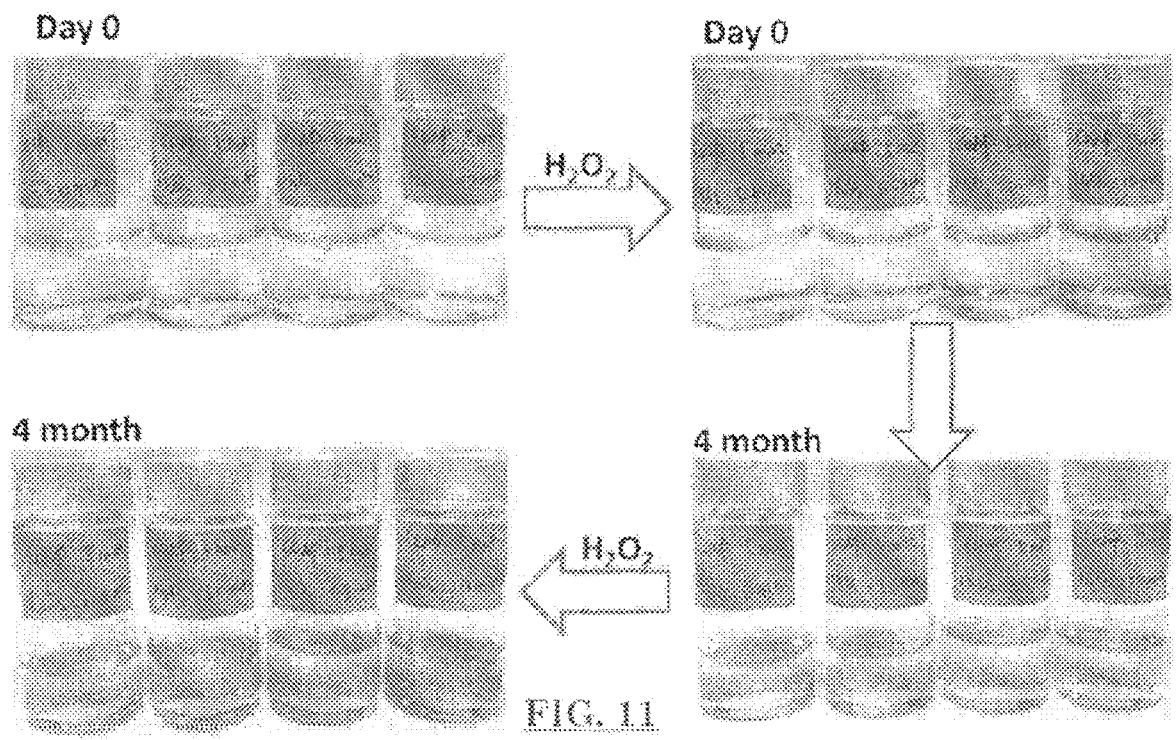

FIG. 11 shows photos of recyclable ROS scavenging capacity of ceria nanoparticle.

Figure 12:
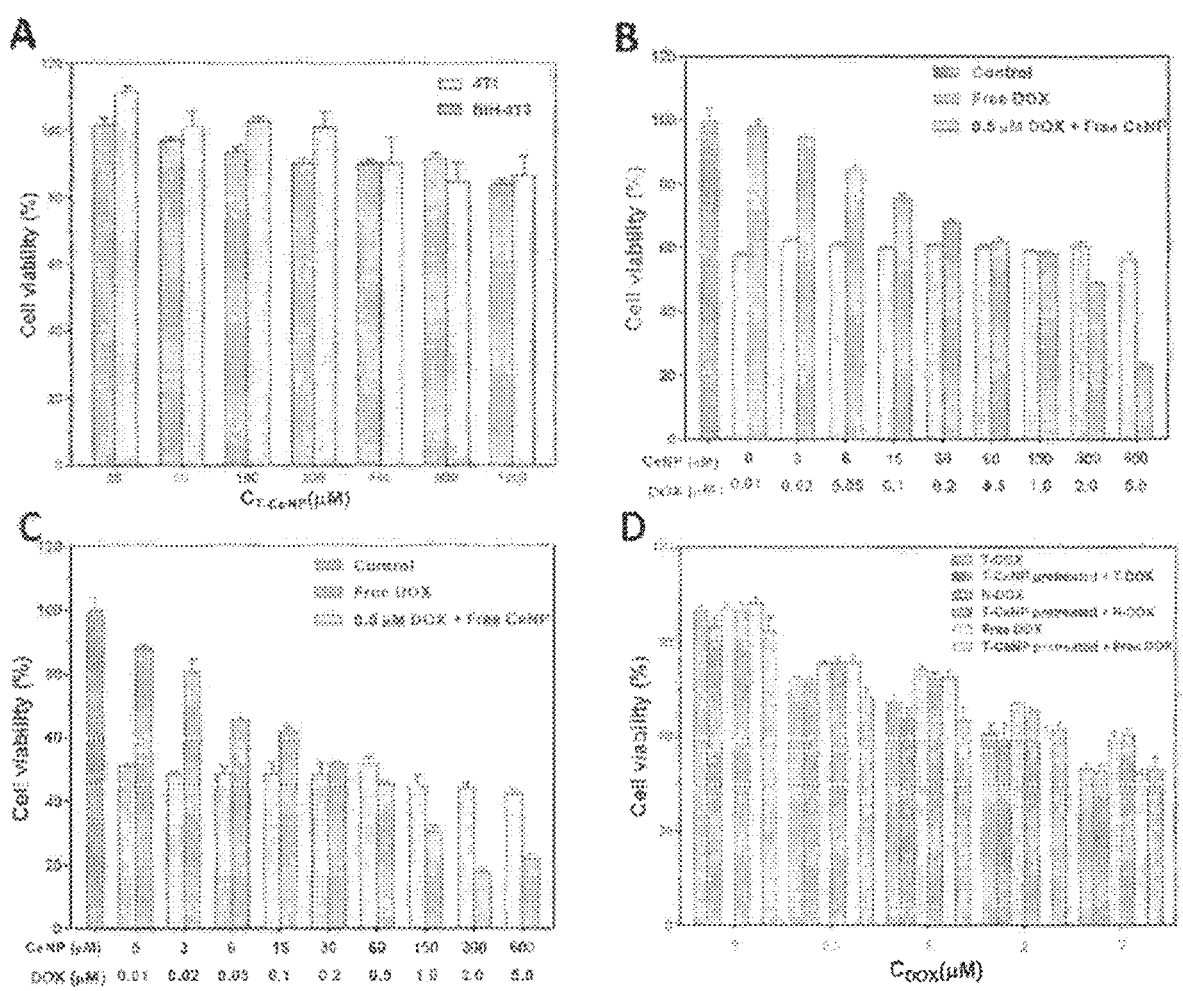

FIG. 12 shows cytotoxicity of T-CeNP and DOX to normal cells and tumor cells at: (A) cytotoxicity of T-CeNP to normal cells and tumor cells; cytotoxicity of free DOX and CeNP to NIH3T3 cells (B) and 4T1 cells (C); (D) the effect of T-CeNP pretreatment on the cytotoxicity of DOX to 4T1 cells—4T1 cells were pretreated with 100 μM T-CeNP for 12 h, followed by incubation with various concentration of free DOX, T-DOX and N-DOX for another 4 hours, after 24 hours, the cell viability was measured by MTT assay—data were expressed as mean±s.d. (n=5).

Figure 13:
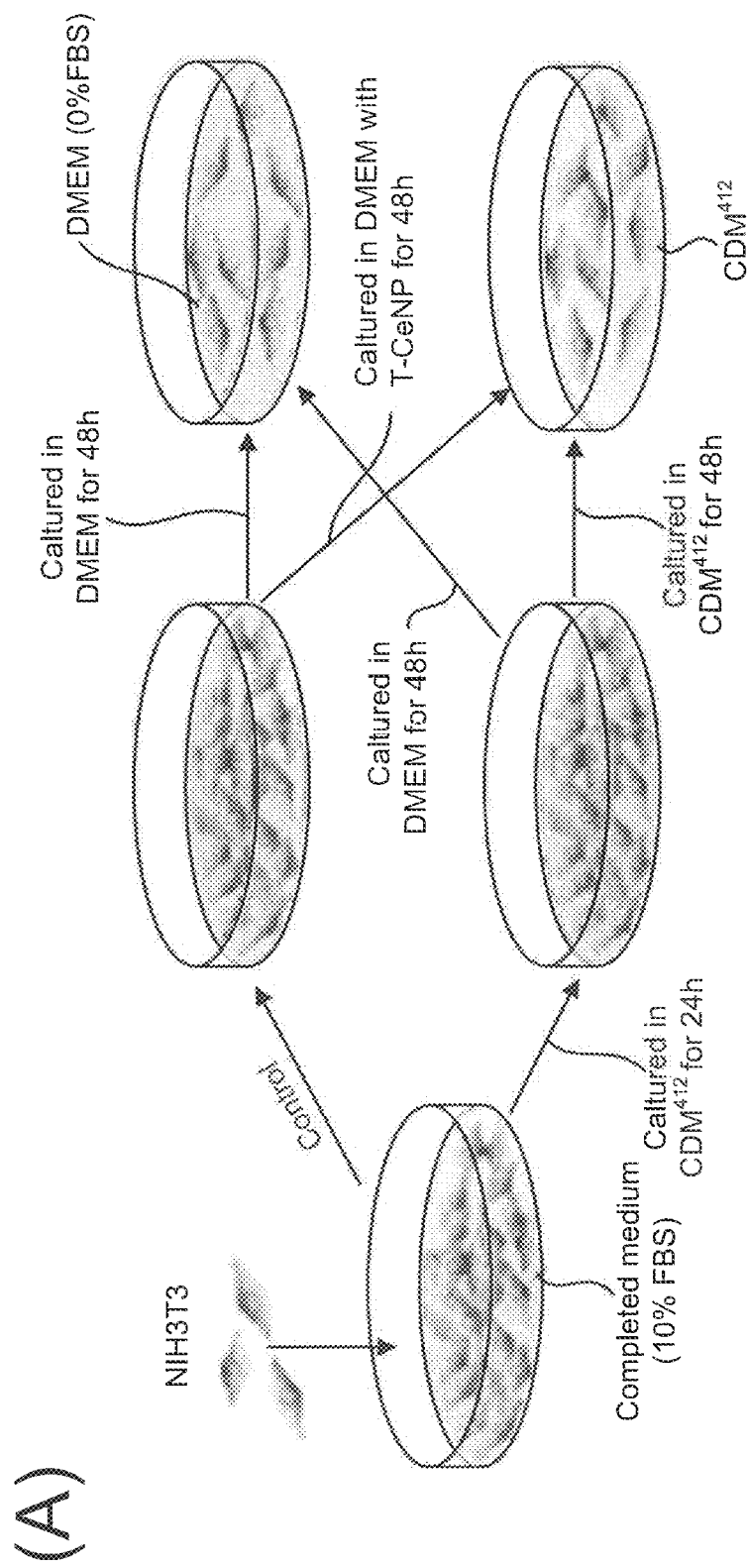

FIG. 13 shows the inhabitation effect of T-CeNP on cancer associated fibroblasts differentiation at: (A) Diagram of inhabitation effect of T-CeNP on cancer associated fibroblasts differentiation induced by CMD; (B) the secretion of TGF-β from 4T1 cells and T-CeNP pretreated 4T1 after treated with CMD$^{NIH3T3}$ and CMD$^{CAF}$ using TGF-β ELIAS kit; immunofluorescence images of α-SMA (C) and fibronectin (D) expression in NIH3T3 cells and T-CeNP pretreated NIH3T3 cells after incubation with CMD$^{4T1}$ and blank medium—data were expressed as mean±s.d. (n=3), and ***p<0.001.

Figure 14:
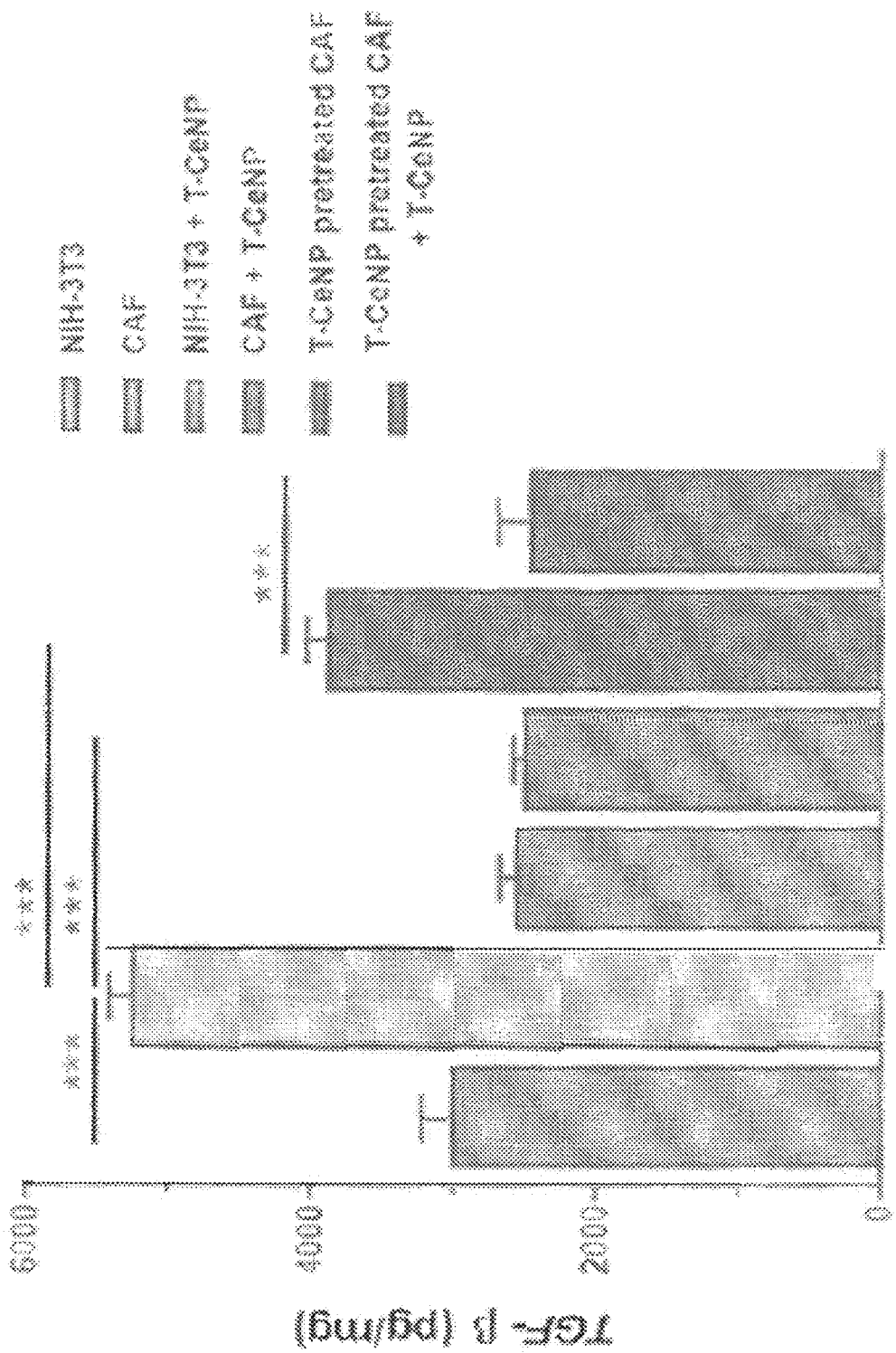

FIG. 14 shows quantitative analysis of secretion of TGF-β by NIH3T3 cells and CAF after different treatment by using TGF-β ELIAS ki—data expressed as mean±s.d. (n=3), and ***p<0.001.

Figure 15:
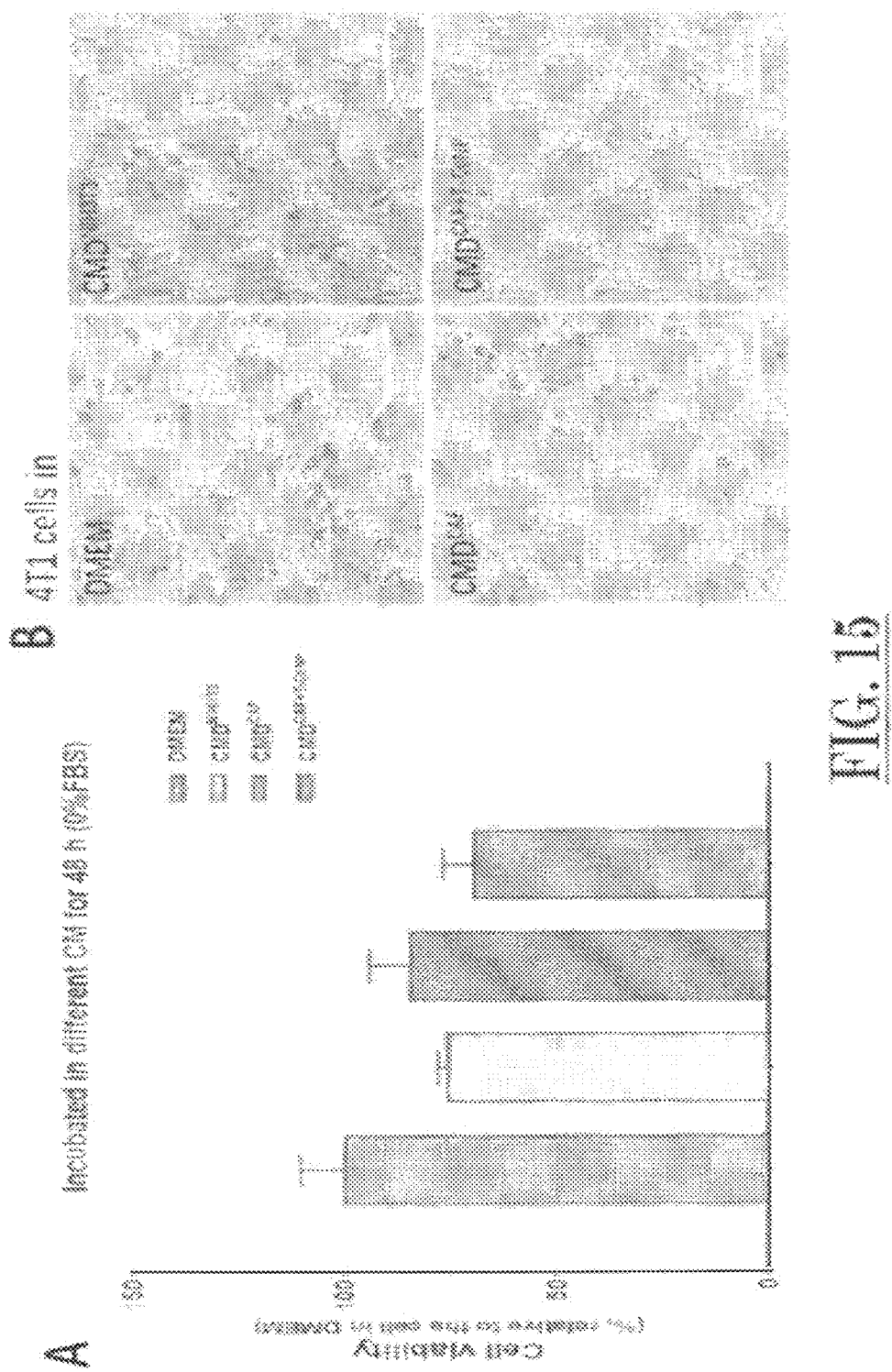

FIG. 15 shows at (A) cell viability of 4T1 cells incubated in different medium, including no FBS DMEM medium, conditioned medium of NIH-3T3 cells, conditioned medium of NIH-3T3 cells pretreated with CMD$^{4T1}$ (CAF) and conditioned medium of CAF treated with T-CeNP; and (B) a morphological photograph of 4T1 cells cultured in different medium corresponding to A.

Figure 16:
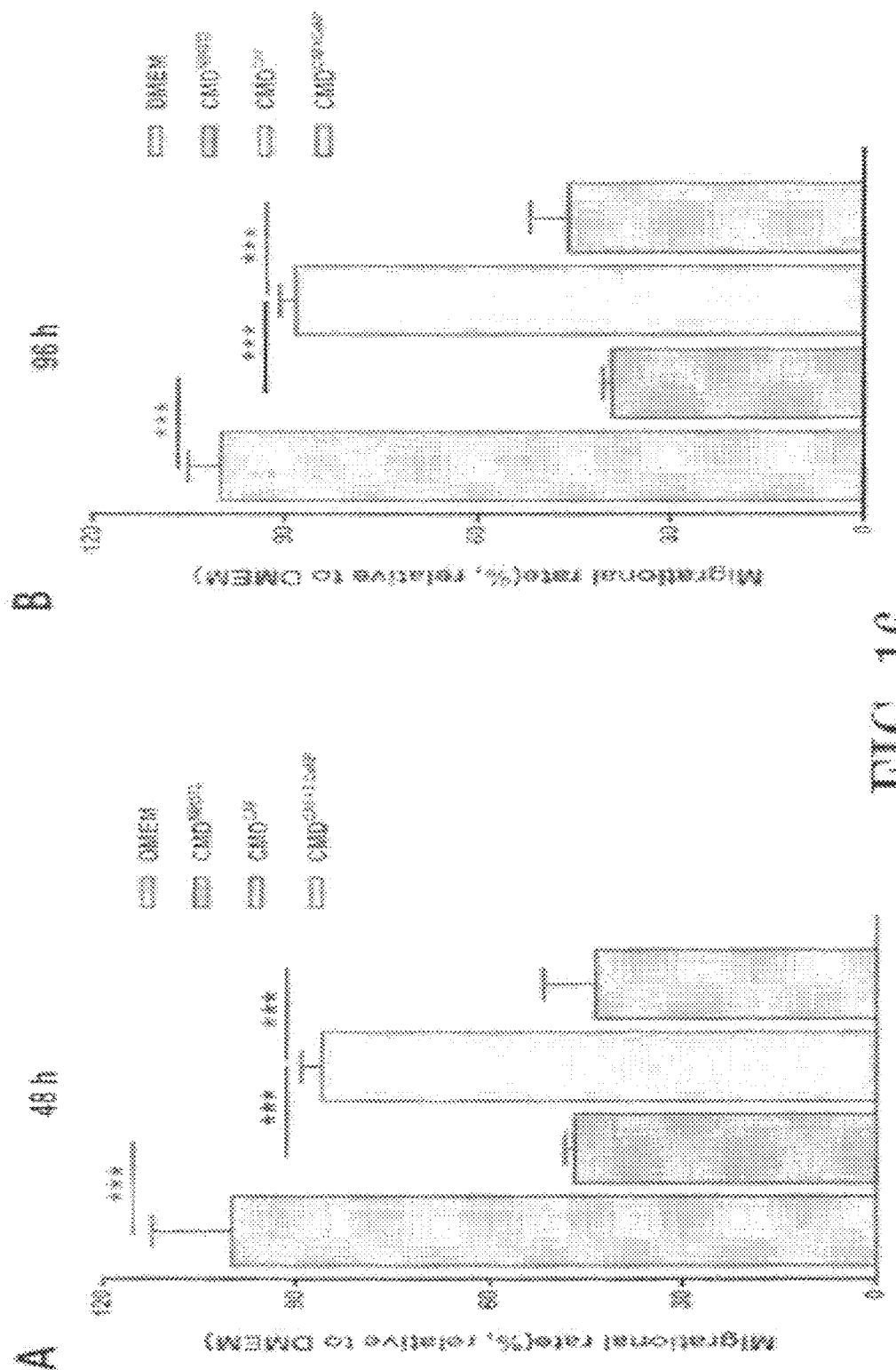

FIG. 16 shows quantitative analysis of migration rate of 4T1 cells after incubation in different media for (A) 48 hours and (B) 96 hours in the wound healing assay—data were analyzed using the Image-Pro Plus 6.0 software and expressed as mean±s.d. (n=3), and ***p<0.001.

Figure 17:
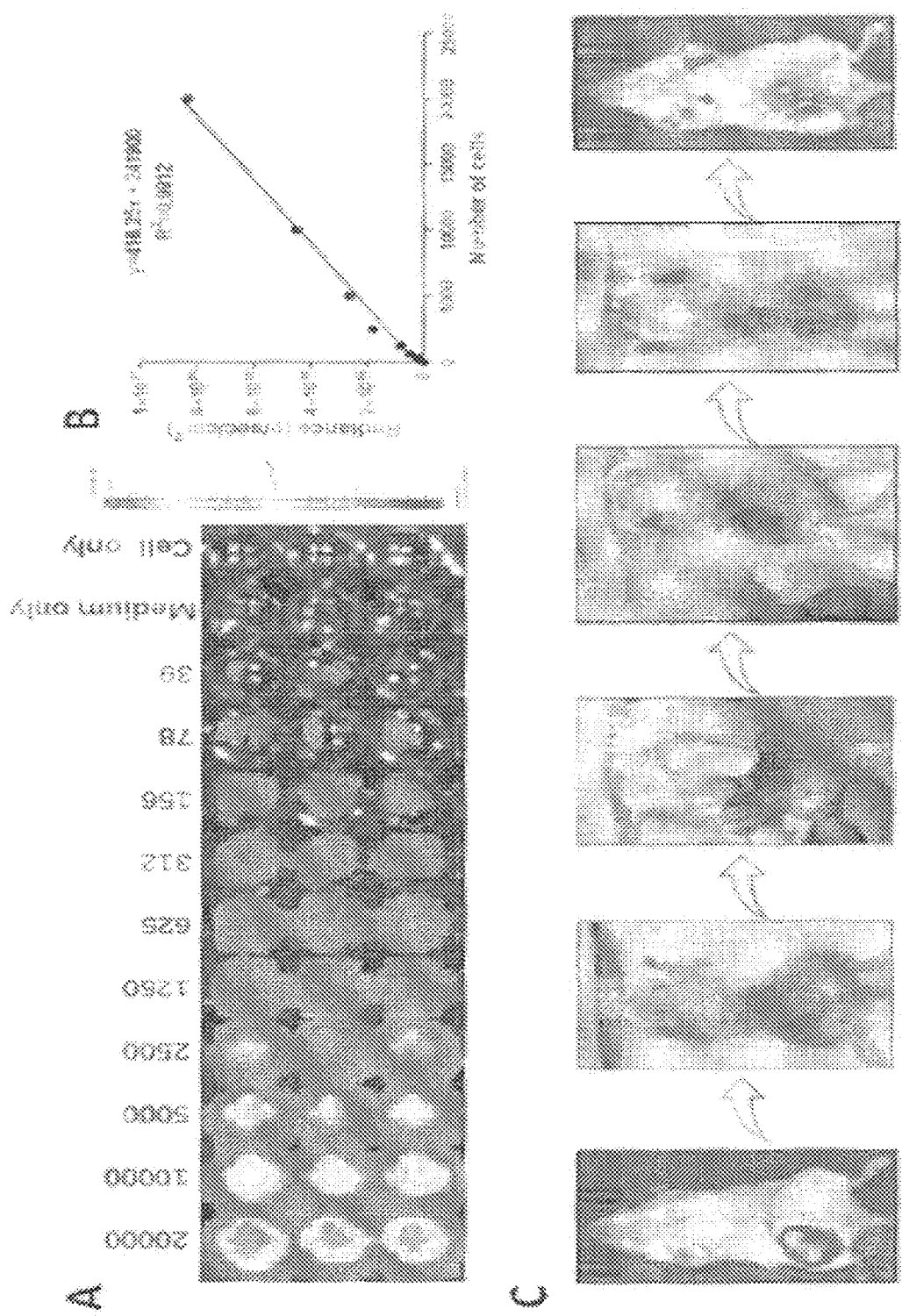

FIG. 17 shows sensitive detection of the 4T1-luc cells using the bioluminescence imaging and the surgical procedure of removing the tumor at: (A) ex vivo bioluminescence imaging of 4T1-luc using IVIS Spectrum system; (B) linear correlation between bioluminescence signal intensity and the number of 4T1 cells; and (C) photograph of tumor resection progress.

FIG. 18 shows representative immunofluorescence staining images of α-SMA, fibronectin, and e-cadherin expression in tumor tissues in different groups.

Figure 19:
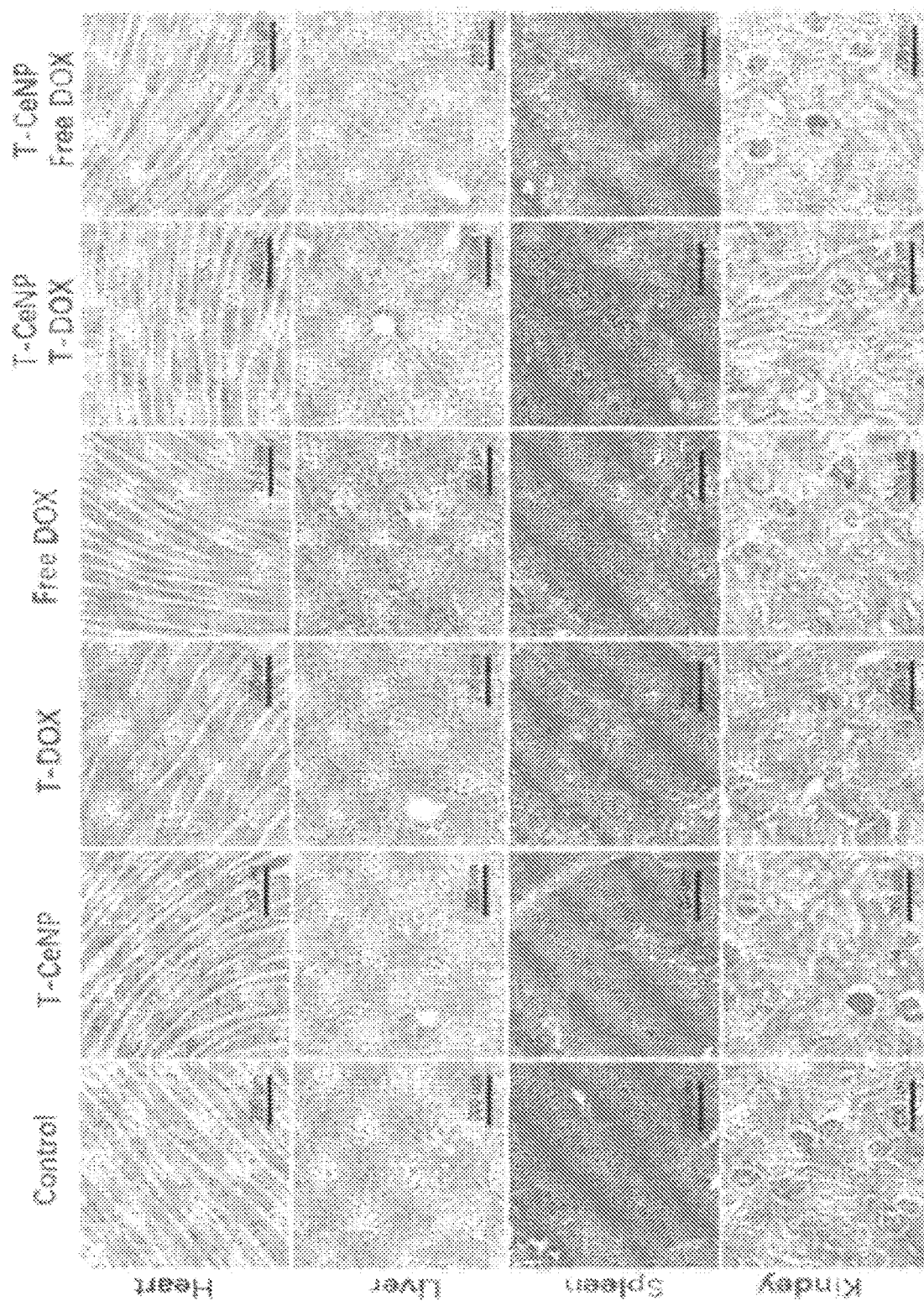

FIG. 19 shows histopathological examination (H&E staining) of the major organs (heart, liver, spleen, and kidney) of the mice in different groups.

The figures herein are for illustrative purposes only and are not necessarily drawn to scale.

DETAILED DESCRIPTION OF THE EXAMPLE EMBODIMENTS

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Unless specifically stated, terms and phrases used in this document, and variations thereof, unless otherwise expressly stated, should be construed as open ended as opposed to limiting. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise.

Furthermore, although items, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Where a range is expressed, a further embodiment includes from the one particular value and/or to the other particular value. The recitation of numerical ranges by endpoints includes all numbers and fractions subsumed within the respective ranges, as well as the recited endpoints. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, 4th edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.):

Antibodies, A Laboratory Manual (1988) (Harlow and Lane, eds.): Antibodies A Laboratory Manual, 2$^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, 2$^{nd}$ edition (2011).

As used herein, the singular forms "a", "an", and "the" include both singular and plural referents unless the context clearly dictates otherwise.

As used herein, "about," "approximately," "substantially," and the like, when used in connection with a measurable variable such as a parameter, an amount, a temporal duration, and the like, are meant to encompass variations of and from the specified value including those within experimental error (which can be determined by e.g. given data set, art accepted standard, and/or with e.g. a given confidence interval (e.g. 90%, 95%, or more confidence interval from the mean), such as variations of +/−10% or less, +/−5% or less, +/−1% or less, and +/−0.1% or less of and from the specified value, insofar such variations are appropriate to perform in the disclosure. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, a "biological sample" may contain whole cells and/or live cells and/or cell debris. The biological sample may contain (or be derived from) a "bodily fluid". The present disclosure encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, and cell cultures from bodily fluids. Bodily fluids may be obtained from a mammal organism, for example by puncture, or other collecting or sampling procedures.

As used herein, "agent" refers to any substance, compound, molecule, and the like, which can be administered to a subject on a subject to which it is administered to. An agent can be inert. An agent can be an active agent. An agent can be a primary active agent, or in other words, the component(s) of a composition to which the whole or part of the effect of the composition is attributed. An agent can be a secondary agent, or in other words, the component(s) of a composition to which an additional part and/or other effect of the composition is attributed.

As used herein, "active agent" or "active ingredient" refers to a substance, compound, or molecule, which is biologically active or otherwise that induces a biological or physiological effect on a subject to which it is administered to. In other words, "active agent" or "active ingredient" refers to a component or components of a composition to which the whole or part of the effect of the composition is attributed.

As used herein, "administering" refers to any suitable administration for the agent(s) being delivered and/or subject receiving said agent(s) and can be oral, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravitreal, intracerebral, and intracerebroventricular, intratympanic, intracochlear, rectal, vaginal, by inhalation, by catheters, stents or via an implanted reservoir or other device that administers, either actively or passively (e.g. by diffusion) a composition to the perivascular space and adventitia. For example, a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques. Administration routes can be, for instance, auricular (otic), buccal, conjunctival, cutaneous, dental, electro-osmosis, endocervical, endosinusial, endotracheal, enteral, epidural, extra-amniotic, extracorporeal, hemodialysis, infiltration, interstitial, intra-abdominal, intra-amniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronal (dental), intracoronary, intracorporus cavernosum, intradermal, intradiscal, intraductal, intraduodenal, intradural, intraepidermal, intraesophageal, intragastric, intragingival, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intrasinal, intraspinal, intrasynovial, intratendinous, intratesticular, intrathecal, intrathoracic, intratubular, intratumor, intratym panic, intrauterine, intravascular, intravenous, intravenous bolus, intravenous drip, intraventricular, intravesical, intravitreal, iontophoresis, irrigation, laryngeal, nasal, nasogastric, occlusive dressing technique, ophthalmic, oral, oropharyngeal, other, parenteral, percutaneous, periarticular, peridural, perineural, periodontal, rectal, respiratory (inhalation), retrobulbar, soft tissue, subarachnoid, subconjunctival, subcutaneous, sublingual, submucosal, topical, transdermal, transmucosal, transplacental, transtracheal, transtympanic, ureteral, urethral, and/ or vaginal administration, and/or any combination of the above administration routes, which typically depends on the disease to be treated, subject being treated, and/or agent(s) being administered.

As used herein "cancer" can refer to one or more types of cancer including, but not limited to, acute lymphoblastic leukemia, acute myeloid leukemia, adrenocortical carcinoma, Kaposi Sarcoma, AIDS-related lymphoma, primary central nervous system (CNS) lymphoma, anal cancer, appendix cancer, astrocytomas, atypical teratoid/Rhabdoid tumors, basa cell carcinoma of the skin, bile duct cancer, bladder cancer, bone cancer (including but not limited to Ewing Sarcoma, osteosarcomas, and malignant fibrous histiocytoma), brain tumors, breast cancer, bronchial tumors, Burkitt lymphoma, carcinoid tumor, cardiac tumors, germ cell tumors, embryonal tumors, cervical cancer, cholangiocarcinoma, chordoma, chronic lymphocytic leukemia, chronic myelogenous leukemia, chronic myeloproliferative neoplasms, colorectal cancer, craniopharyngioma, cutaneous T-Cell lymphoma, ductal carcinoma in situ, endometrial cancer, ependymoma, esophageal cancer, esthesioneuroblastoma, extracranial germ cell tumor, extragonadal germ cell tumor, eye cancer (including, but not limited to, intraocular melanoma and retinoblastoma), fallopian tube cancer, gallbladder cancer, gastric cancer, gastrointestinal carcinoid tumor, gastrointestinal stromal tumors, central nervous system germ cell tumors, extracranial germ cell tumors, extragonadal germ cell tumors, ovarian germ cell tumors, testicular cancer, gestational trophoblastic disease, Hairy cell leukemia, head and neck cancers, hepatocellular (liver) cancer, Langerhans cell histiocytosis, Hodgkin lymphoma, hypopharyngeal cancer, islet cell tumors, pancreatic neuroendocrine tumors, kidney (renal cell) cancer, laryngeal cancer, leukemia, lip cancer, oral cancer, lung cancer (non-small cell and small cell), lymphoma, melanoma, Merkel cell carcinoma, mesothelioma, metastatic squamous cell neck cancer, midline tract carcinoma with and without NUT gene changes, multiple endocrine neoplasia syndromes, multiple myeloma, plasma cell neoplasms, mycosis fungoides, myelodyspastic syndromes, myelodysplastic/myeloproliferative neoplasms, chronic myelogenous leukemia, nasal cancer, sinus cancer, non-Hodgkin lymphoma, pancreatic cancer, paraganglioma, paranasal sinus cancer, parathyroid cancer, penile cancer, pharyngeal cancer, pheochromocytoma, pituitary cancer, peritoneal cancer, prostate cancer, rectal cancer, Rhabdomyosarcoma, salivary gland cancer, uterine sarcoma, Sezary syndrome, skin cancer, small intestine cancer, large intestine cancer (colon cancer), soft tissue sarcoma, T-cell lymphoma, throat cancer, oropharyngeal cancer, nasopharyngeal cancer, hypopharyngeal cancer, thymoma, thymic carcinoma, thyroid cancer, transitional cell cancer of the renal pelvis and ureter, urethral cancer, uterine cancer, vaginal cancer, cervical cancer, vascular tumors and cancer, vulvar cancer, and Wilms Tumor.

As used herein, "chemotherapeutic agent" or "chemotherapeutic" refers to a therapeutic agent utilized to prevent or treat cancer.

As used herein, "control" can refer to an alternative subject or sample used in an experiment for comparison purpose and included to minimize or distinguish the effect of variables other than an independent variable.

The term "optional" or "optionally" means that the subsequent described event, circumstance or substituent may or may not occur, and that the description includes instances where the event or circumstance occurs and instances where it does not.

The term "molecular weight", as used herein, can generally refer to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed by the term "subject".

As used interchangeably herein, the terms "sufficient" and "effective," can refer to an amount (e.g. mass, volume, dosage, concentration, and/or time period) needed to achieve one or more desired and/or stated result(s). For example, a therapeutically effective amount refers to an amount needed to achieve one or more therapeutic effects.

As used herein, "tangible medium of expression" refers to a medium that is physically tangible or accessible and is not a mere abstract thought or an unrecorded spoken word. "Tangible medium of expression" includes, but is not limited to, words on a cellulosic or plastic material, or data stored in a suitable computer readable memory form. The data can be stored on a unit device, such as a flash memory or CD-ROM or on a server that can be accessed by a user via, e.g. a web interface.

As used herein, "therapeutic" can refer to treating, healing, and/or ameliorating a disease, disorder, condition, or side effect, or to decreasing in the rate of advancement of a disease, disorder, condition, or side effect. A "therapeutically effective amount" can therefore refer to an amount of a compound that can yield a therapeutic effect.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as cancer and/or indirect radiation damage. The effect can be therapeutic in terms of a partial or complete cure of a disease, condition, symptom or adverse effect attributed to the disease, disorder, or condition. The term "treatment" as used herein covers any treatment of cancer and/or indirect radiation damage, in a subject, particularly a human and/or companion animal, and can include any one or more of the following: (a) preventing the disease or damage from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

As used herein, the terms "weight percent," "wt %," and "wt. %," which can be used interchangeably, indicate the percent by weight of a given component based on the total weight of a composition of which it is a component, unless otherwise specified. That is, unless otherwise specified, all wt % values are based on the total weight of the composition. It should be understood that the sum of wt % values for all components in a disclosed composition or formulation are equal to 100. Alternatively, if the wt % value is based on the total weight of a subset of components in a composition, it should be understood that the sum of wt % values the specified components in the disclosed composition or formulation are equal to 100.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present disclosure. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the disclosure. For example, in the appended claims, any of the claimed embodiments can be used in any combination.

All patents, patent applications, published applications, and publications, databases, websites and other published materials cited herein are hereby incorporated by reference to the same extent as though each individual publication, published patent document, or patent application was specifically and individually indicated as being incorporated by reference.

Kits

Any of the compounds and/or formulations described herein can be presented as a combination kit. As used herein, the terms "combination kit" or "kit of parts" refers to the compounds, compositions, formulations, particles, cells and any additional components that are used to package, sell, market, deliver, and/or administer the combination of elements or a single element, such as the active ingredient, contained therein. Such additional components include, but are not limited to, packaging, syringes, blister packages, bottles, and the like. When one or more of the compounds, compositions, formulations, particles, cells, described herein or a combination thereof (e.g., agent(s)) contained in the kit are administered simultaneously, the combination kit can contain the active agent(s) in a single formulation, such as a pharmaceutical formulation, (e.g., a tablet, liquid preparation, dehydrated preparation, etc.) or in separate formulations. When the compounds, compositions, formulations, particles, and cells described herein or a combination thereof and/or kit components are not administered simultaneously, the combination kit can contain each agent or other component in separate pharmaceutical formulations. The separate kit components can be contained in a single package or in separate packages within the kit.

In some embodiments, the combination kit also includes instructions printed on or otherwise contained in a tangible medium of expression. The instructions can provide information regarding the content of the compounds and/or formulations, safety information regarding the content of the compounds and formulations (e.g., pharmaceutical formulations), information regarding the dosages, indications for use, and/or recommended treatment regimen(s) for the compound(s) and/or pharmaceutical formulations contained therein. In some embodiments, the instructions can provide directions and protocols for administering the compounds and/or formulations described herein to a subject in need thereof. In some embodiments, the instructions can provide one or more embodiments of the methods for administration of a pharmaceutical formulation thereof such as any of the methods described in greater detail elsewhere herein.

Cerium oxide nanoparticle (CeNP), a well-known metal catalyst, shows an outstanding biomedical potential attributing to its antioxidant properties. Cerium (III, $Ce^{3+}$) and cerium (IV, $Ce^{4+}$) oxidation states coexist on the surface of CeNP as a redox couple, exhibiting superoxide dismutase (SOD) and catalase (CAT) mimicking activities, respectively, which scavenges noxious intracellular reactive oxygen species (ROS). Moreover, these catalytic capabilities can be regenerated through a redox cycling mechanism. Therefore, CeNP receives a lot of attention as a promising antioxidant therapeutic agent for various oxidative stress associated diseases, such as chronic inflammation, neurodegeneration, neuroprotection, cardio-protection, as well as cancer. See, C. Xu, X. Qu, NPG Asia materials 2014, 6, e90; I. Celardo, J. Z. Pedersen, E. Traversa, L. Ghibelli, Nanoscale 2011.

Cancer is also termed as a "chronic inflammation disease", see S. Perwez Hussain, C. C. Harris, International Journal Of Cancer 2007, where overburdened ROS derived from the dysregulation between oxidation and anti-oxidation in cancer cells or TME may drive the initiation, progression, and metastasis of cancer. In this regard, CeNP would exert an excellent pharmacological potential in the treatment of cancer. CeNP is non-toxic for normal cells, including fibroblast. However, attributed to the increased acidification of tumor microenvironment, which converts CeNP into a toxic agent, CeNP exhibits toxicity for 518A2 melanoma cells, see M. Pěsić, A. Podolski-Renić, S. Stojković, B. Matović, D. Zmejkoski, V. Kojić, G. Bogdanović, A. Pavićević, M. Mojović, A. Savić, *Chemico-Biological Interactions* 2015, HT-29 colorectal adenocarcinoma cells, see Id., MKN28 gastric cancer cells, see Y. F. Xiao, J. M. Li, S. M. Wang, X. Yong, B. Tang, M. M. Jie, H. Dong, X. C. Yang, S. M. Yang, *Int J Nanomedicine* 2016, and SCL-1 squamous carcinoma cells, L. Alili, M. Sack, A. S. Karakoti, S. Teuber, K. Puschmann, S. M. Hirst, C. M. Reilly, K. Zanger, W. Stahl, S. Das, S. Seal, P. Brenneisen, *Biomaterials* 2011.

Apart from affecting cancer cells directly, the interaction between cancer cells and stroma TME is also a vital target regulated by CeNP. CeNP can prevent fibroblast from TGFβ-induced ROS-dependent transdifferentiation to myofibroblast, also known as α-SMA$^+$ CAF, resulting in a decrease of CAF-derived pro-invasive soluble factors and lowing the invasive ability of cancer cell, see L. Alili, M. Sack, A. S. Karakoti, S. Teuber, K. Puschmann, S. M. Hirst, C. M. Reilly, K. Zanger, W. Stahl, S. Das, S. Seal, P. Brenneisen, *Biomaterials* 2011.

Since CAF is located at the front line of tumor invasion and metastasis, inhibiting the transdifferentiation of fibroblast could potentially prevent tumor invasion, especially at the initial stage of tumor development. Rationally, reversed transdifferentiation from CAF to fibroblast (CAF reprogramming) realized by CeNP would be meaningful in inhibiting tumor invasion. However, only limited research investigated CeNP-based CAF reprogramming and its anti-metastasis effect. Herein, we developed a homologous targeted CeNP delivery nanoplatform through the camouflage coating of cancer cell membrane onto dendritic mesoporous organosilica nanoparticles as a novel additive agent for neoadjuvant chemotherapy to illustrate its relationship with CAF reprogramming, and evaluate its in vitro anti-metastatic effect and in vivo anti-metastasis efficacy in an orthotopic lung metastasis breast cancer model. See FIG. 1.

The biomimetic enzyme activity of the cerium oxide nanoparticle (CeNP) prefers ultrasmall particle size and bare surface. Unfortunately, those two features are not favorable for its in vivo application due to easy aggregation and fast renal filtration. To take advantage of the activity of CeNP for cancer therapy, a tumor targeted cerium oxide nanoparticle system, T-CeNP, has been developed. T-CeNP can be retained in the tumor in an orthotopic breast cancer metastatic model. Furthermore, T-CeNP effectively hinders cancer associated fibroblast (CAF) transdifferentiation and reprograms it back to normal fibroblast. Consequently, T-CeNP coupled with anticancer drugs reduces the size of primary tumor and prevents the post-surgery lung metastasis and liver metastasis of breast cancer.

Since tumor microenvironment plays a crucial role in the proliferation, migration, invasion, and metastasis of cancer cells, there is an urgent need for an approach that can remodel the tumor microenvironment. Dr. Xu from University of South Carolina developed a cancer targeted nanoparticle which can recondition the "soil" for a cancer cell to grow. Animal studies proved that the nanoparticle can reduce the size of primary tumor and prevent the post-surgery lung metastasis and liver metastasis of breast cancer.

Figure 2A:
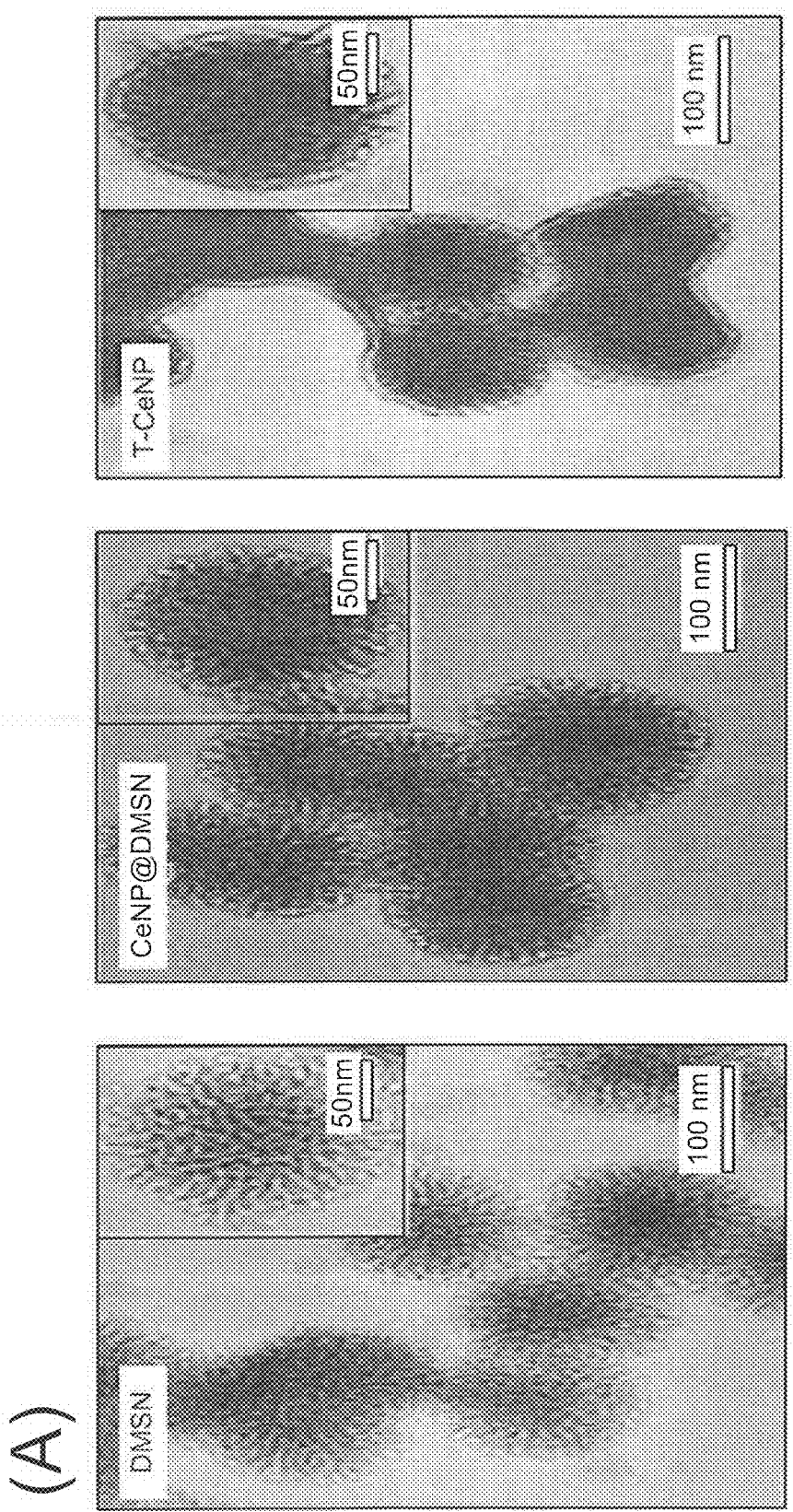
FIG. 2A shows characterization of CeNP-DMSN@CM: a) TEM of DMSN, CeNP loaded DMSN (CeNP-DMSN), and 4T1 cell membrane coated CeNP-DMSN (CeNP-DMSN@CM$^{4T1}$, T-CeNP); (b) The protein analysis of cell membrane, DMSN and cell membrane coated DMSN by SDS-PAGE. The nanoparticles size distribution of (c) DMSN, (d) CeNP-DMSN and (e) T-CeNP measured by DLS; and (f) Zeta potential of various nanoparticles.

It has been revealed that the biomimetic enzyme activity of the CeNP was positively correlated with its surface area-to-volume ratio, while negatively correlated with the thickness of its surface modification. See, I. Celardo, J. Z. Pedersen, E. Traversa, L. Ghibelli, *Nanoscale* 2011. To achieve a high antioxidant enzyme activity, a commercially available bared CeNP of 2-4 nm size was selected. Due to the ultrasmall size and bareness of the particle, this CeNP would inevitably lead to short half-time in the circulation and cause inter-particle agglomeration, which compromises the bioavailability and biomimetic enzyme efficiency of the CeNP in the targeted site. To break this dilemma, a biodegradable dendritic mesoporous organosilica nanoparticle (DMSN) with large pores was employed to accommodate the ultrasmall CeNP. The DMSN was fabricated according to a modified sol-gel method by co-condensation of inorganic and organosilica precursors. See Y. Yang, S. Bernardi, H. Song, J. Zhang, M. Yu, J. C. Reid, E. Strounina, D. J. Searles, C. Yu, *Chemistry of Materials* 2016. The incorporation of organosilica would render DMSN with outstanding biodegradation and biocompatibility for future clinical translation. See, M. Huo, L. Wang, Y. Chen, J. Shi, *Nat Commun* 2017. Transmission electron microscopic (TEM) images of synthesized DMSN showed a uniform spherical morphology with dendritic or urchin-like nanostructure (FIG. 2A at a) and a size around 120 nm (with 10-12 nm of pore size). The dendritic and large size porous structure provides ample space as reservoirs for the encapsulation of guest CeNP. The CeNP were easily loaded into the pores of DMSN through electrostatic interaction between the positively charged CeNP and negatively charged silanol group on surface of DMSN to yield CeNP@DMSN (FIG. 2A at a), as evidenced by the darkened core filled with speckle-like particles (FIG. 10 at D). The CeNP loading content and encapsulation efficiency were 63.7% and 73.4%, respectively. Moreover, the loading content can be easily tuned by adjusting the feed ration of CeNP to DMSN (data not shown). The success of loading CeNP was evidenced by enhanced contrast in the TEM image (FIG. 2A at a).

Figure 1:
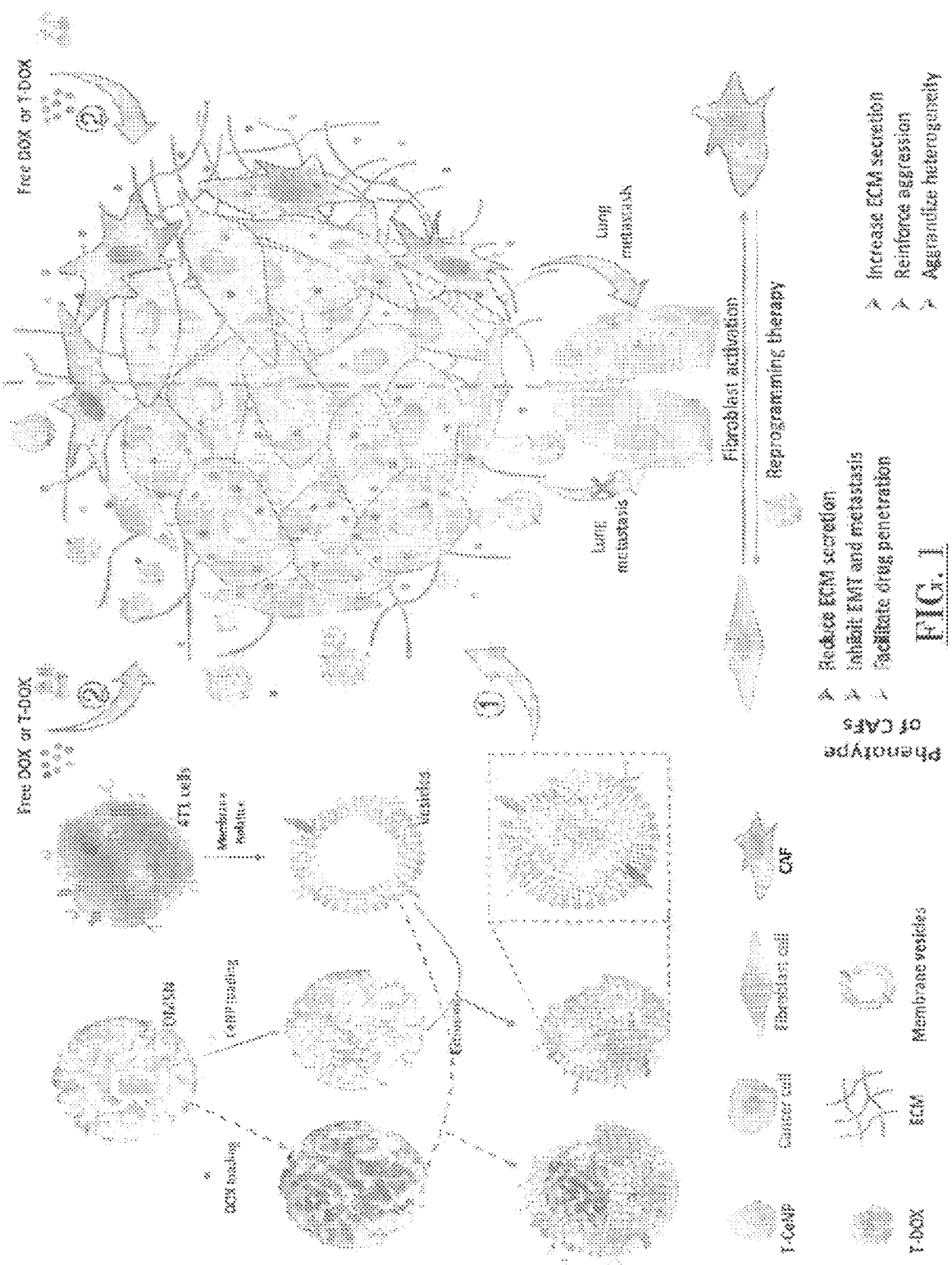
FIG. 1 shows one embodiment of a scheme for the fabrication of T-CeNP and its pathway in remodeling the tumor microenvironment.

To realize the homologous targeting effect, prolong the half-life in the circulation, and shield from the immune system phagocytosis for the nanoparticles, homologous cell membrane (CM) from 4T1 breast cancer cells were utilized to cloak CeNP@DMSN and yield CeNP@DMSN@CM$^{4T1}$ (T-CeNP) (FIG. 1). In contrast, CM from CT26 colon cancer cells was used as a control to produce CeNP@DMSN@CM$^{CT26}$ (N-CeNP). Similarly, the doxorubicin-loaded DOX@DMSN@CM$^{4T1}$ (T-DOX) and DOX@DMSN@CMCT26 (N-DOX) were prepared in parallel by replacing CeNP with doxorubicin. The loading efficiency and loading content of the T-DOX are 56.4% and 20.7%, respectively. The successful coating of CM on the surface of CeNP@DMSN was verified by TEM. In the TEM image (FIG. 2A at a), the urchin-like nanostructure of CeNP@DMSN covered by a shell with a thickness of 8 nm and appeared opaque, which is in accordance with other reports. See, D. Shao, M. Li, Z. Wang, X. Zheng, Y. H. Lao, Z. Chang, F. Zhang, M. Lu, J. Yue, H. Hu, *Advanced Materials* 2018. Sodium dodecyl sulfate polyacrylamide gel electrophoresis followed by protein staining displayed protein profiles of CM coated nanoparticles matched well with that of pure CM (FIG. 2*a* at b), indicating the membrane proteins from the source cells were retained and assembled on the shell of T-CeNP after coating. The dynamic light scattering (DLS) size of T-CeNP was 164.6 nm, slightly larger than that of its CeNP@DMSN counterpart (FIG. 2A at c, e). The zeta potential of T-CeNP was −27.7±0.7 mW (FIG. 2A at f), which is close to that of CM$^{4T1}$ while opposite to that of CeNP@DMSN. The sequential changes in particle size and zeta potential along with the construction process further demonstrated the successful fabrication of T-CeNP as expected.

As expected, the coating of cancer cell membrane improved the stability of T-CeNP and evidenced almost no size change before and after being suspended in the PBS.

Drug release study revealed that less than 30% DOX was released from T-DOX after 48 h of incubating in PBS. In contrast, more than 60% DOX was rerelease within 12 h in pH 5.0 buffer. Different from DOX, almost no detectable CeNP was released from T-CeNP under both pH conditions.

It was worth noting that we did not employ CM from CAF to mask the CeNP@DMSN mainly considering the anatomical architecture characterization of the tumor. Since CAFs are heterogeneously located around the peripheral region of the tumor mass and adjacent to the leaky tumor vessels, targeting tumor tissue would lead to some unintended binding and internalization of nanoparticles into CAFs. See, L. Miao, J. M. Newby, C. M. Lin, L. Zhang, F. Xu, W. Y. Kim, M. G. Forest, S. K. Lai, M. I. Milowsky, S. E. Wobker, L. Huang, *ACS Nano* 2016. Through the intratumor "off-target effects", we expect T-CeNP to realize mainly distribution in 4T1 cells and partially in CAFs.

Figure 2B:
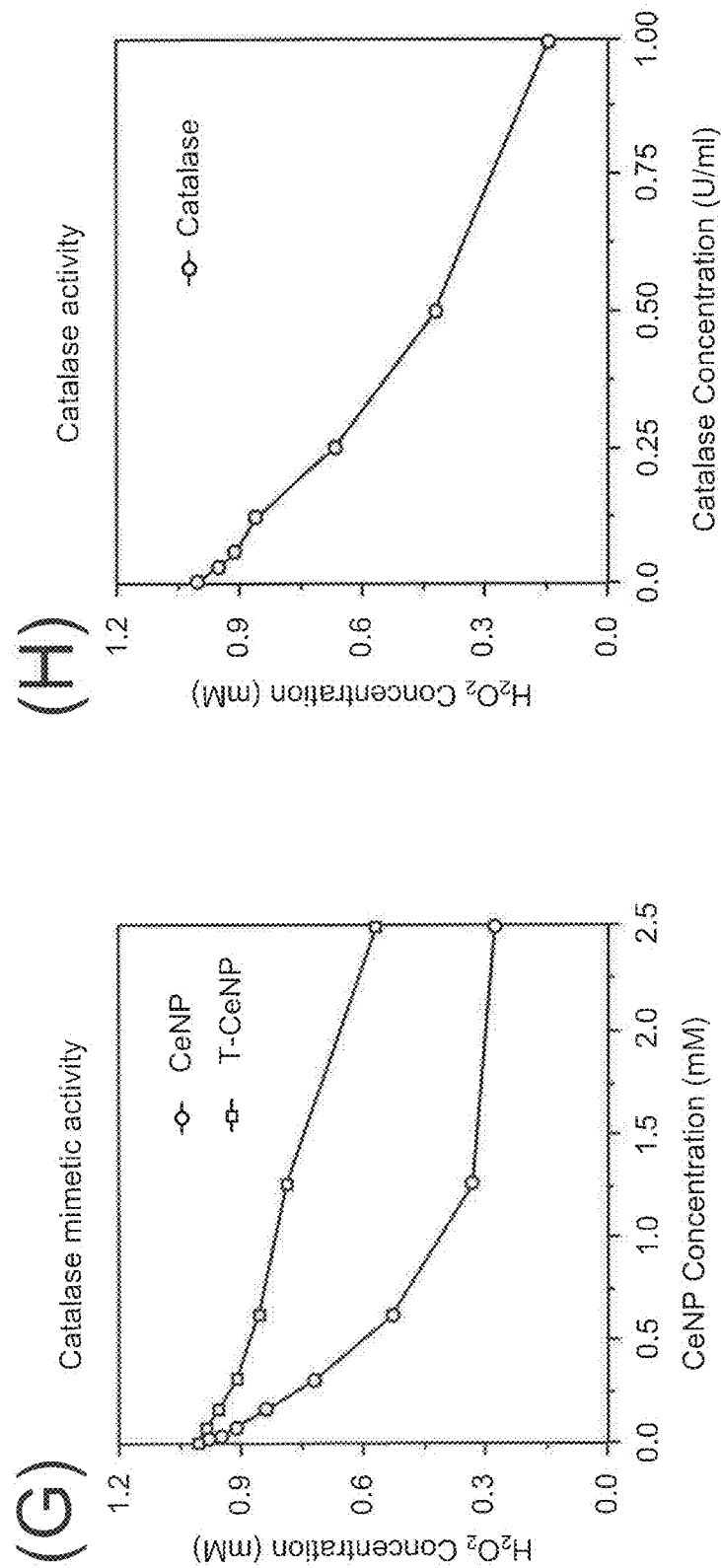
FIG. 2B shows characterization of CeNP-DMSN@CM: evaluation of (g) catalase mimetic activity of CeNP and CeNP-DMSN in $H_2O_2$ solution; (i) evaluation of SOD mimetic activity of CeNP, CeNP-DMSN and CeNP-DMSN@CM by referencing to SOD; (j) Co-localization of cell tracker green labeled cell membrane and Cy5 labeled DMSN of DMSN@CM$^{4T1}$ in 4T1 cell; (k) Cellular uptake in 4T1 cells after incubation with Cy 5 labeled DMSN@CM$^{4T1}$ and DMSN@CM$^{CT26}$-data are expressed as mean±s.d. (n=3) for panels f and i.

To validate the catalase-like activity of free CeNP and T-CeNP, colorimetric based assay was employed. It was revealed that both free CeNP and T-CeNP could effectively reduce the $H_2O_2$ in a concentration-dependent manner (FIG. 2B at g), which is similar to the activity of catalase (FIG. 2B at h). Moreover, the discolored reaction solution of CeNP and $H_2O_2$ after aging and the appearance of yellowish color after the addition of the $H_2O_2$ proved that the catalytic capability of CeNP could be regenerated (FIG. 11). In addition, FIG. 2B at i confirmed that both free CeNP and T-CeNP exhibited SOD mimetic activity in a concentration-dependent manner. Thus, due to the SOD and CAT mimicking activities, T-CeNP is capable of scavenging the toxic reactive oxygen species (ROS) in the TME. FIG. 11 shows photos of recyclable ROS scavenging capacity of ceria nanoparticle. Ceria nanoparticles can decompose $H_2O_2$ as catalase, while themselves are oxidized to yellow. Then the oxidized ceria nanoparticles gradually regain their enzyme-like activity and scavenge ROS ability.

To investigate the structural integrity of the DMSN@CM during drug delivery, the cell membrane was fluorescently tagged with CellTracker™ Green, and DMSN was labeled with Cy5, respectively. 4T1 cells were incubated with the dual fluorescence-labeled T-CeNP for 1 h, followed by examining the intracellular fluorescence signal with confocal laser scanning microscopy (CLSM). The co-localization of the fluorescence signals inside the cells from Cell-Tracker™ Green and Cy5 proved the structural integrity of the CM cloaked DMSN upon cellular endocytosis (FIG. 2B at j). After the successful coating of DMSN with the cancer cell membrane, the intracellular uptake of DMSN@CM coated with different cell membranes was carried out to investigate their homologous targeting ability. In 4T1 cells, it was found that intracellular red fluorescence intensity was significantly higher in DMSN@CM$^{4T1}$ treated cells compared with that in DMSN@CM$^{CT26}$ treated cells (FIG. 2B at k). These results indicated that the retained 4T1 membrane proteins coated on the DMSN still maintained their primary ability and significantly enhanced the nanoparticles' internalization into its corresponding source cells, attributed to the homotypic adhesive interactions mediated by the adhesion molecules on the cell membrane. See, R. H. Fang, C. M. Hu, B. T. Luk, W. Gao, J. A. Copp, Y. Tai, D. E. O'Connor, L. Zhang, *Nano Lett* 2014. Moreover, this homotypic adhesive interaction was of superior selectivity to its source cells.

The biocompatibility of T-CeNP was evaluated in 4T1 cells and NIH-3T3 cells by MTT assay. T-CeNP exhibited negligible cytotoxicity to both cells at a concentration up to 1200 µM (FIG. 12 at A), indicating the good biocompatibility of T-CeNP. To explore the potential combinatory application in cancer chemotherapy, we investigated the influence of T-CeNP on the cytotoxicity of free DOX to 4T1 cells and NIH-3T3 cells. The cells were pre-incubated with various concentrations of T-CeNP for 24 h, followed by treatment with 0.5 µM of free DOX for another 48 h. Cell proliferation assay found that in the whole tested concentration range, free CeNP did not show a significant influence on DOX-induced toxicity to NIH3T3 cells (FIG. 12 at B). Interestingly, it was revealed that, at high concentrations (300 µM and 600 µM), CeNP slightly boosted DOX toxicity to 4T1 cells (FIG. 12 at C). These discrepant pharmacological behaviors, of which nontoxicity to normal cells (NIH3T3) but synergistic enhanced toxicity with DOX to tumor cells (4T1), were consistent with reported literature, see M. Sack, L. Alili, E. Karaman, S. Das, A. Gupta, S. Seal, P. Brenneisen, *Molecular Cancer Therapeutics* 2014, which is mainly mediated by a pH-dependent redox activity of CeNP.

We next investigated the anti-proliferative effect of constructed nanoparticles on 4T1 cells. 4T1 cells were pre-treated with or without a constant dose (100 µM) of T-CeNP for 24 h, followed by incubating with T-DOX, N-DOX, and free DOX for 4 h. After another 48 h of incubation, the cell viability was measured by MTT. It was found that the pretreatment of T-CeNP had little influence on the toxicity of DOX in all forms (FIG. 12 and D), no matter free DOX or the ones loaded in DMSN (FIG. 12 at C), which was coincident with the previous results. At all tested concentrations, T-DOX was more potent in killing 4T1 cells than N-DOX, which could be credited to the accelerated cellular uptake mediated by 4T1 cell membrane protein (FIG. 2B at g). However, compared with free DOX, T-DOX did not show improved toxicity to 4T1, which could result from the relatively slow intracellular release of DOX from T-DOX as previously reported. See, H. J. Liu, X. Luan, H. Y. Feng, X. Dong, S. C. Yang, Z. J. Chen, Q. Y. Cai, Q. Lu, Y. Zhang, P. Sun, *Advanced Functional Materials* 2018, 28, 1801118; X. Dong, H.-J. Liu, H.-Y. Feng, S.-C. Yang, X.-L. Liu, X. Lai, Q. Lu, J. F. Lovell, H.-Z. Chen, C. Fang, *Nano Letters* 2019.

Growing evidence suggested that CeNP inhibits cancer cell migration and invasion, which is critical for tumor growth and metastasis. See, N. Kramer, A. Walzl, C. Unger, M. Rosner, G. Krupitza, M. Hengstschlager, H. Dolznig, *Mutation Research/Reviews in Mutation Research* 2013. Herein, we carried out wound-healing assay and Transwell invasion assay to investigate the anti-metastasis effect of CeNP. As shown in FIG. 3A at a-b, the control (untreated) cells showed a strong migration ability, indicating the highly metastatic capacity of 4T1 cells. T-CeNP exhibited an inhibitory effect on migration in a concentration-dependent manner. The healing rate of the T-CeNP treated cells at nontoxic concentration range of 50 nM, 100 nM and 200 nM was 72%, 49% and 20%, respectively, which are significantly lower than that in N-CeNP treated cells. The difference of inhibitory effect between T-CeNP and N-CeNP was mainly attributed to the uptake difference between those nanoparticles (FIG. 2B at g). It is worth noting that due to the instability of free CeNP in the culture medium, only a limited migration inhibitory effect was observed in the free CeNP treated 4T1 cells. In the meantime, Transwell invasion assay found that T-CeNP could reduce the invasion of 4T1 cells in a concentration-dependent manner (FIG. 3B at c-d) and exhibited higher potency than its free and non-targeted counterparts.

It has been verified that, cancer cell intrinsic invasive and metastasis ability can be inhibited by increasing the expression of ATP-dependent RNA helicase DEAH (Asp-Glu-Ala-His) box helicase 15 (DHX15). Herein, to investigate the potential molecular mechanism of T-CeNP reducing the invasive and metastatic ability of cancer cells, we examined how T-CeNP affects the expression of DHX15 in 4T1 cells by western immunoblotting. It was revealed that both free CeNP and T-CeNP improved the expression of DHX15, see FIG. 12, suggesting that the inhibitory effect of T-CeNP on the invasion and metastasis of cancer cells may be attributed to the upregulation of DXH15. Collectively, T-CeNP would be of great promise in inhibiting the migration and metastasis of the 4T1 tumor.

Figure 4A:
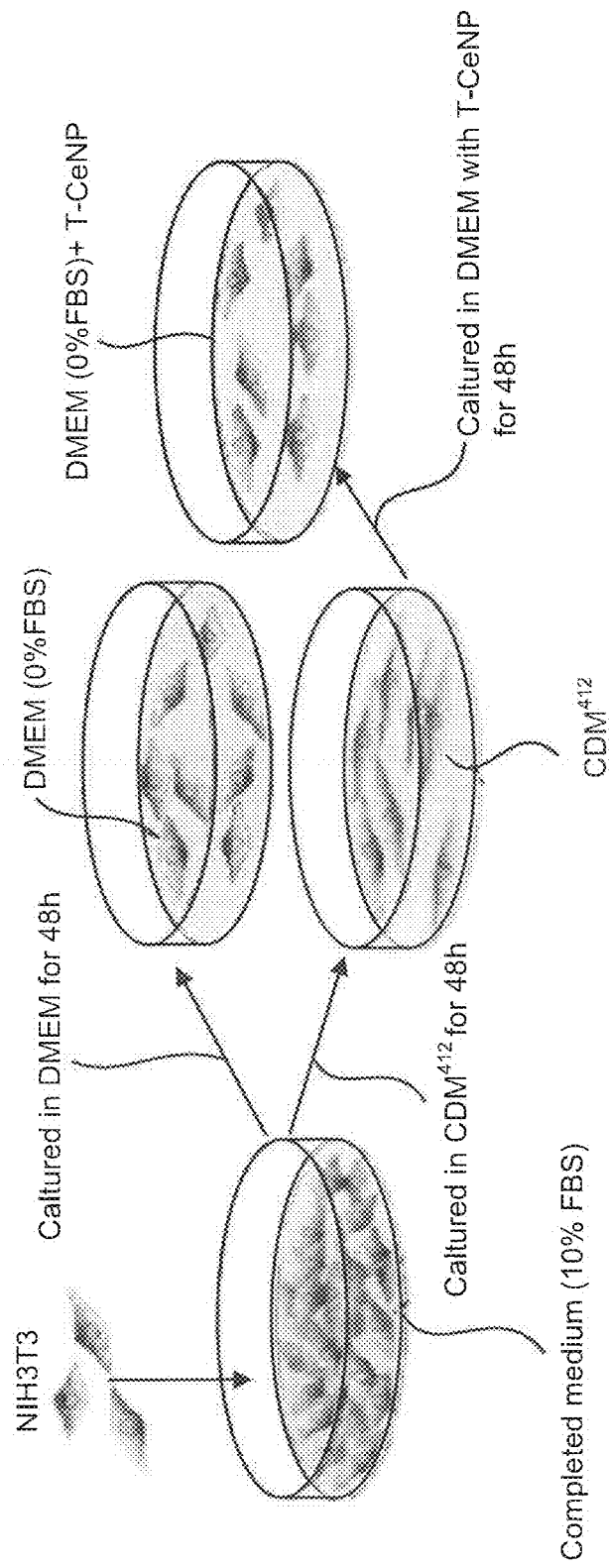
FIG. 4A shows cancer associated fibroblasts differentiation and transdifferentiation at: (a) diagram of cancer associated fibroblasts differentiation of NIH3T3-induced by CMD and the transdifferentiation effect of T-CeNP on CAF; (b) Western blotting and quantitative analysis of α-SMA; (c); and, fibronectin (d) expression in NIH3T3 cells, cancer associated fibroblasts (CAF) induced by CMD$^{4T1}$ and CAF treated with T-CeNP
Figure 4B:
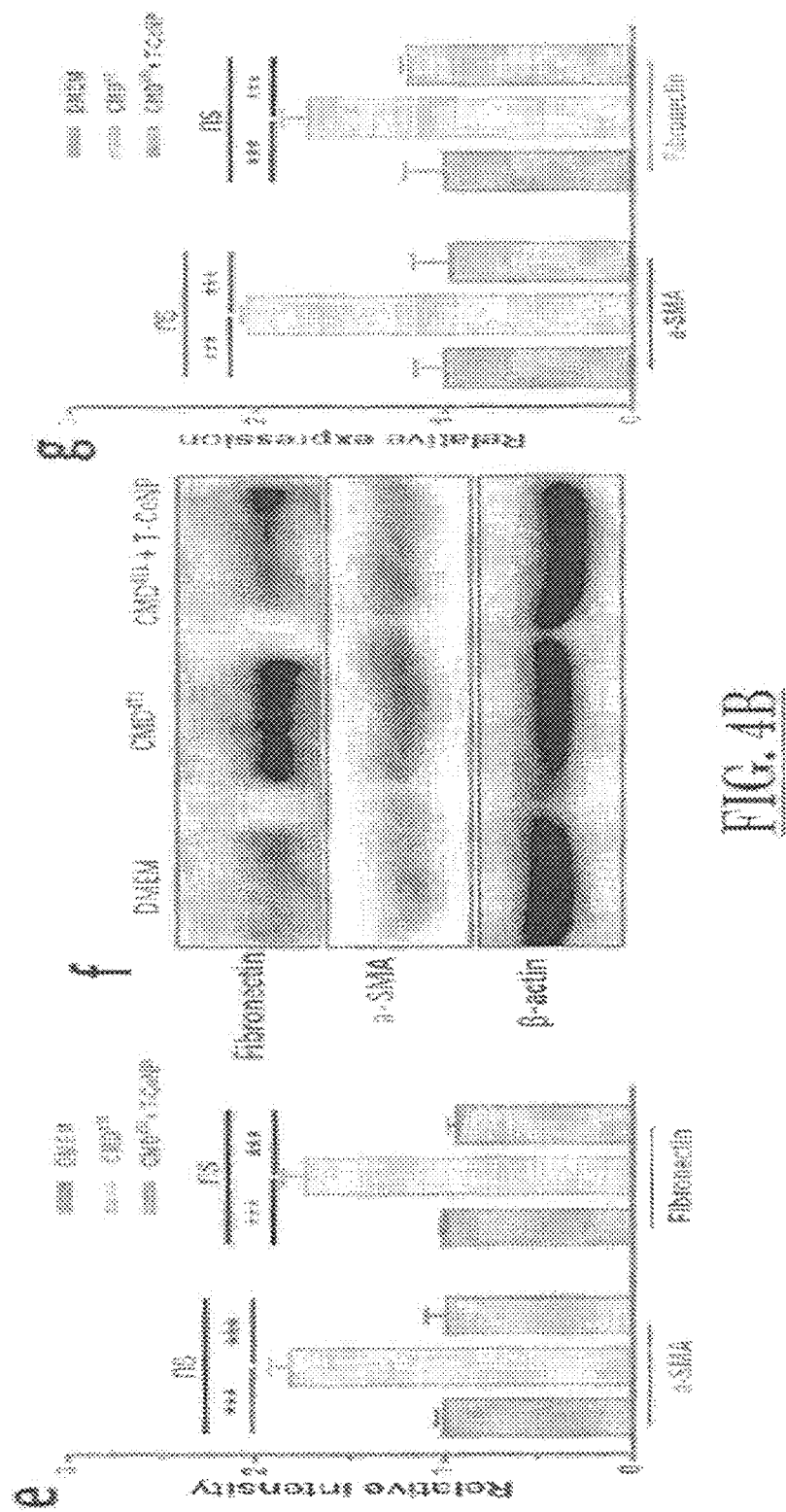
FIG. 4B shows immunofluorescence images of α-SMA (e) and fibronectin (f) expression in NIH3T3 cells, cancer associated fibroblasts (CAF) induced by CMD$^{4T1}$ and CAF treated with T-CeNP—quantitative analysis of α-SMA (g)

Apart from directly affecting the viability and motility of 4T1 cells, the influence of T-CeNP on the interaction between cancer cells and CAF in the TME would be a promising alternative for cancer therapy. In an in vitro setting, CAFs are mainly acquired by isolating from tumor tissue or through mesenchymal-mesenchymal transition (MMT) from fibroblasts. See, B. Cat, D. Stuhlmann, H. Steinbrenner, L. Alili, O. Holtkötter, H. Sies, P. Brenneisen, *Journal Of Cell Science* 2006. CAF derived from tumor tissue retains most primitive characteristics of CAF, whereas heterogeneous. An alternative approach is transdifferentiating from fibroblasts, which is more manipulatable and results in homogeneous cells. Herein, we used a conditioned medium from 4T1 cells ($CMD^{4T1}$) to drive NIH3T3 transdifferentiating to CAF, as shown in FIG. 4A at a, see Id. and H. Chen, W.-W. Yang, Q.-T. Wen, L. Xu, M. Chen, *Experimental And Molecular Pathology* 2009. The simultaneously displayed typical CAF features, including elongated morphology and aligned cell-cell contact (FIG. 4A at b), suggested that $CMD^{4T1}$ treatment successfully transformed NIH3T3 into CAF. In the meantime, α-SMA, a classical marker for activated fibroblasts (CAF), was significantly elevated compared with control NIH3T3 as identified by immunofluorescence staining and western blotting (FIG. 3A at c-d and FIG. 3B at e-g). As a proof-of-concept of reprogramming CAF, we were curious about whether T-CeNP could reeducate CAF back to its original fibroblast phenotype. FIG. 4A at b revealed that NIH3T3 exhibited a fibroblast-like phenotype after being incubated with T-CeNP for 48 h. In addition, immunofluorescence staining (FIG. 4A at c and e) confirmed that T-CeNP treatment for CAF resulted in pronounced silencing of α-SMA, which was in accordance with the western blot results (FIG. 4B at f-g), suggesting the ability of T-CeNP reverting CAF back to the quiescent state. As aforementioned, one prominent feature of CAF was that CAF secreted high levels of ECM proteins, such as fibronectin, to mediate various activities of cancer cells, including adhesion, migration, growth, and differentiation by altering the architecture and physical properties of the ECM (named ECM remodeling). See, B. Erdogan, M. Ao, L. M. White, A. L. Means, B. M. Brewer, L. Yang, M. K. Washington, C. Shi, O. E. Franco, A. M. Weaver, *Journal of Cell Biology* 2017, 216, 3799. Considering its abundance in ECM and critical roles, fibronectin was employed as a representative indicator of ECM dynamic change during CAF transdifferentiation and reprogramming. Notably, compared with original NIH3T3, $CMD^{4T1}$ incubation upregulated the expression of fibronectin in NIH3T3 cells, while T-CeNP treatment remarkably attenuated fibronectin production back to its initial level (FIG. 4A at d and FIG. 4B at e). Furthermore, western blot analysis of the secreted fibronectin showed a similar trend (FIG. 4B at f-g). These results manifested the critical role of CAF in the synthesis of ECM proteins and the construction of ECM and validated that T-CeNP based CAF reprogramming could be a promising strategy for ECM remodeling. Furthermore, pretreatment the NIH3T3 cells with T-CeNP effectively prevented the transdifferentiation of fibroblast to CAF as evidenced by the unchanged level of α-SMA and fibronectin after $CMD^{4T1}$ treatment (FIG. 13).

In addition to directing the formation of ECM, activated CAF could also orchestrate cancer growth, progression and metastasis through paracrine growth factors. Different from directional contact-type of cancer-ECM interaction, paracrine mediated crosstalk between cancer cells and CAF was intricate and usually reciprocal. To minimize this reciprocity and simplify the experimental procedure, CMD derived from different types of fibroblasts were collected and used to culture 4T1 cells to investigate the effect of the activated fibroblast on the proliferation, migration, and invasion of 4T1. Researchers found that the loss of E-cadherin promotes the proliferation, invasion, and/or metastasis of breast cancer cells. See, G. Berx, F. Van Roy, *Breast Cancer Research* 2001, 3, 289; F. Yang, Y. Takagaki, Y. Yoshitomi, T. Ikeda, J. Li, M. Kitada, A. Kumagai, E. Kawakita, S. Shi, K. Kanasaki, *Cancer Research* 2019. Thus, an approach that can restore the expression of E-cadherin could be a promising tool in preventing cancer metastasis. It was revealed that the E-cadherin level expressed in 4T1 cells was reduced when cultured in the conditioned medium of CAF ($CMD^{CAF}$) (FIG. 5A at a). In contrast, cells restored the E-cadherin level when cultured in the conditioned medium of CAF treated with T-CeNP ($CMD^{CAF-T-CeNP}$). Furthermore, pretreatment of T-CeNP successfully prevented the decline of E-cadherin in 4T1 cells cultured in $CMD^{CAF}$ (FIG. 5A at b).

TGF-β is a cytokine that plays a vital role in cell proliferation, differentiation, migration, and/or invasion. It has been reported that CeNP intervenes in the differentiation and transdifferentiation between fibroblast and myofibroblast (CAF) through a TGF-β associated signaling pathway. See, D. D. Liu, J. C. Zhang, Q. Zhang, S. X. Wang, M. S. Yang, *Journal Of Cellular Biochemistry* 2013. FIG. 14 found that CAF generated much higher level of TGF-β than its fibroblast counterpart. However, the addition of T-CeNP effectively quenched the production of TGF-β in CAF. In addition, the pretreatment with T-CeNP also successfully reduced the TGF-β generation in 4T1 cells cultured in $CMD^{NIH3T3}$ and $CMD^{CAF}$ (FIG. 5A at c). FIG. 15 at A revealed that, although there was no statistical difference in cell viability of 4T1 cells treated with $CMD^{NIH3T3}$ and $CMD^{CAF}$, the value of cell viability of $CMD^{CAF}$ treated 4T1 cells was higher than that of $CM^{NIH3T3}$ treated ones, suggesting the growth-promoting effect of CAF on 4T1 cells. Whereas, conditioned medium from T-CeNP pretreated CAF ($CMD^{CAF+ceNP}$) could reinstall the viability to the level of original NIH3T3, indicating the reprogramming function of CeNP on CAF. It was worth noting that cell viability in all CMD treated 4T1 cells were lower than the control one (blank DMEM treated 4T1 cells), mainly owing to the consumption or exhaustion of nutrition by CMD furnishing cell. Impressively, although there were no statistical differences in cell viability in all of CMD treated cell lines, significant phenotypic morphology changes were noticed (FIG. 15 at B), where compared to inanimate state of $CMD^{NIH3T3}$ treated 4T1 cells, $CMD^{CAF}$ treated ones exhibited elongated and vigorous pseudopodia and a spindle-like shape, portending enhanced ability of motility and invasion. As we expected, $CMD^{CAF+T-CeNP}$ treated 4T1 cells shared a similar morphology to that of $CMD^{NIH3T3}$ treated ones.

Inspired by the heterogenetic morphology in cells after different treatments, we further investigated the combinatory effect of T-CeNP and fibroblast on the migration and invasion of 4T1 cells through wound healing assay and Transwell invasion assay. As shown in FIG. 5A at d-f and FIG. 16, the migration and invasion abilities of $CMD^{NIH3T3}$ treated 4T1 cells were dramatically reduced compared to control ones, demonstrating the anti-metastasis effect of normal fibroblast. IN contrast, $CMD^{CAF}$ exhibited enhanced effect on the cellular migration and invasion and bulged elongated and vigorous pseudopodia for 4T1 cells in morphology, demonstrating the pro-migrating and invasive features of CAF. However, after reprogramming CAF with T-CeNP, 4T1 cells cultured in $CMD^{CAF+T-CeNP}$ reduced their migration and invasiveness to levels similar to that of $CMD^{NIH3T3}$ treated 4T1 cells. Collaboratively, these results indicated that T-CeNP treatment could efficiently reeducate CAF back to fibroblast and block the crosstalk between CAF and tumor cells, thereby minimizing the metastatic promoting effect of CAFs. To further investigate the impact of T-CeNP on the direct crosstalk between fibroblast and 4T1 cells, a cell co-culture model was employed. The boosted E-cadherin signals (FIG. 5B at g) and the reduced fibronectin signals and integrity (FIG. 5B at h) in T-CeNP treated cells, as well as the morphology change in the fibroblasts further proved that T-CeNP could prevent the generation of CAF and serve as an effective tool to prevent the metastasis of breast cancer.

Anthracycline-containing regimens are predominantly used in neoadjuvant chemotherapy for breast cancer. See, J. Wang, T. A. Buchholz, L. P. Middleton, D. C. Allred, S. L. Tucker, H. M. Kuerer, F. J. Esteva, G. N. Hortobagyi, A. A. Sahin, *Cancer* 2002, 94, 3107; M. S. van Ramshorst, A. van der Voort, E. D. van Werkhoven, I. A. Mandjes, I. Kemper, V. O. Dezentjé, I. M. Oving, A. H. Honkoop, L. W. Tick, A. J. van de Wouw, *The Lancet Oncology* 2018. However, only a little benefit was achieved from this neoadjuvant chemotherapy in the majority of patients. Surprisingly, it has been reported that DOX treatment can even promote the metastasis of breast cancer, see W.-C. Chen, Y.-A. Lai, Y.-C. Lin, J.-W. Ma, L.-F. Huang, N.-S. Yang, C.-T. Ho, S.-C. Kuo, T.-D. Way, *Journal Of Agricultural And Food Chemistry* 2013, 61, 11817; N. Chintalaramulu, R. Vadivelu, N. Nguyen, I. Cock, *Inflammopharmacology* 2020, especially at lower doses. To investigate the relationship between DOX and the differentiation and transdifferentiation of CAF and the potential effect of T-CeNP in inhibiting DOX-induced metastasis, T-CeNP was added to NIH3T3 and 4T1 cells either before or after receiving DOX treatment. The expression of the CAF related proteins, including α-SMA and fibronectin, and metastasis-associated E-cadherin were evaluated by immunocytochemistry. FIGS. 6A and 6B confirmed that the pro-differentiation to CAF and pro-metastatic effect of DOX treatment for fibroblast and breast cancer cells, respectively, evidenced by the boosted level of α-SMA and fibronectin, and the declined E-cadherin expression in DOX treated cells. As expected, the pretreatment with T-CeNP successfully transdifferentiated CAF to fibroblast and prevented the pro-metastatic response of DOX treated 4T1 cell as evidenced by the non-changed expression of α-SMA, fibronectin, and E-cadherin (FIG. 6A at a-c). Furthermore, the reduced α-SMA and fibronectin expression in DOX-pretreated NIH3T3 cells, and the increased E-cadherin expression in the DOX-pretreated 4T1 cells after receiving T-CeNP treatment validated that T-CeNP could transdifferentiate DOX-induced CAF to fibroblast and rescue DOX-induced 4T1 cells from metastasis (FIG. 6B at d-f). The quantitative comparison of their corresponding fluorescence intensities further verified these trends.

In the pathology of most patient breast tumor tissue, most of the central tumor nests were surrounded by elongated fibrous stroma region, consisted of CAF and ECM generated by CAF. See, D. L. Priwitaningrum, J.-B. G. Blonde, A. Sridhar, J. van Baarlen, W. E. Hennink, G. Storm, S. Le Gac, J. Prakash, *Journal Of Controlled Release* 2016. It is noteworthy that the abundance of leaky tumor blood vessels were located in the stromal region, which indicates that crossing the stromal barrier is the prerequisite for drug molecules or nanoparticles reaching the tumor nest. Thus, in contrast to planimetric/wo-dimensional (2D) culture of cancer cells in vitro, three-dimensional (3D) tumor spheroid model, especially tumor cells and stromal cells 3D co-culturing heterospheroid more closely recapitulate the clinical tumor microenvironment, offering a suitable in vitro model to understand the composition and organization of tumor, intratumor molecular and cellular mechanism, and cell-cell interactions, see Id. Thus, 3D-heterospheroid is an ideal model for systematically investigating TME and intratumor penetration characteristics of nanomedicine. Herein, to mimic in vivo enriched tumor stroma circumstance, we generated 4T1 and NIH3T3 co-culture spheroids to investigate T-CeNP medicated cancer cells-fibroblast interaction, tumor structure and following chemotherapy. To track cellular organization in the heterospheroid, NIH-3T3 cells stably transfected with green fluorescence protein (GFP) and 4T1 cells labeled with CellTracker™ Deep Red Dye were adopted for the formation of the spheroid. As shown in FIG. 7, in the initially formed spheroid, 4T1 and NIH3T3 cells were homogeneously distributed throughout the spheroid. As the experiment proceeded, the distribution of 4T1 was of no noticeable change. In contrast, part of the NIH3T3 centralized to the core, and the rest of the NIH3T3 cells migrated to the periphery of spheroid and embraced the tumor nest, displaying an apparent architecture of stroma-surrounded tumor type. See, L. Miao, J. M. Newby, C. M. Lin, L. Zhang, F. Xu, W. Y. Kim, M. G. Forest, S. K. Lai, M. I. Milowsky, S. E. Wobker, L. Huang, *ACS Nano* 2016. In contrast, the intervention of T-CeNP markedly rearranged the spheroid architecture, evidenced by the majority of NIH3T3 cells were located in the center with a few NIH3T3 cells was unconsolidated aligning throughout 4T1 cells shell (FIG. 7 at b), and exposing the 4T1 cells spheroid for the access of small molecules and nanomedicines. Consequently, pretreatment with T-CeNP followed with T-DOX treatment resulted in smaller 4T1 cells core in the spheroid than that without receiving the intervention (FIG. 7 at c-d). Similar results were also observed in the free DOX treated groups (FIG. 7 at e-f). FIG. 7 shows the influence of T-CeNP on 3D co-culture tumor spheroid of NIH3T3 cells and 4T1 cells (Green: GFP expressed NIH3T3 cells; Red: cell tracker deep red labeled 4T1 cells). Diagram and fluorescence images of cellular organization of NIH3T3 cells and 4T1 cells in their 3D co-culture tumor spheroid model a) or treated with T-CeNP b) every two days for 2 times. c) The fluorescence images of 3D co-culture tumor spheroid of NIH3T3 cells and 4T1 cells in different treatment. The co-culture tumor spheroids are pretreated with T-CeNP or not every two days for 2 time, and subsequently are treated with T-DOX@DMSN and free DOX at 1 mg/ml of DOX.

To probe whether the camouflage coating of the 4T1 cell membrane could boost the retention of DMSN in the primary and the metastatic tumors and to validate CAF reeducating effect of the T-CeNP could facilitate penetration of DMSN nanoparticle to the tumor tissue, both T-DMSN and N-DMSN were administrated to the mice bearing 4T1 orthotopic tumors with or without T-CeNP pretreatment. In vivo and ex vivo imaging indicated that the Cy5 signal in the tumor from the mice received T-DMSN treatment was higher than that from N-DMSN treated animal (FIG. 8 at a-b). In addition, pretreatment of T-CeNP significantly facilitated the tumor-specific retention of nanoparticles, both in the T-DMSN and N-DMSN groups. Interestingly, intra-tumor nanoparticles distribution (FIG. 8 at c) revealed that although the camouflage coating could increase nanoparticles retention in the tumor, a larger portion of them were located in peripheral areas. However, the pretreatment with T-CeNP significantly improved the penetration depth of the nanoparticles in the tumor mass (FIG. 8 at c), regardless of the camouflage coating with $CM^{4T1}$ or $CM^{CT26}$. Moreover, FIG. 8 at d showed that T-CeNP pretreatment could also boost the retention of free DOX in the tumor tissue. Besides increasing the retention of nanoparticles in the primary tumor, it is also revealed in FIG. 8 at e-f that the camouflage coating of 4T1 cells enhanced the accumulation of T-DMSN in the metastatic tumors in the lung due to the homologous targeting property.

To investigate the potential neoadjuvant chemotherapy and anti-metastatic effect of the T-CeNP for breast cancer surgery treatment, the 4T1-luc orthotopic tumor-bearing animals were treated as scheduled in FIG. 9A at a. Since the DOX dose adopted in the in vivo study was relatively lower than others reported, two weeks of free DOX treatment only slightly reduced the size of the primary tumor (FIG. 9A at b-c). As expected, the T-CeNP treatment alone did not affect the growth of the primary tumor. However, pretreatment of T-CeNP coupled with DOX enhanced the drug efficacy, both for free DOX and T-DOX. In addition, the T-DOX treated groups resulted in smaller primary tumors than their corresponding free drug counterparts, while the animals received both T-CeNP and T-DOX resulted in the best tumor burden reduction, evidenced by 35.8% lower than that of control (FIG. 9A at b-c), which paves the way for the following surgery.

To investigate the preventive effect of the T-CeNP on the post-surgery induced metastasis of breast cancer, the primary tumors were entirely removed by surgery (FIG. 17) 25 days post the inoculation and followed with another three rounds of combinatory treatment of T-CeNP and T-DOX as adjuvant chemotherapy. It was revealed that all the animals in the control group and the free DOX treated group developed lung metastasis (FIG. 9B at e). Interestingly, the three treatment groups included T-CeNP each had three lung metastasis-free animals. As previous research reported, that free DOX induced more metastasis nods in the lung (FIG. 9B at h-j). However, all 4T1 targeted nanoparticles, including both T-DOX and T-CeNP, significantly reduced the number of lung metastasis nodules.

Furthermore, the T-CeNP alone and T-CeNP coupled with T-DOX treatments exhibited the best preventive effect for lung metastasis, evidenced by 80.6% and 76.8% reduction compared to their corresponding controls, respectively. Besides inducing lung metastasis, DOX was also found to promote liver metastasis for breast cancer. See, A. Ouhtit, Z. Y. Abd Elmageed, M. E. Abdraboh, T. F. Lioe, M. H. Raj, *The American Journal Of Pathology* 2007. FIG. 9B at f-g confirmed the inductive effect of free DOX for liver metastasis. Similar to the preventive effect in the lung, all the nanoparticle treated groups exhibited fewer liver metastasis rate than the control. Furthermore, T-CeNP alone and T-CeNP coupled with T-DOX achieved the lowest liver metastasis rate, evidenced by 82.0% and 82.3% reduction of liver metastasis as compared with the non-treated control and free DOX treatment, respectively. Taken together, the combination of T-CeNP and T-DOX exhibited the highest potency for neoadjuvant chemotherapy and outstanding efficacy in inhibiting both lung and liver metastasis.

To probe the possible mechanism for T-CeNP exhibiting anti-metastatic effect, immunohistology assay was employed. It was revealed that, after receiving T-CeNP treatment, the expression of E-cadherin in the primary tumor tissue was upregulated, while the expression of fibronectin and α-SMA were downregulated (FIG. 18), suggesting the reeducation of CAF and reversion of the EMT process. Taken together, the results presented above indicated that the anti-metastatic effect of the T-CeNP was achieved through the remodeling of the TME. ROS attacks guanine bases in DNA and yields 8-hydroxydeoxyguanosine (8-OHdG). Thus, we measured the ROS level in the tumor treated with T-CeNP and control by fluorescent immunohistochemistry with the help of anti-8-OHdG antibody. FIG. S15, Supporting Information, proved that T-CeNP did inhibit ROS in the tumor tissue. Although a drug regimen of T-CeNP and T-DOX was used for the neoadjuvant chemotherapy of the primary cancer and preventive treatment of the metastasis, there is no apparent systemic toxicity after the treatment, as evidenced by the similar structure shown in the heart, liver, kidney, and spleen (FIG. 19). Furthermore, due to the relatively low dose of DOX, none of the treatments induced significant weight loss during the experiment (FIG. 9A at d). All these results suggest that the combination of T-CeNP and T-DOX could be a safe regimen for the treatment of breast cancer.

Since CAF plays a crucial role in the proliferation, migration, invasion, and metastasis of cancer cells, there is an urgent need for an approach that can inhibit cancer cell-induced CAF transdifferentiation and/or promote CAF reprogramming through reversed transdifferentiation from CAF to fibroblast. Benefit from its CAT and SOD mimicking activity (FIGS. 2A and 2B) and the homologous effect of the 4T1 cell membrane coating, T-CeNP exhibited a better preventive effect for the migration and invasion of 4T1 cells (FIGS. 3A and 3B). Furthermore, T-CeNP effectively prevented the transdifferentiation of fibroblast to CAF and reeducated the CAF back to normal fibroblast (FIGS. 5A, 5B, 6A, and 6B). Consequently, the co-culture of 4T1 cells with T-CeNP in $CMD^{CAF}$ and 4T1 cells in CMD generated from T-CeNP treated CAF displayed low migration and invasion tendency (FIGS. 5A and 5B). Moreover, T-CeNP also inhibited DOX-induced CAF transdifferentiation and facilitated the reprogramming of CAF back to normal fibroblast (FIGS. 6A and 6B). Tumor spheroid growth assay revealed that T-CeNP pretreatment could effectively limit the formation of a CAF based protective layer (FIG. 7), and resulted in a smaller 4T1 spheroid. In vivo biodistribution study found that the camouflage of 4T1 cell membrane boosted the retention of nanoparticles in the tumor tissue, especially for the animals pretreated with T-CeNP (FIG. 8). Consequently, as a neoadjuvant chemotherapy treatment, the combination of T-CeNP and T-DOX treatment resulted in the smallest primary tumor; as a preventive treatment, the combinatory regimen inhibited post-surgery lung metastasis and liver metastasis by 76.8% and 82.3%, respectively (FIGS. 9A and 9B). Further immunohistochemistry analysis validated our hypothesis that T-CeNP serves as a preventive tool for breast cancer lung metastasis through inhibiting CAF transdifferentiation and reeducating CAF (FIG. 18) and ROS in tumors. More importantly, due to the excellent biocompatibility and safety of the T-CeNP, no systemic toxicity was observed (FIG. 9A at d and FIG. 19).

In summary, biomimetic nanoparticles with the integration of a biodegradable dendritic mesoporous silica nanoparticle, SOD and CAT mimicking CeNPs or an anticancer drug, and the camouflage coating of cancer cell membrane have been developed for neoadjuvant chemotherapy and preventive therapy for post-surgery lung metastasis and liver metastasis of breast cancer. Accredited by the cancer cell membrane's homologous targeting effect, nanoparticles with camouflage coating were retained in the tumor. Through hindering CAF transdifferentiation and reeducating CAF, T-CeNP coupled with T-DOX effectively reduced the size of primary tumor and prevented the post-surgery lung metastasis and liver metastasis of breast cancer. Coupled with its outstanding safety, the combinatory regimen provides a new tool for the fight against breast cancer, especially for the preventing of post-surgical lung and liver metastasis.

Materials and Methods

Synthesis of Dendritic Mesoporous Organosilica Nanoparticles (DMSN)

One-pot synthesis method was used to synthesis DMSN, where Cetyltrimethylammonium bromide (CTAB) and sodium salicylate (NaSal) were as a structure directing agent, Tetraethyl orthosilicate (TEOS) and 1,2-Bis(triethoxysilyl)ethane (BTEE) as a silica source and triethanolamine (TEA) as a catalyst. Typically, 25 ml of deionized water containing 68 mg TEA was gently stirred and heated to 80° C. in an oil bath. After 0.5 h heating, 380 mg CTAB and 84 mg NaSal were added to the stirring solution and keep the gently stirring for another 1 h. Then, a mixed solution of 2 ml TEOS and 1.6 ml BTEE was dropwise added into the solution and keeping gently stirring for 12 h. After that, the product was collected by centrifugation (15000 rcf, 20 min) and washed 3 time with methanol. The collected product was dispersed in 10 mg/ml of ammonium nitrate methanol solution and sonicated in a bath ultrasonic for 3 h for 3 times to remove CTAB and NaSal template, the obtained DMSN was dispersed in methanol for future use.

Cell Membrane Vesicles (CM) Preparation

4T1 cells or CT 26 were maintained in DMEM medium containing 10% FBS and penicillin-streptomycin. After growing to full confluency, the cells were harvested with 2 mM ethylenediaminetetraacetic acid (EDTA) PBS solution and washed three times with PBS by centrifuging (1000 rcf, 10 min). Then the collected cells were suspended in pre-cooled hypotonic lysing buffer (20 mM Tris-HCl pH7.4, 10 mM KCl, 2 mM $MgCl_2$ and 1 EDTA-free mini protease inhibitor tablet per 10 ml) and disrupted using a Dounce homogenizer at least 20 passes before spinning down at 3000 rcf for 10 min. The supernatant was collected and centrifuged at 10,000 rcf for 10 min, after the pellet was discarded and the supernatants was further centrifuged at 100,000 rcf for 1 h. The collected membrane pellet was wash once with 10 mM Tris-HCl (pH=7.5), centrifuged, and resuspend in water. Finally, the cell membrane ghosts were sonicated 30 s and physically extruded through a 400 nm polycarbonate membrane for 5 circles to obtain the cancer cell membrane vesicles (CM). The obtained CM was stored at 4° C. until further use, and the protein in the solution was quantified by using BCA protein assay.

Fabrication of CeNP or DOX Loaded and CM Cloaked DMSN

To load CeNP into DMSN, 2 ml of CeNP (240 mg/ml) was dropwise added into 10 ml of DMSN ethanol solution (20 mg/ml) under stirring, then the solution was sonicated for 1 min in a bath ultrasonic and gently stirred for 24 h. The CeNP loaded DMSN (CeNP@DMSN) was collected by centrifugation (14,000 g, 20 min) and washed with water for 3 time. For the loading of DOX, 2 ml of 2 mg/ml DOX in PBS was dropwise added into 10 mg/ml DMSN PBS solution under gently stirring, then the mixture solution was sonicated 1 min in a bath ultrasonicator and gently stirred for 24 h in dark. Finally, the DOX loaded DMSN (DOX@DMSN) was obtained by centrifugation (14,000 g, 20 min) and wash with water for 3 time. To fabricated CM cloaked and drug loaded DMSN, DMSN, CeNP@DMSN or DOX@DMSN solution was added to CM at varying weight ration of protein to DMSN, the mixtures were sonicated for 30 s and then extruded through a 200 nm polycarbonate membranes for 11 passes to obtain cell membrane cloaked DMSN@CM, CeNP@DMSN@CM, and DOX@DMSN@CM.

Characterization of the Nanoparticles

The morphologies of the prepared nanoparticles were characterized by transmission electron microscope (Hitachi HT7800 TEM, Hitachi High Technologies, Tokyo, Japan). The hydrodynamic sizes and zeta potentials of the nanoparticles were measured by Nano ZS Zetasizer (Malvern Instruments, UK). The drug loading efficiency and encapsulation efficiency were measured by using UV-VIS spectroscopy with Free CeNP and DOX as standard. The cell membrane protein composition of the NP was characterized by sodium dodecylsulfate polyacrylamide gel electrophoresis (SDS-PAGE) and stained with Coomassie brilliant blue (Invitrogen, Oregon, USA) method.

Catalase Mimetic Activity and SOD Mimetic Activity

The catalase activity of Free CeNP and T-CeNP was assessed by colorimetric assay based on the reaction of ammonium metavanadate with $H_2O_2$. Under acidic conditions, vanadium (V) was reduced to vanadium (III) by $H_2O_2$ to produce a red orange peroxovanadium complex, which had an obvious absorbance peak at 452 nm. In brief, free CeNP or T-CeNP was incubated with 10 mM $H_2O_2$ in PBS for 10 min. Subsequently, same volume of ammonium metavanadate (0.01 M) in sulfuric acid (0.5 M) was added to the reaction solution to determine the remaining $H_2O_2$. Catalase was used as a standard reagent for the evaluation of the catalase activity of CeNP. The SOD mimetic activity of free CeNP and T-CeNP was assessed using Superoxide Dismutase Assay Kit (Cayman Chemical, Ann Arbor, MI) according to the manufacturer's manual, SOD was used as standard reagent.

Cell Culture

Murine mammary carcinoma 4T1 cells, murine colon carcinoma CT26 cells, and NIH/3T3 mouse fibroblast cells were obtained from American Type Culture Collection (ATCC, Manassas, VA, USA). The cells were cultured in Dulbecco's Modified Eagle's Medium (DMEM) containing 10% of fetal bovine serum (FBS, Gibco), 100 U/mL of penicillin and 100 mg/mL of streptomycin under a humidified atmosphere of 5% CO2 at 37° C. The culture medium was replaced with fresh one every two days unless specially mentioned.

The Cellular Uptake of DMSN@CM and Intracellular Co-Localization of CM and DMSN

To investigate the cellular internalization of $DMSN@CM^{4T1}$ and $DMSN@CM^{CT26}$, DMSN was labeled with cyanine5 (cy5) through the reaction between mercaptopropyl trimethoxysilane (MPTS) and cyanine5 maleimide. 4T1 cells were cultured in 35 mm glass bottom dishes at a density 4×104/well. After 24 h of culture, the medium was replaced with a fresh complete medium containing 10 μg/ml of Cy5 labeled NP. After 2 h of incubation, the cells were washed 3 times with cold PBS and fixed with 4% paraformaldehyde for 15 min. The nuclei were stained with 10 μg/ml of Hoechst 33254 for 10 min at room time. The uptake of nanoparticles was observed with fluorescence microscope (Evos™ FL, ThermoFisher Scientific, MA, USA). To investigate the intracellular co-localization of cancer cell membrane and DMSN, DMSN was labeled with Cy5 and cancer cell membrane was stained with CellTracker™ Green (Invitrogen) before extrusion. After 4T1 cells were treated with di-stained DMSN@CM$^{4T1}$ for 1 h, the cells were washed 3 times with cold PBS, fixed with 4% paraformaldehyde for 15 min and the nuclei were stained with Hoechst 33254 for 10 min before imaging with CLSM microscope (Carl Zeiss LSM 700 Confocal Microscope, Oberkochen, Germany).

In Vitro Cytotoxicity Assay

To investigate the cytotoxicity of CeNP, 4T1 and NIH3T3 cells were seeded in 96-well plates (7,500 cells/well) and cultured for 24 h. Then the medium was replaced with a fresh medium containing free CeNP of different concentrations. After 48 h of incubation, 10 μl of MTT solution (5 mg/ml in PBS) was added to each well and incubated for another 4 h, then the medium was discarded and replaced with 100 μl of DMSO. The optical density (OD) of each well was measured by using a microplate reader at 570 nm, and untreated cells were used as controls. The cell viability was calculated as the following formula: $OD_A/OD_B \times 100\%$, where $OD_A$ is the OD value of experimental group cells, and $OD_B$ is the OD value of control cells. To investigate influence of CeNP on the cytotoxicity of DOX to 4T1 and NIH3T3 cells, the cells were pretreated with varying concentration of CeNP for 24 h followed treating a constant concentration of DOX@DMSN for 48 h, then the cell ability was measured as aforementioned MTT method. To investigate the cytotoxicity of free DOX and DOX loaded NP, 4T1 cells were pretreated with or without 100 μM of CeNP@DMSN@CM for 24 h, followed by treating with varied concentrations of free DOX, DOX@DMSN@CM$^{4T1}$ and DOX@DMSN@CM$^{CT26}$. After 4 h of incubation, the medium containing drug was replaced with fresh medium, and the cells were cultured for another 48 h followed by MTT assay.

Preparation of Conditioned Medium (CMD) from Different Cell Lines

Cells were seeded in complete growth medium on 25 cm$^2$ culture dishes until reaching 90% confluence. The cells were washed twice with PBS briefly and cultured in serum-free medium for another 48 h. After that, the conditioned medium (CM) was collected, centrifuged at 1,500 rcf for 10 min to remove cell debris, sterile filtered with 0.45 μm filter and stored at −80° C. for future use.

Establishment and Confirmation of Cancer-Associated Fibroblast (CAF) from NIH3T3 Cells NIH-3T3 cells were seeded in a complete growth medium on 25 cm$^2$ culture dish. Once reaching 70 confluence, the cells were starved with 0.5% FBS containing medium for 24 hours, and then the medium was changed to CMD derived from 4T1 cells (CMD$^{4T1}$) for another 48 hours culture. To confirm the generation of CAF, western blot analysis and immunofluorescence staining for a-SMA and fibronectin was performed. CAF cells were seeded in complete growth medium until reaching 70% confluence followed by treating with 100 μM of CeNP@DMSN@CM for 48 h, then were performed western blotting and immunofluorescence stain for a-SMA and fibronectin expression to assess the reprogram effect of CeNP on CAF.

Western Blot

Cells were harvested and lysed in the RIPA buffer containing 1% cocktail protease inhibitor for 30 min on ice. The total proteins were collected and quantified by BCA assay. Then proteins were separated by 10% of SDS-PAGE electrophoresis and blotted onto a PVDF membrane. After the membrane was blocked with 5% of fat-free dry milk solution in TBST for 1 h, the membrane was incubated with primary antibodies against a-SMA, fibronectin, and β-actin overnight at 4° C., and the membranes were washed with TBST and incubated with the secondary antibodies for 1 h. Enhanced chemiluminescence was used to detect the targeted protein expression. β-actin was used as an internal reference protein.

Immunofluorescence Staining

Immunofluorescence staining was performed to detect the expression of α-SMA, fibronectin, and E-cadherin on different fibroblasts and the secretion of fibronectin from them. In brief, after different treatment, the cells were rinsed with PBS for 3 times and fixed in 4% paraformaldehyde for 15 min and then permeabilized in 0.1% Triton X-100 for 10 min. Then the cells were washed with PBS for 3 times, blocked in 5% BSA in PBS solution for 1 hour at room temperature and incubated with primary antibodies overnight at 4° C. The cells were then washed with PBS for 3 times and incubated with PE-conjugated secondary antibodies.

The nuclei were stained using Hoechst 3342. The protein expression was observed with a fluorescence microscope (Evos™ FL, ThermoFisher Scientific, MA, USA).

Wound Healing Assay

4T1 cells were plated in six-well plates at 50,000 cells per well to grow into a completely confluent monolayer. Then a linear scratch/wound was made with a sterile 200 μl pipette tip on the cell monolayer. After gently washing with PBS for 3 time, the cells were incubated in CMD derived from different cells and serum-free medium containing various nanoparticles in different concentrations, including free CeNP and CeNP@DMSN@CM$^{4T1}$. The migrated distance in different groups was observed and imaged at predesigned time intervals.

Cell Invasion Assay

4T1 cells (250,000/ml) in 200 μl of CMD derived from different cells or in serum-free medium containing various nanoparticles were added to the upper chamber (6.5 mm diameter, 8 μm pore size, Millipore). Complete medium (600 μl) containing 10% FBS was added to the lower chamber. The cells were left to migrate the Transwell membrane for 20 h. The non-invaded cells on the upper surface of the membrane were removed by wiping with a cotton swab, and the invaded cells were fixed, stained with crystal violet and counted under a microscope for each membrane in three randomly selected fields.

ELIAS of TGF-β

The TGF-β content in the CMD of 4T1 and NIH-3T3/CAF undergone different treatments was quantitively measured by Human/Mouse TGF-beta ELIAS kit (Invitrogen, USA) according to the manufacturer's manual. The total protein in cells was quantified using a BCA assay.

Co-Culture of 4T1 and NIH/3T3 Cells

NIH-3T3 cells stably expressing GFP (NIH 3T3/GFP) and 4T1 cells were co-cultured in 35 mm glass-bottom dishes at 1:2 ratio (total number: 6×104/well). After 48 h of incubation, the co-cultured cells were treated with 100 μM T-CeNP for another 48 h, followed by immunofluorescence staining of E-cadherin and fibronectin to investigate the influence of T-CeNP on EMT of 4T1 cells and differentiation and transdifferentiation of CAF in the co-culture model.

4T1 and NIH/3T3 Co-Cultured 3D Tumor Spheroid (TS)

To track cells and characterize tumor spheroid, NIH 3T3/GFP and 4T1 cells labeled with CellTracker™ Deep Red Dye (Invitrogen, USA) were used to generate the TS. Briefly, 4T1 and NIH 3T3/GFP cells at 1:1 ratio (3,000 4T1 cells and 3,000 NIH 3T3/GFP cells in 100 μL of DMEM) were seeded in 96-well ultra-low-attachment (ULA) plates (Corning, MA, USA). Different treatments, including free DOX, T-DOX, and T-CeNP, were added to the culture medium after 48 h of incubation or till the formation of spheroids. The morphology and characterization of TS was observed and imaged using fluorescence microscope every 24 h (Evos™ FL, ThermoFisher Scientific, MA, USA).

Orthotopic Breast Cancer Model, Neoadjuvant Chemotherapy and Surgery

The 4T1 orthotopic model was established following our previous method with a minor modification. All animal experiments were conducted in accordance with NIH regulations and approved by the Institutional Animal Care and Use Committee of the University of South Carolina. 4T1/Luc2 cells ($2 \times 10^5$ in 20 μl PBS) were injected into the right 4th mammary fat pad of 6-8 weeks female BALB/c mice, and the primary tumor growth was monitored through bioluminescence signal using IVIS imaging system. Two weeks post tumor cell inoculation, the mice were randomly divided into 6 groups (n=10), including control, T-CeNP, T-DOX, free DOX, T-CeNP+T-DOX, and T-CeNP+ Free DOX, and received corresponding neoadjuvant chemotherapy, surgery, and postoperative chemotherapy. The detailed therapeutic regimen and time schedule were presented in FIG. 8A. In brief, for neoadjuvant chemotherapy, the drugs were intravenously injected at a CeNP dosage of 1 mg/kg and DOX dosage of 3 mg/kg every 3 days for 4 times. Specifically, for the groups of T-CeNP+T-DOX and T-CeNP+ free DOX, T-CeNP was administrated to mice 2 days prior to T-DOX or Free DOX treatment. Two days after the last dose, all mice underwent complete surgical removal of the tumors following our previous method. Two days after the surgery, the mice received another 3 times administration of T-CeNP, T-DOX, free DOX, and their combination as post-surgical chemotherapy. At the end of the study (day 24), the mice were sacrificed, and the lung and liver were harvested for ex vivo bioluminescence imaging to examine the metastasis.

Biodistribution of Nanoparticles in 4T1 Tumor-Bearing Mice

Ten days after the 4T1 orthotopic tumor implantation, the mice were iv injected with T-CeNP at a CeNP dose of 1 mg/kg or saline (as control) every 3 days for 3 times. At day 20, the control mice and T-CeNP pretreated mice were divided into 2 groups and were injected with Cy5 labeled T-DMSN and N-DMSN at a Cy5 dose of 0.5 mg/kg via tail vein, respectively. Six hour later, the mice were intraperitoneally injected with d-luciferin (150 mg/kg), and imaged using an IVIS Lumina III whole body imaging system (PerkinElmer Inc., Waltham, USA) (excitation: 630 nm, emission: 650-670 nm). Following the in vivo imaging, the mice were sacrificed, and the tumors and main organs were dissected for ex vivo imaging. For further determining intra-tumoral distribution of nanoparticles, the tumors were frozen sliced for immunofluorescence imaging by Evos FL Auto 2 (Invitrogen, USA) (excitation: 628 nm, emission: 692 nm).

To evaluate the influence of pretreatment with T-CeNP on the accumulation of free DOX in tumor, the DOX content in tumor tissue harvested from free DOX group and T-CeNP+ free DOX group during surgery was quantitively analyzed using the fluorescence method. Briefly, ~100 mg of tumor tissue was weighted and mechanically homogenized in 400 μl of nuclear lysis buffer [250 mM sucrose, 5 mM Tris-HCl, 1 mM MgSO4, 1 mM $CaCl_2$ (pH 7.6)]. Then 100 μl of homogenate was mixed with 900 μl of extraction reagent (0.075 N HCl 90% 2-propanol) and storage at −20° C. for 12 hours. After that, the extraction mixture was centrifuged at 12,000 g for 15 min, and the supernatant was collected to quantitively measure the concentration of DOX fluorometrically (excitation: 490 nm, emission: 550 nm).

To investigate nanoparticles distribution in lung metastases from 4T1 breast cancer, a lung metastasis model of murine mammary carcinoma 4T1 was established according to our previous reported method. Two weeks after the inoculation of cancer cells, healthy mice and the mice with lung metastasis were i.v. injected with Cy5 labeled T-DMSN and N-DMSN at a Cy5 dose of 0.5 mg/kg. The mice were intraperitoneally injected with firefly d-luciferin (150 mg/kg) 6 h later. Five minute later, the mice were sacrificed, and the lungs and other major organs were harvested for ex vivo bioluminescence and fluorescence imaging. The lungs were further frozen sliced for fluorescence imaging using a Carl Zeiss LSM700 confocal microscope to visualize nanoparticles distribution in the lung.

Histology and Immunohistochemistry Analysis

The harvested tumors and major organs were fixed with 4% paraformaldehyde and processed by paraffin sectioning and frozen sectioning. Tissue sections (heart, liver, spleen, and kidney) and lung sections were hematoxylin and eosin (H&E) stained for acute toxicity evaluation and lung metastasis evaluation. The tumor sections were immunofluorescence stained with specific primary antibody, including rabbit anti-α-SMA antibody, rabbit anti-fibronectin antibody, and rabbit anti-E-cadherin antibody for the evaluation of CAF, ECM, and EMT, respectively. All the immunofluorescence images were recorded with a fluorescence microscope (Evos™ FL, ThermoFisher Scientific, MA, USA).

Statistical Analysis

GraphPad Prism 6.0 software (La Jolla, CA) was used to conduct statistical analysis. Differences between groups were examined using Student's t-test or ANOVA with Tukey's multiple comparison tests. When p-value was less than 0.05, the differences were considered significant (*<0.05, <0.01,*<0.001).

Sequence Listing

The following proteins are hereby designated in the contemporaneously filed Sequence Listing, which is hereby incorporated by reference:

```
TGFβ1-SEQ ID NO: 1
IL6-SEQ ID NO: 2
HMGB1-SEQ ID NO: 3
DHX15-SEQ ID NO: 4
Ecadherin-SEQ ID NO: 5
Fibronectin-SEQ ID NO: 6
SEQUENCE LISTING-USC 2033101.0000262
<110> University of South Carolina
<120> Nanoparticle For The Remodeling Of Cancer
Associated Fibroblasts
<130> 2033101.0000392
```

-continued

```
<140> Unknown
<141> 2022 Oct. 14
<150> U.S. Provisional Application No. 63/289,265
<151> 2021 Dec. 14
<160> 6
<170> PatentIn Version 3.5
<210> 1
<211> 390
<212> PRT
<213> Homo sapiens
<400> 1
MetProProSerGlyLeuArgLeuLeuLeuLeuLeuProLeuLeuTrpLeuLeuVal LeuThrProGlyArgProAlaAlaGlyLeuSerThrCysLysThrIleAspMetGluLeu ValLysArgLysArgIleGluAlaIleArgGlyGlnIleLeuSerLysLeuArgLeuAla SerProProSerGlnGlyGluValProProGlyProLeuProGluAlaValLeuAlaLeu TyrAsnSerThrArgAspArgValAlaGlyGluSerAlaGluProGluProGluProGlu AlaAspTyrTyrAlaLysGluValThrArgValLeuMetValGluThrHisAsnGluIle TyrAspLysPheLysGlnSerThrHisSerIleTyrMetPhePheAsnThrSerGluLeu ArgGluAlaValProGluProValLeuLeuSerArgAlaGluLeuArgLeuLeuArgLeu LysLeuLysValGluGlnHisValGluLeuTyrGlnLysTyrSerAsnAsnSerTrpArg TyrLeuSerAsnArgLeuLeuAlaProSerAspSerProGluTrpLeuSerPheAspVal ThrGlyValValArgGlnTrpLeuSerArgGlyGlyGluIleGluGlyPheArgLeuSer AlaHisCysSerCysAspSerArgAspAsnThrLeuGlnValAspIleAsnGlyPheThr ThrGlyArgArgGlyAspLeuAlaThrIleHisGlyMetAsnArgProPheLeuLeuLeu MetAlaThrProLeuGluArgAlaGlnHisLeuGlnSerSerArgHisArgArgAlaLeu AspThrAsnTyrCysPheSerSerThrGluLysAsnCysCysValArgGlnLeuTyrIle AspPheArgLysAspLeuGlyTrpLysTrpIleHisGluProLysGlyTyrHisAlaAsn PheCysLeuGlyProCysProTyrIleTrpSerLeuAspThrGlnTyrSerLysValLeu AlaLeuTyrAsnGlnHisAsnProGlyAlaSerAlaAlaProCysCysValProGlnAla LeuGluProLeuProIleValTyrTyrValGlyArgLysProLysValGluGlnLeuSer AsnMetIleValArgSerCysLysCysSer <210> 2
<211> 212
<212> PRT
<213> Homo sapiens
<400> 2
MetAsnSerPheSerThrSerAlaPheGlyProValAlaPheSerLeuGlyLeuLeuLeu ValLeuProAlaAlaPheProAlaProValProProGlyGluAspSerLysAspValAla AlaProHisArgGlnProLeuThrSerSerGluArgIleAspLysGlnIleArgTyrIle LeuAspGlyIleSerAlaLeuArgLysGluThrCysAsnLysSerAsnMetCysGluSer SerLysGluAlaLeuAlaGluAsnAsnLeuAsnLeuProLysMetAlaGluLysAspGly CysPheGlnSerGlyPheAsnGluGluThrCysLeuValLysIleIleThrGlyLeuLeu GluPheGluValTyrLeuGluTyrLeuGlnAsnArgPheGluSerSerGluGluGlnAla ArgAlaValGlnMetSerThrLysValLeuIleGlnPheLeuGlnLysLysAlaLysAsn LeuAspAlaIleThrThrProAspProThrThrAsnAlaSerLeuLeuThrLysLeuGln AlaGlnAsnGlnTrpLeuGlnAspMetThrThrHisLeuIleLeuArgSerPheLysGlu PheLeuGlnSerSerLeuArgAlaLeuArgGlnMet
```

<210> 3
<211> 215
<212> PRT
<213> Homo sapiens
<400> 3
MetGlyLysGlyAspProLysLysProArgGlyLysMetSerSerTyrAlaPhePheVal GlnThrCysArgGluGluHisLysLysLysHisProAspAlaSerValAsnPheSerGlu PheSerLysLysCysSerGluArgTrpLysThrMetSerAlaLysGluLysGlyLysPhe GluAspMetAlaLysAlaAspLysAlaArgTyrGluArgGluMetLysThrTyrIlePro ProLysGlyGluThrLysLysLysPheLysAspProAsnAlaProLysArgProProSer AlaPhePheLeuPheCysSerGluTyrArgProLysIleLysGlyGluHisProGlyLeu SerIleGlyAspValAlaLysLysLeuGlyGluMetTrpAsnAsnThrAlaAlaAspAsp LysGlnProTyrGluLysLysAlaAlaLysLeuLysGluLysTyrGluLysAspIleAla AlaTyrArgAlaLysGlyLysProAspAlaAlaLysLysGlyValValLysAlaGluLys SerLysLysLysLysGluGluGluGluAspGluGluAspGluGluAspGluGluGluGlu GluAspGluGluAspGluAspGluGluGluAspAspAspAspGlu <210> 4
<211> 795
<212> PRT
<213> Homo sapiens
<400> 4
MetSerLysArgHisArgLeuAspLeuGlyGluAspTyrProSerGlyLysLysArgAla GlyThrAspGlyLysAspArgAspArgAspArgGluAspArgSerLysAspArg AspArgGluArgAspArgGlyAspArgGluArgGluLysGluLysGluLysGlu LeuArgAlaSerThrAsnAlaMetLeuIleSerAlaGlyLeuProProLeuLysAlaSer HisSerAlaHisSerThrHisSerAlaHisSerThrHisSerThrHisSerAlaHisSer ThrHisAlaGlyHisAlaGlyHisThrSerLeuProGlnCysIleAsnProPheThrAsn LeuProHisThrProArgTyrTyrAspIleLeuLysLysArgLeuGlnLeuProValTrp GluTyrLysAspArgPheThrAspIleLeuValArgHisGlnSerPheValLeuValGly GluThrGlySerGlyLysThrThrGlnIleProGlnTrpCysValGluTyrMetArgSer LeuProGlyProLysArgGlyValAlaCysThrGlnProArgArgValAlaAlaMetSer ValAlaGlnArgValAlaAspGluMetAspValMetLeuGlyGlnGluValGlyTyrSer IleArgPheGluAspCysSerSerAlaLysThrIleLeuLysTyrMetThrAspGlyMet LeuLeuArgGluAlaMetAsnAspProLeuLeuGluArgTyrGlyValIleIleLeuAsp GluAlaHisGluArgThrLeuAlaThrAspIleLeuMetGlyValLeuLysGluValVal ArgGlnArgSerAspLeuLysValIleValMetSerAlaThrLeuAspAlaGlyLysPhe GlnIleTyrPheAspAsnCysProLeuLeuThrIleProGlyArgThrHisProValGlu IlePheTyrThrProGluProGluArgAspTyrLeuGluAlaAlaIleArgThrValIle GlnIleHisMetCysGluGluGluGluGlyAspLeuLeuLeuPheLeuThrGlyGlnGlu GluIleAspGluAlaCysLysArgIleLysArgGluValAspAspLeuGlyProGluVal GlyAspIleLysIleIleProLeuTyrSerThrLeuProProGlnGlnGlnGlnArgIle PheGluProProProProLysLysGlnAsnGlyAlaIleGlyArgLysValValValSer ThrAsnIleAlaGluThrSerLeuThrIleAspGlyValValPheValIleAspProGly PheAlaLysGlnLysValTyrAsnProArgIleArgValGluSerLeuLeuValThrAla IleSerLysAlaSerAlaGlnGlnArgAlaGlyArgAlaGlyArgThrArgProGlyLys -continued CysPheArgLeuTyrThrGluLysAlaTyrLysThrGluMetGlnAspAsnThrTyrPro GluIleLeuArgSerAsnLeuGlySerValValLeuGlnLeuLysLysLeuGlyIleAsp AspLeuValHisPheAspPheMetAspProProAlaProGluThrLeuMetArgAlaLeu GluLeuLeuAsnTyrLeuAlaAlaLeuAsnAspAspGlyAspLeuThrGluLeuGlySer MetMetAlaGluPheProLeuAspProGlnLeuAlaLysMetValIleAlaSerCysAsp TyrAsnCysSerAsnGluValLeuSerIleThrAlaMetLeuSerValProGlnCysPhe ValArgProThrGluAlaLysLysAlaAlaAspGluAlaLysMetArgPheAlaHisIle AspGlyAspHisLeuThrLeuLeuAsnValTyrHisAlaPheLysGlnAsnHisGluSer ValGlnTrpCysTyrAspAsnPheIleAsnTyrArgSerLeuMetSerAlaAspAsnVal ArgGlnGlnLeuSerArgIleMetAspArgPheAsnLeuProArgArgSerThrAspPhe ThrSerArgAspTyrTyrIleAsnIleArgLysAlaLeuValThrGlyTyrPheMetGln ValAlaHisLeuGluArgThrGlyHisTyrLeuThrValLysAspAsnGlnValValGln LeuHisProSerThrValLeuAspHisLysProGluTrpValLeuTyrAsnGluPheVal LeuThrThrLysAsnTyrIleArgThrCysThrAspIleLysProGluTrpLeuValLys IleAlaProGlnTyrTyrAspMetSerAsnPheProGlnCysGluAlaLysArgGlnLeu AspArgIleIleAlaLysLeuGlnSerLysGluTyrSerGlnTyr <210> 5
<211> 882
<212> PRT
<213> Homo sapiens
<400> 5
etGlyProTrpSerArgSerLeuSerAlaLeuLeuLeuLeuLeuGlnValSerSerTrp LeuCysGlnGluProGluProCysHisProGlyPheAspAlaGluSerTyrThrPheThr ValProArgArgHisLeuGluArgGlyArgValLeuGlyArgValAsnPheGluAspCys ThrGlyArgGlnArgThrAlaTyrPheSerLeuAspThrArgPheLysValGlyThrAsp GlyValIleThrValLysArgProLeuArgPheHisAsnProGlnIleHisPheLeuVal TyrAlaTrpAspSerThrTyrArgLysPheSerThrLysValThrLeuAsnThrValGly HisHisHisArgProProProHisGlnAlaSerValSerGlyIleGlnAlaGluLeuLeu ThrPheProAsnSerSerProGlyLeuArgArgGlnLysArgAspTrpValIleProPro IleSerCysProGluAsnGluLysGlyProPheProLysAsnLeuValGlnIleLysSer AsnLysAspLysGluGlyLysValPheTyrSerIleThrGlyGlnGlyAlaAspThrPro ProValGlyValPheIleIleGluArgGluThrGlyTrpLeuLysValThrGluProLeu AspArgGluArgIleAlaThrTyrThrLeuPheSerHisAlaValSerSerAsnGlyAsn AlaValGluAspProMetGluIleLeuIleThrValThrAspGlnAsnAspAsnLysPro GluPheThrGlnGluValPheLysGlySerValMetGluGlyAlaLeuProGlyThrSer ValMetGluValThrAlaThrAspAlaAspAspAspValAsnThrTyrAsnAlaAlaIle AlaTyrThrIleLeuSerGlnAspProGluLeuProAspLysAsnMetPheThrIleAsn ArgAsnThrGlyValIleSerValValThrThrGlyLeuAspArgGluSerPheProThr TyrThrLeuValValGlnAlaAlaAspLeuGlnGlyGluGlyLeuSerThrThrAlaThr AlaValIleThrValThrAspThrAsnAspAsnProProIlePheAsnProThrThrTyr LysGlyGlnValProGluAsnGluAlaAsnValValIleThrThrLeuLysValThrAsp AlaAspAlaProAsnThrProAlaTrpGluAlaValTyrThrIleLeuAsnAspAspGly GlyGlnPheValValThrThrAsnProValAsnAsnAspGlyIleLeuLysThrAlaLys -continued GlyLeuAspPheGluAlaLysGlnGlnTyrIleLeuHisValAlaValThrAsnValVal ProPheGluValSerLeuThrThrSerThrAlaThrValThrValAspValLeuAspVal AsnGluAlaProIlePheValProProGluLysArgValGluValSerGluAspPheGly ValGlyGlnGluIleThrSerTyrThrAlaGlnGluProAspThrPheMetGluGlnLys IleThrTyrArgIleTrpArgAspThrAlaAsnTrpLeuGluIleAsnProAspThrGly AlaIleSerThrArgAlaGluLeuAspArgGluAspPheGluHisValLysAsnSerThr TyrThrAlaLeuIleIleAlaThrAspAsnGlySerProValAlaThrGlyThrGlyThr LeuLeuLeuIleLeuSerAspValAsnAspAsnAlaProIleProGluProArgThrIle PhePheCysGluArgAsnProLysProGlnValIleAsnIleIleAspAlaAspLeuPro ProAsnThrSerProPheThrAlaGluLeuThrHisGlyAlaSerAlaAsnTrpThrIle GlnTyrAsnAspProThrGlnGluSerIleIleLeuLysProLysMetAlaLeuGluVal GlyAspTyrLysIleAsnLeuLysLeuMetAspAsnGlnAsnLysAspGlnValThrThr LeuGluValSerValCysAspCysGluGlyAlaAlaGlyValCysArgLysAlaGlnPro ValGluAlaGlyLeuGlnIleProAlaIleLeuGlyIleLeuGlyGlyIleLeuAlaLeu LeuIleLeuIleLeuLeuLeuLeuLeuPheLeuArgArgArgAlaValValLysGluPro LeuLeuProProGluAspAspThrArgAspAsnValTyrTyrTyrAspGluGluGlyGly GlyGluGluAspGlnAspPheAspLeuSerGlnLeuHisArgGlyLeuAspAlaArgPro GluValThrArgAsnAspValAlaProThrLeuMetSerValProArgTyrLeuProArg ProAlaAsnProAspGluIleGlyAsnPheIleAspGluAsnLeuLysAlaAlaAspThr AspProThrAlaProProTyrAspSerLeuLeuValPheAspTyrGluGlySerGlySer GluAlaAlaSerLeuSerSerLeuAsnSerSerGluSerAspLysAspGlnAspTyrAsp TyrLeuAsnGluTrpGlyAsnArgPheLysLysLeuAlaAspMetTyrGlyGlyGlyGlu AspAsp <210> 6
<211> 2386
<212> PRT
<213> Homo sapiens
<400> 6
MetLeuArgGlyProGlyProGlyLeuLeuLeuLeuAlaValGlnCysLeuGlyThrAla ValProSerThrGlyAlaSerLysSerLysArgGlnAlaGlnGlnMetValGlnProGln SerProValAlaValSerGlnSerLysProGlyCysTyrAspAsnGlyLysHisTyrGln IleAsnGlnGlnTrpGluArgThrTyrLeuGlyAsnAlaLeuValCysThrCysTyrGly GlySerArgGlyPheAsnCysGluSerLysProGluAlaGluGluThrCysPheAspLys TyrThrGlyAsnThrTyrArgValGlyAspThrTyrGluArgProLysAspSerMetIle TrpAspCysThrCysIleGlyAlaGlyArgGlyArgIleSerCysThrIleAlaAsnArg CysHisGluGlyGlyGlnSerTyrLysIleGlyAspThrTrpArgArgProHisGluThr GlyGlyTyrMetLeuGluCysValCysLeuGlyAsnGlyLysGlyGluTrpThrCysLys ProIleAlaGluLysCysPheAspHisAlaAlaGlyThrSerTyrValValGlyGluThr TrpGluLysProTyrGlnGlyTrpMetMetValAspCysThrCysLeuGlyGluGlySer GlyArgIleThrCysThrSerArgAsnArgCysAsnAspGlnAspThrArgThrSerTyr ArgIleGlyAspThrTrpSerLysLysAspAsnArgGlyAsnLeuLeuGlnCysIleCys ThrGlyAsnGlyArgGlyGluTrpLysCysGluArgHisThrSerValGlnThrThrSer SerGlySerGlyProPheThrAspValArgAlaAlaValTyrGlnProGlnProHisPro -continued GlnProProProTyrGlyHisCysValThrAspSerGlyValValTyrSerValGlyMet
GlnTrpLeuLysThrGlnGlyAsnLysGlnMetLeuCysThrCysLeuGlyAsnGlyVal
SerCysGlnGluThrAlaValThrGlnThrTyrGlyGlyAsnSerAsnGlyGluProCys
ValLeuProPheThrTyrAsnGlyArgThrPheTyrSerCysThrThrGluGlyArgGln
AspGlyHisLeuTrpCysSerThrThrSerAsnTyrGluGlnAspGlnLysTyrSerPhe
CysThrAspHisThrValLeuValGlnThrArgGlyGlyAsnSerAsnGlyAlaLeuCys
HisPheProPheLeuTyrAsnAsnHisAsnTyrThrAspCysThrSerGluGlyArgArg
AspAsnMetLysTrpCysGlyThrThrGlnAsnTyrAspAlaAspGlnLysPheGlyPhe
CysProMetAlaAlaHisGluGluIleCysThrThrAsnGluGlyValMetTyrArgIle
GlyAspGlnTrpAspLysGlnHisAspMetGlyHisMetMetArgCysThrCysValGly
AsnGlyArgGlyGluTrpThrCysIleAlaTyrSerGlnLeuArgAspGlnCysIleVal
AspAspIleThrTyrAsnValAsnAspThrPheHisLysArgHisGluGluGlyHisMet
LeuAsnCysThrCysPheGlyGlnGlyArgGlyArgTrpLysCysAspProValAspGln
CysGlnAspSerGluThrGlyThrPheTyrGlnIleGlyAspSerTrpGluLysTyrVal
HisGlyValArgTyrGlnCysTyrCysTyrGlyArgGlyIleGlyGluTrpHisCysGln
ProLeuGlnThrTyrProSerSerSerGlyProValGluValPheIleThrGluThrPro
SerGlnProAsnSerHisProIleGlnTrpAsnAlaProGlnProSerHisIleSerLys
TyrIleLeuArgTrpArgProLysAsnSerValGlyArgTrpLysGluAlaThrIlePro
GlyHisLeuAsnSerTyrThrIleLysGlyLeuLysProGlyValValTyrGluGlyGln
LeuIleSerIleGlnGlnTyrGlyHisGlnGluValThrArgPheAspPheThrThrThr
SerThrSerThrProValThrSerAsnThrValThrGlyGluThrThrProPheSerPro
LeuValAlaThrSerGluSerValThrGluIleThrAlaSerSerPheValValSerTrp
ValSerAlaSerAspThrValSerGlyPheArgValGluTyrGluLeuSerGluGluGly
AspGluProGlnTyrLeuAspLeuProSerThrAlaThrSerValAsnIleProAspLeu
LeuProGlyArgLysTyrIleValAsnValTyrGlnIleSerGluAspGlyGluGlnSer
LeuIleLeuSerThrSerGlnThrThrAlaProAspAlaProProAspThrThrValAsp
GlnValAspAspThrSerIleValValArgTrpSerArgProGlnAlaProIleThrGly
TyrArgIleValTyrSerProSerValGluGlySerSerThrGluLeuAsnLeuProGlu
ThrAlaAsnSerValThrLeuSerAspLeuGlnProGlyValGlnTyrAsnIleThrIle
TyrAlaValGluGluAsnGlnGluSerThrProValValIleGlnGlnGluThrThrGly
ThrProArgSerAspThrValProSerProArgAspLeuGlnPheValGluValThrAsp
ValLysValThrIleMetTrpThrProProGluSerAlaValThrGlyTyrArgValAsp
ValIleProValAsnLeuProGlyGluHisGlyGlnArgLeuProIleSerArgAsnThr
PheAlaGluValThrGlyLeuSerProGlyValThrTyrTyrPheLysValPheAlaVal
SerHisGlyArgGluSerLysProLeuThrAlaGlnGlnThrThrLysLeuAspAlaPro
ThrAsnLeuGlnPheValAsnGluThrAspSerThrValLeuValArgTrpThrProPro
ArgAlaGlnIleThrGlyTyrArgLeuThrValGlyLeuThrArgArgGlyGlnProArg
GlnTyrAsnValGlyProSerValSerLysTyrProLeuArgAsnLeuGlnProAlaSer
GluTyrThrValSerLeuValAlaIleLysGlyAsnGlnGluSerProLysAlaThrGly
ValPheThrThrLeuGlnProGlySerSerIleProProTyrAsnThrGluValThrGlu
ThrThrIleValIleThrTrpThrProAlaProArgIleGlyPheLysLeuGlyValArg -continued ProSerGlnGlyGlyGluAlaProArgGluValThrSerAspSerGlySerIleValVal
SerGlyLeuThrProGlyValGluTyrValTyrThrIleGlnValLeuArgAspGlyGln
GluArgAspAlaProIleValAsnLysValValThrProLeuSerProProThrAsnLeu
HisLeuGluAlaAsnProAspThrGlyValLeuThrValSerTrpGluArgSerThrThr
ProAspIleThrGlyTyrArgIleThrThrThrProThrAsnGlyGlnGlnGlyAsnSer
LeuGluGluValValHisAlaAspGlnSerSerCysThrPheAspAsnLeuSerProGly
LeuGluTyrAsnValSerValTyrThrValLysAspAspLysGluSerValProIleSer
AspThrIleIleProAlaValProProProThrAspLeuArgPheThrAsnIleGlyPro
AspThrMetArgValThrTrpAlaProProProSerIleAspLeuThrAsnPheLeuVal
ArgTyrSerProValLysAsnGluGluAspValAlaGluLeuSerIleSerProSerAsp
AsnAlaValValLeuThrAsnLeuLeuProGlyThrGluTyrValValSerValSerSer
ValTyrGluGlnHisGluSerThrProLeuArgGlyArgGlnLysThrGlyLeuAspSer
ProThrGlyIleAspPheSerAspIleThrAlaAsnSerPheThrValHisTrpIleAla
ProArgAlaThrIleThrGlyTyrArgIleArgHisHisProGluHisPheSerGlyArg
ProArgGluAspArgValProHisSerArgAsnSerIleThrLeuThrAsnLeuThrPro
GlyThrGluTyrValValSerIleValAlaLeuAsnGlyArgGluGluSerProLeuLeu
IleGlyGlnGlnSerThrValSerAspValProArgAspLeuGluValValAlaAlaThr
ProThrSerLeuLeuIleSerTrpAspAlaProAlaValThrValArgTyrTyrArgIle
ThrTyrGlyGluThrGlyGlyAsnSerProValGlnGluPheThrValProGlySerLys
SerThrAlaThrIleSerGlyLeuLysProGlyValAspTyrThrIleThrValTyrAla
ValThrGlyArgGlyAspSerProAlaSerSerLysProIleSerIleAsnTyrArgThr
GluIleAspLysProSerGlnMetGlnValThrAspValGlnAspAsnSerIleSerVal
LysTrpLeuProSerSerSerProValThrGlyTyrArgValThrThrThrProLysAsn
GlyProGlyProThrLysThrLysThrAlaGlyProAspGlnThrGluMetThrIleGlu
GlyLeuGlnProThrValGluTyrValValSerValTyrAlaGlnAsnProSerGlyGlu
SerGlnProLeuValGlnThrAlaValThrAsnIleAspArgProLysGlyLeuAlaPhe
ThrAspValAspValAspSerIleLysIleAlaTrpGluSerProGlnGlyGlnValSer
ArgTyrArgValThrTyrSerSerProGluAspGlyIleHisGluLeuPheProAlaPro
AspGlyGluGluAspThrAlaGluLeuGlnGlyLeuArgProGlySerGluTyrThrVal
SerValValAlaLeuHisAspAspMetGluSerGlnProLeuIleGlyThrGlnSerThr
AlaIleProAlaProThrAspLeuLysPheThrGlnValThrProThrSerLeuSerAla
GlnTrpThrProProAsnValGlnLeuThrGlyTyrArgValArgValThrProLysGlu
LysThrGlyProMetLysGluIleAsnLeuAlaProAspSerSerSerValValValSer
GlyLeuMetValAlaThrLysTyrGluValSerValTyrAlaLeuLysAspThrLeuThr
SerArgProAlaGlnGlyValValThrThrLeuGluAsnValSerProProArgArgAla
ArgValThrAspAlaThrGluThrThrIleThrIleSerTrpArgThrLysThrGluThr
IleThrGlyPheGlnValAspAlaValProAlaAsnGlyGlnThrProIleGlnArgThr
IleLysProAspValArgSerTyrThrIleThrGlyLeuGlnProGlyThrAspTyrLys
IleTyrLeuTyrThrLeuAsnAspAsnAlaArgSerSerProValValIleAspAlaSer
ThrAlaIleAspAlaProSerAsnLeuArgPheLeuAlaThrThrProAsnSerLeuLeu -continued ValSerTrpGlnProProArgAlaArgIleThrGlyTyrIleIleLysTyrGluLysPro GlySerProProArgGluValValProArgProArgProGlyValThrGluAlaThrIle ThrGlyLeuGluProGlyThrGluTyrThrIleTyrValIleAlaLeuLysAsnAsnGln LysSerGluProLeuIleGlyArgLysLysThrAspGluLeuProGlnLeuValThrLeu ProHisProAsnLeuHisGlyProGluIleLeuAspValProSerThrValGlnLysThr ProPheValThrHisProGlyTyrAspThrGlyAsnGlyIleGlnLeuProGlyThrSer GlyGlnGlnProSerValGlyGlnGlnMetIlePheGluGluHisGlyPheArgArgThr ThrProProThrThrAlaThrProIleArgHisArgProArgProTyrProProAsnVal GlyGluGluIleGlnIleGlyHisIleProArgGluAspValAspTyrHisLeuTyrPro HisGlyProGlyLeuAsnProAsnAlaSerThrGlyGlnGluAlaLeuSerGlnThrThr IleSerTrpAlaProPheGlnAspThrSerGluTyrIleIleSerCysHisProValGly ThrAspGluGluProLeuGlnPheArgValProGlyThrSerThrSerAlaThrLeuThr GlyLeuThrArgGlyAlaThrTyrAsnValIleValGluAlaLeuLysAspGlnGlnArg HisLysValArgGluGluValValThrValGlyAsnSerValAsnGluGlyLeuAsnGln ProThrAspAspSerCysPheAspProTyrThrValSerHisTyrAlaValGlyAspGlu TrpGluArgMetSerGluSerGlyPheLysLeuLeuCysGlnCysLeuGlyPheGlySer GlyHisPheArgCysAspSerSerArgTrpCysHisAspAsnGlyValAsnTyrLysIle GlyGluLysTrpAspArgGlnGlyGluAsnGlyGlnMetMetSerCysThrCysLeuGly AsnGlyLysGlyGluPheLysCysAspProHisGluAlaThrCysTyrAspAspGlyLys ThrTyrHisValGlyGluGlnTrpGlnLysGluTyrLeuGlyAlaIleCysSerCysThr CysPheGlyGlyGlnArgGlyTrpArgCysAspAsnCysArgArgProGlyGlyGluPro SerProGluGlyThrThrGlyGlnSerTyrAsnGlnTyrSerGlnArgTyrHisGlnArg ThrAsnThrAsnValAsnCysProIleGluCysPheMetProLeuAspValGlnAlaAsp ArgGluAspSerArgGlu

40

Various modifications and variations of the described methods, pharmaceutical compositions, and kits of the disclosure will be apparent to those skilled in the art without departing from the scope and spirit of the disclosure. Although the disclosure has been described in connection with specific embodiments, it will be understood that it is capable of further modifications and that the disclosure as claimed should not be unduly limited to such specific embodiments. Indeed, various modifications of the described modes for carrying out the disclosure that are obvious to those skilled in the art are intended to be within the scope of the disclosure. This application is intended to cover any variations, uses, or adaptations of the disclosure following, in general, the principles of the disclosure and including such departures from the present disclosure come within known customary practice within the art to which the disclosure pertains and may be applied to the essential features herein before set forth.

Sequence Listing Xml Incorporation Statement

The herewith provided Sequence Listing XML is hereby incorporated by reference. The name of the XML file is SeqListUSC1513.xml with a date of creation of Oct. 14, 2022 and a size of 11 KB.

SEQUENCE LISTING

```
Sequence total quantity: 6
SEQ ID NO: 1           moltype = AA  length = 390
FEATURE                Location/Qualifiers
source                 1..390
                       mol_type = protein
                       organism = Homo sapiens
SEQUENCE: 1
MPPSGLRLLL LLLPLLWLLV LTPGRPAAGL STCKTIDMEL VKRKRIEAIR GQILSKLRLA  60
SPPSQGEVPP GPLPEAVLAL YNSTRDRVAG ESAEPEPEPE ADYYAKEVTR VLMVETHNEI 120
YDKFKQSTHS IYMFFNTSEL REAVPEPVLL SRAELRLLRL KLKVEQHVEL YQKYSNNSWR 180
YLSNRLLAPS DSPEWLSFDV TGVVRQWLSR GGEIEGFRLS AHCSCDSRDN TLQVDINGFT 240
TGRRGDLATI HGMNRPFLLL MATPLERAQH LQSSRHRRAL DTNYCFSSTE KNCCVRQLYI 300
```

```
DFRKDLGWKW IHEPKGYHAN FCLGPCPYIW SLDTQYSKVL ALYNQHNPGA SAAPCCVPQA 360
LEPLPIVYYV GRKPKVEQLS NMIVRSCKCS                                 390

SEQ ID NO: 2           moltype = AA  length = 212
FEATURE                Location/Qualifiers
source                 1..212
                       mol_type = protein
                       organism = Homo sapiens
SEQUENCE: 2
MNSFSTSAFG PVAFSLGLLL VLPAAFPAPV PPGEDSKDVA APHRQPLTSS ERIDKQIRYI 60
LDGISALRKE TCNKSNMCES SKEALAENNL NLPKMAEKDG CFQSGFNEET CLVKIITGLL 120
EFEVYLEYLQ NRFESSEEQA RAVQMSTKVL IQFLQKKAKN LDAITTPDPT TNASLLTKLQ 180
AQNQWLQDMT THLILRSFKE FLQSSLRALR QM                              212

SEQ ID NO: 3           moltype = AA  length = 215
FEATURE                Location/Qualifiers
source                 1..215
                       mol_type = protein
                       organism = Homo sapiens
SEQUENCE: 3
MGKGDPKKPR GKMSSYAFFV QTCREEHKKK HPDASVNFSE FSKKCSERWK TMSAKEKGKF 60
EDMAKADKAR YEREMKTYIP PKGETKKKFK DPNAPKRPPS AFFLFCSEYR PKIKGEHPGL 120
SIGDVAKKLG EMWNNTAADD KQPYEKKAAK LKEKYEKDIA AYRAKGKPDA AKKGVVKAEK 180
SKKKKEEEED EEDEEDEEEE EDEEDEDEEE DDDDE                           215

SEQ ID NO: 4           moltype = AA  length = 795
FEATURE                Location/Qualifiers
source                 1..795
                       mol_type = protein
                       organism = Homo sapiens
SEQUENCE: 4
MSKRHRLDLG EDYPSGKKRA GTDGKDRDRD RDREDRSKDR DRERDRGDRE REREKEKEKE 60
LRASTNAMLI SAGLPPLKAS HSAHSTHSAH STHSTHSAHS THAGHAGHTS LPQCINPFTN 120
LPHTPRYYDI LKKRLQLPVW EYKDRFTDIL VRHQSFVLVG ITGSGKTTQI PQWCVEYMRS 180
LPGPKRGVAC TQPRRVAAMS VAQRVADEMD VMLGQEVGYS IRFEDCSSAK TILKYMTDGM 240
LLREAMNDPL LERYGVIILD EAHERTLATD ILMGVLKEVV RQRSDLKIVV MSATLDAGKF 300
QIYFDNCPLL TIPGRTHPVE IFYTPEPERD YLEAAIRTVI QIHMCEEEEG DLLLFLTGQE 360
EIDEACKRIK REVDDLGPEV GDIKIIPLYS TLPPQQQQRI FEPPPPKKQN GAIGRKVVVS 420
TNIAETSLTI DGVVFVIDPG FAKQKVYNPR IRVESLLVTA ISKASAQQRA GRAGRTRPGK 480
CFRLYTEKAY KTEMQDNTYP EILRSNLGSV VLQLKKLGID DLVHFDFMDP PAPETLMRAL 540
ELLNYLAALN DDGDLTELGS MMAEFPLDPQ LAKMVIASCD YNCSNEVLSI TAMLSVPQCF 600
VRPTEAKKAA DEAKMRFAHI DGDHLTLLNV YHAFKQNHES VQWCYDNFIN YRSLMSADNV 660
RQQLSRIMDR FNLPRRSTDF TSRDYYINIR KALVTGYFMQ VAHLERTGHY LTVKDNQVVQ 720
LHPSTVLDHK PEWVLYNEFV LTTKNYIRTC TDIKPEWLVK IAPQYYDMSN FPQCEAKRQL 780
DRIIAKLQSK EYSQY                                                 795

SEQ ID NO: 5           moltype = AA  length = 882
FEATURE                Location/Qualifiers
source                 1..882
                       mol_type = protein
                       organism = Homo sapiens
SEQUENCE: 5
MGPWSRSLSA LLLLLQVSSW LCQEPEPCHP GFDAESYTFT VPRRHLERGR VLGRVNFEDC 60
TGRQRTAYFS LDTRFKVGTD GVITVKRPLR FHNPQIHFLV YAWDSTYRKF STKVTLNTVG 120
HHHRPPPHQA SVSGIQAELL TFPNSSPGLH RQKRDWVIPP ISCPENEKGP FPKNLVQIKS 180
NKDKEGKVFY SITGQGADTP PVGVFIIERE TGWLKVTEPL DRERIATYTL FSHAVSSNGN 240
AVEDPMEILI TVTDQNDNKP EFTQEVFKGS VMEGALPGTS VMEVTATDAD DDVNTYNAAI 300
AYTILSQDPE LPDKNMFTIN RNTGVISVVT TGLDRESFPT YTLVVQAADL QGEGLSTTAT 360
AVITVTDTND NPPIFNPTTY KGQVPENEAN VVITTLKVTD ADAPNTPAWE AVYTILNDDG 420
GQFVVTTNPV NNDGILKTAK GLDFEAKQQY ILHVAVTNVV PFEVSLTTST ATVTVDVLDV 480
NEAPIFVPPE KRVEVSEDFG VGQEITSYTA QEPDTFMEQK ITYRIWRDTA NWLEINPDTG 540
AISTRAELDR EDFEHVKNST YTALIIATDN GSPVATGTGT LLLILSDVND NAPIPEPRTI 600
FFCERNPKPQ VINIIDADLP PNTSPFTAEL THGASANWTI QYNDPTQESI ILKPKMALEV 660
GDYKINLKLM DNQNKDQVTT LEVSVCDCEG AAGVCRKAQP VEAGLQIPAI LGILGGILAL 720
LILILLLLLF LRRRAVVKEP LLPPEDDTRD NVYYYDEEGG GEEDQDFDLS QLHRGLDARP 780
EVTRNDVAPT LMSVPRYLPR PANPDEIGNF IDENLKAADT DPTAPPYDSL LVFDYEGSGS 840
EAASLSSLNS SESDKDQDYD YLNEWGNRFK KLADMYGGGE DD                   882

SEQ ID NO: 6           moltype = AA  length = 2386
FEATURE                Location/Qualifiers
source                 1..2386
                       mol_type = protein
                       organism = Homo sapiens
SEQUENCE: 6
MLRGPGPGLL LLAVQCLGTA VPSTGASKSK RQAQQMVQPQ SPVAVSQSKP GCYDNGKHYQ 60
INQQWERTYL GNALVCTCYG GSRGFNCESK PEAEETCFDK YTGNTYRVGD TYERPKDSMI 120
WDCTCIGAGR GRISCTIANR CHEGGQSYKI GDTWRRPHET GGYMLECVCL GNGKGEWTCK 180
PIAEKCFDHA AGTSYVVGET WEKPYQGWMM VDCTCLGEGS GRITCTSRNR CNDQDTRTSY 240
RIGDTWSKKD NRGNLLQCIC TGNGRGEWKC ERHTSVQTTS SGSGPFTDVR AAVYQPQPHP 300
```

```
QPPPYGHCVT DSGVVYSVGM QWLKTQGNKQ MLCTCLGNGV SCQETAVTQT YGGNSNGEPC  360
VLPFTYNGRT FYSCTTEGRQ DGHLWCSTTS NYEQDQKYSF CTDHTVLVQT RGGNSNGALC  420
HFPFLYNNHN YTDCTSEGRR DNMKWCGTTQ NYDADQKFGF CPMAAHEEIC TTNEGVMYRI  480
GDQWDKQHDM GHMMRCTCVG NGRGEWTCIA YSQLRDQCIV DDITYNVNDT FHKRHEEGHM  540
LNCTCFGQGR GRWKCDPVDQ CQDSETGTFY QIGDSWEKYV HGVRYQCYCY GRGIGEWHCQ  600
PLQTYPSSSG PVEVFITETP SQPNSHPIQW NAPQPSHISK YILRWRPKNS VGRWKEATIP  660
GHLNSYTIKG LKPGVVYEGQ LISIQQYGHQ EVTRFDFTTT STSTPVTSNT VTGETTPFSP  720
LVATSESVTE ITASSFVVSW VSASDTVSGF RVEYELSEEG DEPQYLDLPS TATSVNIPDL  780
LPGRKYIVNV YQISEDGEQS LILSTSQTTA PDAPPDTTVD QVDDTSIVVR WSRPQAPITG  840
YRIVYSPSVE GSSTELNLPE TANSVTLSDL QPGVQYNITI YAVEENQEST PVVIQQETTG  900
TPRSDTVPSP RDLQFVEVTD VKVTIMWTPP ESAVTGYRVD VIPVNLPGEH GQRLPISRNT  960
FAEVTGLSPG VTYYFKVFAV SHGRESKPLT AQQTTKLDAP TNLQFVNETD STVLVRWTPP 1020
RAQITGYRLT VGLTRRGQPR QYNVGPSVSK YPLRNLQPAS EYTVSLVAIK GNQESPKATG 1080
VFTTLQPGSS IPPYNTEVTE TTIVITWTPA PRIGFKLGVR PSQGGEAPRE VTSDSGSIVV 1140
SGLTPGVEYV YTIQVLRDGQ ERDAPIVNKV VTPLSPPTNL HLEANPDTGV LTVSWERSTT 1200
PDITGYRITT TPTNGQQGNS LEEVVHADQS SCTFDNLSPG LEYNVSVYTV KDDKESVPIS 1260
DTIIPAVPPP TDLRFTNIGP DTMRVTWAPP PSIDLTNFLV RYSPVKNEED VAELSISPSD 1320
NAVVLTNLLP GTEYVVSVSS VYEQHESTPL RGRQKTGLDS PTGIDFSDIT ANSFTVHWIA 1380
PRATITGYRI RHHPEHFSGR PREDRVPHSR NSITLTNLTP GTEYVVSIVA LNGREESPLL 1440
IGQQSTVSDV PRDLEVVAAT PTSLLISWDA PAVTVRYYRI TYGETGGNSP VQEFTVPGSK 1500
STATISGLKP GVDYTITVYA VTGRGDSPAS SKPISINYRT EIDKPSQMQV TDVQDNSISV 1560
KWLPSSSPVT GYRVTTTPKN GPGPTKTKTA GPDQTEMTIE GLQPTVEYVV SVYAQNPSGE 1620
SQPLVQTAVT NIDRPKGLAF TDVDVDSIKI AWESPQGQVS RYRVTYSSPE DGIHELFPAP 1680
DGEEDTAELQ GLRPGSEYTV SVVALHDDME SQPLIGTQST AIPAPTDLKF TQVTPTSLSA 1740
QWTPPNVQLT GYRVRVTPKE KTGPMKEINL APDSSSVVVS GLMVATKYEV SVYALKDTLT 1800
SRPAQGVVTT LENVSPPRRA RVTDATETTI TISWRTKTET ITGFQVDAVP ANGQTPIQRT 1860
IKPDVRSYTI TGLQPGTDYK IYLYTLNDNA RSSPVVIDAS TAIDAPSNLR FLATTPNSLL 1920
VSWQPPRARI TGYIIKYEKP GSPPREVVPR PRPGVTEATI TGLEPGTEYT IYVIALKNNQ 1980
KSEPLIGRKK TDELPQLVTL PHPNLHGPEI LDVPSTVQKT PFVTHPGYDT GNGIQLPGTS 2040
GQQPSVGQQM IFEEHGFRRT TPPTTATPIR HRPRPYPPNV GEEIQIGHIP REDVDYHLYP 2100
HGPGLNPNAS TGQEALSQTT ISWAPFQDTS EYIISCHPVG TDEEPLQFRV PGTSTSATLT 2160
GLTRGATYNV IVEALKDQQR HKVREEVVTV GNSVNEGLNQ PTDDSCFDPY TVSHYAVGDE 2220
WERMSESGFK LLCQCLGFGS GHFRCDSSRW CHDNGVNYKI GEKWDRQGEN GQMMSCTCLG 2280
NGKGEFKCDP HEATCYDDGK TYHVGEQWQK EYLGAICSCT CFGGQRGWRC DNCRRPGGEP 2340
SPEGTTGQSY NQYSQRYHQR TNTNVNCPIE CFMPLDVQAD REDSRE           2386
```

What is claimed is:

1. An anti-cancer drug comprising:
   at least one biomimetic nanoparticle integrated with at least one biodegradable dendritic mesoporous nanoparticle; and
   at least one camouflage coating substantially covering the at least one biomimetic nanoparticle integrated with the at least one biodegradable dendritic mesoporous nanoparticle.

2. The anti-cancer drug of claim 1, wherein the at least one biomimetic nanoparticle comprises at least one cerium oxide nanoparticle.

3. The anti-cancer drug of claim 1, wherein the at least one biodegradable dendritic mesoporous nanoparticle comprises silica to form at least one biodegradable dendritic mesoporous organosilica nanoparticle.

4. The anti-cancer drug of claim 1, wherein the at least one biomimetic nanoparticle prevents at least one fibroblast undergoing TGFβ-induced ROS-dependent transdifferentiation to form at least one myofibroblast.

5. The anti-cancer drug of claim 1, wherein the at least one biomimetic nanoparticle causes reverse transdifferentiation of at least one cancer-associated fibroblast to at least one fibroblast.

6. The anti-cancer drug of claim 1, wherein the at least one camouflage coating comprises at least one homologous cell membrane.

7. The anti-cancer drug of claim 6, wherein the at least one homologous cell membrane is formed from at least one breast cancer cell.

8. The anti-cancer drug of claim 7, wherein the at least one homologous cell membrane comprises at least one membrane protein from the at least one breast cancer cell, wherein the at least one membrane protein retains its adhesion protein function.

9. The anti-cancer drug of claim 1, wherein the at least one camouflage coating substantially covering the at least one biomimetic nanoparticle integrated with the at least one biodegradable dendritic mesoporous nanoparticle is introduced to a subject followed by exposing the subject to doxorubicin.

* * * * *